(12) United States Patent
Kazantsev et al.

(10) Patent No.: US 11,439,711 B2
(45) Date of Patent: *Sep. 13, 2022

(54) DEGRADABLE THIOL-ENE POLYMERS AND METHODS OF MAKING THEREOF

(71) Applicant: MOSAIC BIOSCIENCES, INC., Boulder, CO (US)

(72) Inventors: Alexei V. Kazantsev, Erie, CO (US); Peter D. Mariner, Superior, CO (US); Martin Stanton, Boulder, CO (US)

(73) Assignee: Mosaic Biosciences, Inc., Boulder, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/085,798

(22) Filed: Oct. 30, 2020

(65) Prior Publication Data

US 2021/0154306 A1 May 27, 2021

Related U.S. Application Data

(63) Continuation of application No. 15/549,787, filed as application No. PCT/US2016/017189 on Feb. 9, 2016, now Pat. No. 10,912,837.

(60) Provisional application No. 62/114,034, filed on Feb. 9, 2015.

(51) Int. Cl.

| | | |
|---|---|---|
| A61K 47/60 | (2017.01) | |
| C08G 75/12 | (2016.01) | |
| C08G 75/045 | (2016.01) | |
| C08J 3/24 | (2006.01) | |
| C08G 81/00 | (2006.01) | |
| C08H 1/00 | (2006.01) | |
| C07K 1/107 | (2006.01) | |
| C12N 9/36 | (2006.01) | |
| C08B 37/00 | (2006.01) | |
| C07K 14/78 | (2006.01) | |
| C08J 3/075 | (2006.01) | |
| C08L 101/16 | (2006.01) | |
| A61K 9/06 | (2006.01) | |
| A61K 38/08 | (2019.01) | |
| A61K 38/10 | (2006.01) | |
| A61K 38/39 | (2006.01) | |
| C08G 65/334 | (2006.01) | |

(52) U.S. Cl.
CPC ............... *A61K 47/60* (2017.08); *A61K 9/06* (2013.01); *A61K 38/08* (2013.01); *A61K 38/10* (2013.01); *A61K 38/39* (2013.01); *C07K 1/1077* (2013.01); *C07K 14/78* (2013.01); *C08B 37/0069* (2013.01); *C08B 37/0075* (2013.01); *C08G 65/3342* (2013.01); *C08G 75/045* (2013.01); *C08G 75/12* (2013.01); *C08G 81/00* (2013.01); *C08H 1/00* (2013.01); *C08J 3/075* (2013.01); *C08J 3/246* (2013.01); *C08L 101/16* (2013.01); *C12N 9/2462* (2013.01); *C12Y 302/01017* (2013.01); *C08G 2210/00* (2013.01); *C08G 2650/04* (2013.01); *C08G 2650/16* (2013.01); *C08G 2650/20* (2013.01); *C08J 2300/16* (2013.01); *C08J 2371/02* (2013.01); *C08J 2389/00* (2013.01)

(58) Field of Classification Search
None
See application file for complete search history.

(56) References Cited

U.S. PATENT DOCUMENTS

| | | |
|---|---|---|
| 3,920,877 A | 11/1975 | Barber |
| 4,081,598 A | 3/1978 | Morgan |
| 4,808,638 A | 2/1989 | Steinkraus |
| 4,969,998 A | 11/1990 | Henn |
| 5,177,056 A | 1/1993 | Hilti |
| 5,399,624 A | 3/1995 | Glaser |
| 5,410,016 A | 4/1995 | Hubbell |
| 5,496,872 A | 3/1996 | Constancis |
| 5,730,601 A | 3/1998 | Bowman |

(Continued)

FOREIGN PATENT DOCUMENTS

| | | |
|---|---|---|
| GB | 588018 A | 5/1947 |
| JP | S63280711 A | 11/1988 |

(Continued)

OTHER PUBLICATIONS

Anderson, S.B. et al. (May 2011). "The Performance of Human Mesenchymal Stem Cells Encapsulated in Cell-Degradable Polymer-peptide Hydrogels," Biomaterials 32(14):3564-3574.

(Continued)

*Primary Examiner* — Fred H Reynolds
(74) *Attorney, Agent, or Firm* — Morrison & Foerster LLP

(57) ABSTRACT

Provided are methods for linking polypeptides (including peptides and proteins) to other moieties using radical imitated thiol-ene chemistries, for example, modifying a polypeptide by introducing reactive thiol groups and reacting the thiol groups with olefin-containing reagents or alkyne-containing reagents under conditions that support radical thiol-ene or thiol-yne reactions. The reactive thiol groups have greater activity for radical thiol-ene reactions that a cysteine thiol group, including thiol groups that are separated from the peptide backbone by at least two carbon atoms, for example, the thiol group of a homocysteine residue. Also provided are compositions and biomaterials containing the linked polypeptides, for example, peptide and protein conjugates, and thiol-ene based biocompatible hydrogel polymers, and their uses in the medical field.

13 Claims, 13 Drawing Sheets
Specification includes a Sequence Listing.

(56) References Cited

U.S. PATENT DOCUMENTS

| | | | |
|---|---|---|---|
| 5,837,751 | A | 11/1998 | Jacobine |
| 5,858,746 | A | 1/1999 | Hossainy |
| 6,060,582 | A | 5/2000 | Hubbell |
| 6,169,126 | B1 | 1/2001 | Szum |
| 7,018,655 | B2 | 3/2006 | Lele |
| 7,288,608 | B2 | 10/2007 | Bowman |
| 7,744,912 | B1 | 6/2010 | Hubbell |
| 7,842,667 | B2 | 11/2010 | Seliktar |
| 8,519,086 | B2 | 8/2013 | Bowman |
| 8,859,716 | B2 | 10/2014 | Bowman |
| 9,631,092 | B2 | 4/2017 | Bowman |
| 9,987,393 | B2 | 6/2018 | Anseth |
| 9,988,433 | B2 | 6/2018 | Kazantsev |
| 10,016,505 | B2 | 7/2018 | Mariner |
| 10,189,952 | B2 | 1/2019 | Bowman |
| 10,912,837 | B2 * | 2/2021 | Kazantsev ............ A61K 38/39 |
| 11,130,797 | B2 | 9/2021 | Kazantsev et al. |
| 11,160,866 | B2 | 11/2021 | Mariner et al. |
| 2002/0004537 | A1 | 1/2002 | Krongauz |
| 2002/0076443 | A1 | 6/2002 | Stein |
| 2004/0086479 | A1 | 5/2004 | Grinstaff |
| 2004/0091462 | A1 | 5/2004 | Lin |
| 2005/0244393 | A1 | 11/2005 | Philippart |
| 2006/0029578 | A1 | 2/2006 | Hoemann |
| 2006/0204582 | A1 | 9/2006 | Stein |
| 2007/0248567 | A1 | 10/2007 | Pathak |
| 2009/0311338 | A1 | 12/2009 | Pathak |
| 2009/0324720 | A1 | 12/2009 | He |
| 2010/0137510 | A1 | 6/2010 | Seliktar |
| 2010/0178355 | A1 | 7/2010 | Marchand |
| 2010/0233246 | A1 | 9/2010 | Sehl |
| 2010/0291357 | A1 | 11/2010 | Polizzotti |
| 2010/0304338 | A1 | 12/2010 | Cramer |
| 2012/0202263 | A1 | 8/2012 | Blakely |
| 2012/0220542 | A1 | 8/2012 | Barrack |
| 2012/0225101 | A1 | 9/2012 | Kao |
| 2013/0197189 | A1 | 8/2013 | Aimetti |
| 2014/0038826 | A1 | 2/2014 | Anseth |
| 2014/0112960 | A1 | 4/2014 | Lin |
| 2017/0247541 | A1 | 8/2017 | Bowman |
| 2018/0043030 | A1 | 2/2018 | Kazantsev |
| 2018/0355019 | A1 | 12/2018 | Kazantsev |
| 2018/0360970 | A1 | 12/2018 | Mariner |

FOREIGN PATENT DOCUMENTS

| | | |
|---|---|---|
| RU | 2488863 C2 | 7/2013 |
| WO | 2009039307 A2 | 3/2009 |
| WO | 2009085902 A1 | 7/2009 |
| WO | 2012103445 A2 | 8/2012 |
| WO | 2013116791 A1 | 8/2013 |
| WO | 2016130573 A2 | 8/2016 |

OTHER PUBLICATIONS

Athanasiou, K.A et al. (1996). "Sterilization, Toxicity, Biocompatibility and Clinical Applications of Polylactic Acid/Polyglycolic Acid Copolymers," Biomaterials 17(2):93-102.

Benesch, R. et al. (1958). "Thiolation of Proteins," Biochemistry 44:848-853.

Cadée, J.A. et al. (Jun. 5, 2000). "In Vivo Biocompatibility of Dextran-Based Hydrogels," J Biomed Mater Res. 50(3):397-404.

Canalle, L.A. et al. (2010). "Polypeptide-Polymer Bioconjugates," Chem. Soc. Rev. 39:329-353.

Chalker, J.M. et al. (Jul. 7, 2009, e-published on May 27, 2009). "Enabling Olefin Metathesis on Proteins: Chemical Methodsfor Installation of S-Allyl Cysteine," Chem. Commun. 25:3714-3716.

Claudino, M. et al. (2013) "Thiol-ene Coupling Kinetics of D-Limonene: A Versatile 'Non-Click' Free-Radical Reaction Involving a Natural Terpene," RSC Adv. 3:11021-11034.

Conte, M.L. et al. (2011). "Multi-Molecule Reaction of Serum Albumin Can Occur Through Thiol-Yne Coupling," Chemical Communications 47:11086-11088.

Cramer, N.B. et al. (2003) "Thiol-Ene Photopolymerization Mechanism and Rate Limiting Step Changes for Various Vinyl Functional Group Chemistries," Macromolecules 36:7964-7969.

Dondoni, A. et al. (2009). "A New Ligation Strategy for Peptide and Protein Glycosylation: Photoinduced Thiol-Ene Coupling," Chem. Eur.J. 15:11444-11449.

Draye, J.-P et al. (Sep. 1998). "In Vitro and in Vivo Biocompatibility of Dextran Dialdehyde Cross-linked Gelatin Hydrogel Films," Biomaterials 19(18):1677-1687.

Espeel, P. et al. (Jan. 25, 2011). "One-Pot Multistep Reactions Based on Thiolactones: Extending the Realm of Thiol-Ene Chemistry in Polymer Synthesis," Journal of the American Chemical Society 133:1678-1681.

European Extended Search Report dated Sep. 10, 2018 for EP Application No. 16749732.0 filed on Sep. 7, 2017, 9 pages.

European Office Action for Application 13743245.6 dated Jan. 18, 2017, 5 pages.

European Office Action dated Jun. 28, 2019 for EP Application No. 16749732.0 filed on Sep. 7, 2017, 3 pages.

European Supplementary Search Report dated Dec. 14, 2015, for European Patent Application No. 137432456, filed on Feb. 1, 2013, 11 pages.

Fairbanks, B.D. et al. (2009). "Thiol-Yne Photopolymerizations; Novel Mechanism, Kinetics, and Step-Growth Formation of Highly Cross-Linked Networks," Macromolecules 42:211-217.

Fairbanks, B.D. et al. (2009; e-pub. Sep. 23, 2009). "Photoinitiated Polymerization of PEG-Diacrylate with Lithium Phenyl-2,4,6-Trimethylbenzoylphasphinate: Polymerization Rate and Cytocompatibility," Biomaterials 30:6702-6707.

Fairbanks, B.D. et al. (2010) "Reaction Rates and Mechanisms for Radical, Photoinitated Addition of Thiols to Alkynes, and Implications for Thiol-Yne Photopolymerizations and Click Reactions," Macromolecules 43:4113-4119.

Floyd, N. et al., (2009). "Thiyl Glycosylation of Olefinic Proteins: S-Linked Glycoconjugate Synthesis," Angewandte Chemie. Int. Ed. 48:7798-7802.

Fu, Y. et al. (Jan. 2012). "3D Cell Entrapment in Crosslinked Thiolated Gelatin-poly(ethylene glycol) Diacrylate Hydrogels," Biomaterials 33(1):48-58.

Fu, Y. et al., (Aug. 2011). "In Situ Forming poly(ethylene glycol)-Based Hydrogels via Thiol-Maleimide Michael-Type Addition," J Biomed. Mater. Res. A 98(2):201-211.

Gallez, B. et al. (Jul. 1998). "Small Particles of Fusinite and Carbohydrate Chars Coated with Aqueous Soluble Polymers: Preparation and Applications for In Vivo EPR Oximetry," Magn Reson Med 40(1):152-159.

Geyer, U. et al. (1994). "Formation, Derivatization and Applications of Bacterial Cellulose," Int. J. Biol. Macromol. 16(6):343-347.

Hernandez, K. et al. (2011). "Control Of Protein Immobilization: Coupling Immobilization and Site-Directed Mutagenesis to Improve Biocatalyst or Biosensor Performance," Enzyme And Microbial Technology 48:107-122.

Hoyle, C.E. et al. (2004). "Thiol-Enes: Chemistry of the Past with Promise for the Future" Journal of Polymer Science: Part A: Polymer Chemistry 42:5301-5338.

International Preliminary Report On Patentability dated Aug. 30, 2012 for PCT Patent Application No. PCT/US2012/022920, filed on Jan. 27, 2012, 8 pages.

International Preliminary Report on Patentability dated Aug. 24, 2017, for PCT/US2016/017189, filed on Feb. 9, 2016, 8 pages.

International Search Report and Written Opinion dated Aug. 30, 2012, for PCT Patent Application No. PCT/US2012/022920, Internationally filed on Jan. 27, 2012, 9 pages.

International Search Report dated Apr. 11, 2013 for PCT Patent Application No. PCT/US2013/024520 filed on Feb. 1, 2013, 3 pages.

International Search Report dated Aug. 18, 2016, for PCT Patent Application No. PCT/US2016/17189, Internationally filed on Feb. 9, 2016, 4 pages.

International Search Report dated Jan. 3, 2003, for PCT Patent Application No. PCT/US02/32669, filed Oct. 10, 2002, 1 page.

(56) References Cited

OTHER PUBLICATIONS

Jain, R.A. (2000). "The Manufacturing Techniques of Various Drug Loaded Biodegradable Poly(lactide-co-glycolide) (PLGA) Devices," Biomaterials 21:2475-2490.
Jin, R. et al. (Jun. 2010). "Synthesis and characterization of hyaluronic acid-poly(enthylene glycol) hydrogels via Michael addition: An injectable biomaterial for cartilage repair," Acta Biomaterialia 6(6):1968-1977.
Jones, M.W. et al. (2009, e-pub. Jul. 21, 2009). "Phosphine-Mediated One-Pot Thiol-Ene "Click" Approach to Polymer-Protein Conjugates," Chem. Commun. 5272-5274.
Lee, S. et al. (2016 ; e-published on Nov. 23, 2015). "Fabrication of PEG-carboxymethylcellulose Hydrogel by Thiol-norbornene Photoclick Chemistry," International Journal of Biological Macromolecules 83:1-8.
Li, Y. et al., (2012). "Genetically Encoded Alkenyl-Pyrrolysine Analogues for Thiol-Ene Reaction Mediated Site-Specific Protein Labeling" Chemical Science 3:2766-2770.
Lin, C.C. et al. (2011) "PEG Hydrogels Formed by Thiol-Ene Photo-Click Chemistry and Their Effect on the Formation and Recovery of Insulin-Secreting Cell Spheroids" Biomaterials 32(36):9685-9695.
Lin, S.S. et al. (Aug. 30-Sep. 3, 2006). "Controlled Release of PRP-Derived Growth Factors Promotes Osteogenic Differentiation of Human Mesenchymal Stem Cells," Proceedings of the 28th IEEE EMBS Annual International Conference, New York, USA, SaA06. 4:4358-4361.
Lowe A.B. (2010). "Thiol-ene "click" Reactions and Recent Applications In Polymer And Materials Synthesis," Polym. Chem. 1(1):17-36.
Lowe A.B. (2014). "Thiol-ene "click" Reactions and Recent Applications In Polymer And Materials Synthesis: A First Update," Polym. Chem. 5:4820-4870.
Lowe, A.B. et al. (2010). "Thiol-yne Click Chemistry: A Powerful and Versatile Methodology for Materials Synthesis," Journal of Materials Chemistry, 20:4745-4750.
Maleimide, retrieved from www.en.wikipedia.org/wiki/Maleimides on Mar. 3, 2012, 3 pages.
Mccall, J.D. et al. (2012) "Thiol-Ene Photopolymerizations Provide a Facile Method To Encapsulate Proteins and Maintain Their Bioactivity", Biomacromolecules 13:2410-2417.
Moreira, H. et al. (Feb. 2000). "Use of Bioresorbable Membrane (Sodium Hyaluronate + Carboxymethylcellulose) After Controlled Bowel Injuries in a Rabbit Model," Diseases of the Colon Rectum 43(2):182-187.
Northrop, B.H. et al. (2012). "Thiol-Ene Click Chemistry: Computational and Kinetic Analysis of the Influence of Alkene Functionality," Journal of the American Chemical Society 134:13804-13817.
Pfeifer C. S. et al. (Jul. 7, 2011). "Delayed Gelation Through Chain-Transfer Reactions: Mechanism For Stress Reduction In Methacrylate Networks." Polymer 52(15):3295-3303, 21 pages.
Qiu, B. et al. (2003). "A Hydrogel Prepared by in Situ Cross-Linking of a Thiol-Containing Poly(Ethylene Glycol)-Based Copolymer A New Biomaterial for Protein Drug Delivery," Biomaterials 24:11-18.
Raza, A. et al. (2013). "The Influence of Matrix Degradation and Functional on Cell Survival and Morphogenesis in PEG-Based Hydrogels," Macromolecular Bioscience 13(8):1048-1058.
Roberts, J.J. et al. (2013). "Comparison of Photopolymerizable Thiol-ene PEG and Acrylate-based PEG Hydrogels tor Cartilage Development," Biomaterials 34(38):9969-9979.
Roskos, K.V. et al. (1995). "Biocompatibility and in Vivo Morphine Diffusion into a Placebo Morphine-triggered Naltrexone Delivery Device in Rabbits," Biomaterials 16(16):1235-1239.
Russo, L. et al. (Mar. 2016; e-published on Dec. 9, 2015). "Gelatin Hydrogels via Thiol-ene Chemistry," Monatshefte Für Chemie 147(3):587-592.
Sawicki, L.A. et al. (Nov. 30, 2014). "Design of Thiol-Ene Photoclick Hydrogels Using Facile Techniques for Cell Culture Applications," Biomaterials Science 2(11):1612-1626.
Sell, S.A. et al. (Dec. 2012; e-published on Sep. 25, 2012) "The Incorporation and Controlled Release of Platlet-Rich Plasma-Derived Biomolecules From Polymeric Tissue Engineering Scaffolds," Polym. Int. 61(12):1703-1709.
Solomons, T.W.G. (1988). "Homolytic Bond Dissociation Energies and the Relative Stabilities of Free Radicals," in Organic Chemistry, 4th edition, pp. 402-403, 4 pages.
U.S. Final Office Action dated Apr. 8, 2020, for U.S. Appl. No. 15/971,700, filed May 4, 2018, 13 pages.
U.S. Final Office Action dated Jan. 29, 2016, for U.S. Appl. No. 14/210,106, filed Mar. 13, 2014, 11 pages.
U.S. Final Office Action dated Jun. 5, 2006, for U.S. Appl. No. 10/269,916, filed Oct. 10, 2002, 7 pages.
U.S. Final Office Action dated Jun. 29, 2017, for U.S. Appl. No. 14/210,106, filed Mar. 13, 2014, 14 pages.
U.S. Final Office Action dated Mar. 10, 2009, for U.S. Appl. No. 11/858,062, filed Sep. 19, 2007, 6 pages.
U.S. Final Office Action dated May 31, 2011, for U.S. Appl. No. 12/556,640, filed Sep. 10, 2009, 5 pages.
U.S. Final Office Action dated Nov. 30, 2015, for U.S. Appl. No. 13/981,885, filed Oct. 9, 2013, 17 pages.
U.S. Final Office Action dated Oct. 3, 2016, for U.S. Appl. No. 13/758,942, filed Feb. 4, 2013, 11 pages.
U.S. Final Office Action dated Sep. 14, 2012, for U.S. Appl. No. 12/556,640, filed Sep. 10, 2009, 10 pages.
U.S. Non Final Office Action dated Apr. 3, 2015, for U.S. Appl. No. 13/981,885, filed Oct. 9, 2013, 16 pages.
U.S. Non Final Office Action dated Aug. 6, 2008, for U.S. Appl. No. 11/858,062, filed Sep. 19, 2007, 6 pages.
U.S. Non Final Office Action dated Dec. 30, 2005, for U.S. Appl. No. 10/269,916, filed Oct. 10, 2002, 6 pages.
U.S. Non Final Office Action dated Dec. 31, 2015, for U.S. Appl. No. 13/758,942, filed Feb. 4, 2013,14 pages.
U.S. Non Final Office Action dated Jul. 16, 2015, for U.S. Appl. No. 14/210,106, filed Mar. 13, 2014, 10 pages.
U.S. Non Final Office Action dated Jul. 18, 2016, for U.S. Appl. No. 13/981,885, filed Oct. 9, 2013, 18 pages.
U.S. Non Final Office Action dated May 19, 2016, for U.S. Appl. No. 14/848,141, filed Sep. 8, 2015, 12 pages.
U.S. Non Final Office Action dated May 8, 2015, for U.S. Appl. No. 14/485,490, filed Sep. 12, 2014, 10 pages.
U.S. Non Final Office Action dated Nov. 12, 2020, for U.S. Appl. No. 15/791,700, filed May 4, 2018 16 pages.
U.S. Non Final Office Action dated Nov. 20, 2013, for U.S. Appl. No. 13/951,268, filed Jul. 25, 2013, 9 pages.
U.S. Non Final Office Action dated Oct. 25, 2010, for U.S. Appl. No. 12/556,640, filed Sep. 10, 2009, 9 pages.
U.S. Non Final Office Action dated Sep. 16, 2016, for U.S. Appl. No. 14/210,106, filed Mar. 13, 2014, 12 pages.
U.S. Non-Final Office Action dated Oct. 31, 2019, for U.S. Appl. No. 15/971,700, filed May 4, 2018, 19 pages.
U.S. Notice Of Allowance dated Apr. 26, 2013, for U.S. Appl. No. 12/556,640, filed Sep. 10, 2009, 6 pages.
U.S. Notice Of Allowance dated Dec. 14, 2006, for U.S. Appl. No. 10/269,916, filed Oct. 10, 2002, 6 pages.
U.S. Notice Of Allowance dated Dec. 16, 2016 for U.S. Appl. No. 14/848,141, filed Sep. 3, 2015, 7 pages.
U.S. Notice Of Allowance dated Jun. 11, 2014, for U.S. Appl. No. 13/951,268, filed Jul. 25, 2013, 13 pages.
U.S. Notice Of Allowance dated Jun. 19, 2007, for U.S. Appl. No. 10/269,916, filed Oct. 10, 2002, 3 pages.
U.S. Restriction Requirement dated Aug. 31, 2015 for U.S. Appl. No. 13/758,942, filed Feb. 4, 2013, 8 pages.
U.S. Restriction Requirement dated Feb. 12, 2015, for U.S. Appl. No. 14/210,106, filed Mar. 13, 2014, 6 pages.
U.S. Restriction Requirement dated Jul. 13, 2005, for U.S. Appl. No. 10/269,916, filed Oct. 10, 2002, 9 pages.
U.S. Restriction Requirement dated Nov. 20, 2014 for U.S. Appl. No. 13/981,885, filed Oct. 9, 2013, 11 pages.
U.S. Restriction Requirement dated Sep. 13, 2005, for U.S. Appl. No. 10/269,916, filed Oct. 10, 2002, 5 pages.
Veronese, F.M. (2001). "Peptide and Protein PEGylation: A Review Of Problems and Solutions," Biomaterials 22:405-417.

(56) References Cited

OTHER PUBLICATIONS

Wiese, K.G. (1993). "Osmotically Induced Tissue Expansion with Hydrogels: A New Dimension in Tissue Expansion? A Preliminary Report," Journal of Cranio-Maxillo-Facial Surgery 21:309-313.
Written Opinion dated Apr. 11, 2013 for PCT Patent Application No. PCT/US/13/24520 filed on Feb. 1, 2013, 6 pages.
Written Opinion dated Aug. 18, 2016, for PCT Patent Application No. PCT/US2016/17189, Internationally filed on Feb. 9, 2016, 6 pages.
Written Opinion dated Aug. 30, 2012, for PCT Application No. PCT/US2012/022920, filed on Jan. 27, 2012, 3 pages.
Wu, J.-T. et al. (2012) "Reactive Polymer Coatings: A General Route t Thiol-ene and Thiol-yne Click Reactions" Macromol. Rapid Commun. 33:922-927.
Wutticharoenwong, K. (Dec. 2007). "Bio-Based Reactive Diluents and Thiol-ene Photopolymerization for environmentally Benign Coatings," Dissertation presented to The Graduate Faculty of the University of Akron, 228 pages.
Xiang, Z. et al. (Sep. 2013; e-published on Aug. 4, 2013). "Adding an Unnatural Covalent Bond to Proteins Through Proximity-enhanced Bioreactivity," Nature Methods 10(9):885-888 (also includes the Erratum—Corrected after Print on Nov. 21, 2013), 6 pages.
Yan, J. et al. (Oct. 8, 2013). "Growing Hyperbranched Polymers Using Natural Sunlight," Scientific Reports 3(2841):1-7.
U.S. Final Office Action dated Jan. 28, 2019, for U.S. Appl. No. 15/549,787, filed Aug. 9, 2017, 15 pages.
U.S. Non-Final Office Action dated Sep. 21, 2018, for U.S. Appl. No. 15/549,787, filed Aug. 3, 2017, 22 pages.
U.S. Appl. No. 17/458,075, filed Aug. 26, 2021, by Alexei Kazantsev et al.
U.S. Appl. No. 17/491,108, filed Sep. 20, 2021, by Mariner Peter D. D. et al.

\* cited by examiner

A - cysteine

B - homocysteine

C – 2-amino-5-mercaptopentanoic acid

D – NHS-PEG-SH

E – N-succinimidyl-S-acetylthiopropionate (SATP)

F – N-acetyl homocysteine thiolactone

G – NHS-Norbornene

A- Polypeptide crosslinked polymer

B – Crosslinked polymer with pendant polypeptide

C – Polypeptide crosslinked polymer with pendant polypeptide

D – Derivatized polypeptide

E – Non-degradable polymer matrix with pendant releasable polypeptide

A – Consumption of thiol groups for free amino acids

B – Consumption of thiol groups for peptide amino acids

DEGRADABLE THIOL-ENE POLYMERS AND METHODS OF MAKING THEREOF

CROSS-REFERENCE TO RELATED APPLICATIONS

This application is a continuation application of U.S. patent application Ser. No. 15/549,787, now U.S. Pat. No. 10,912,837, which adopts the international filing date of Feb. 9, 2016, which is the U.S. national stage of International Application No. PCT/US2016/017189, filed internationally on Feb. 9, 2016, which claims the priority benefit of U.S. Provisional Patent Application No. 62/114,034, filed Feb. 9, 2015, the disclosures of which are incorporated herein by reference in their entireties.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 700032000701SEQLIST.TXT, date recorded: Jan. 25, 2021, size: 3 KB).

FIELD OF THE INVENTION

The invention is directed to methods for linking a polypeptide (including peptides and proteins) to another moiety using radical thiol-ene and thiol-yne chemistries, compositions comprising such linked polypeptides (for example, polypeptide conjugates and thiol-ene based biocompatible hydrogel polymers), and uses thereof in the biomaterials field.

BACKGROUND OF THE INVENTION

The biomaterials field has experienced a dramatic evolution over the past few decades. With the development of novel combinations of biomaterials, engineers have made great strides in creating polymeric materials to address today's unmet clinical needs. Classic chemistries that have been used to create these biomaterials have significant limitations, driving the field to identify new methods for building biocompatible biopolymers. The emergence of click chemistries has provided a mechanism to overcome some of the limitations of classic chemistries, but considerable development will be required before these reactions will be useful for biomedical engineering.

Radical-mediated thiol-ene and thiol-yne chemistries possess click-like properties, providing a versatile platform for a wide range of biomedical applications. The use of radical-mediated thiol-ene chemistry to form degradable polymers was first described in Bowman et al. in U.S. Pat. No. 7,288,608, which is hereby incorporated herein by reference. The use of radical-mediated thiol-yne chemistry is described in Anseth et al. in U.S. patent application Ser. No. 13/981,885, which is hereby incorporated herein by reference. It is generally thought that this uniquely mild chemistry can be used to create step-growth polymer networks in the presence of living cells and/or tissues. The term "bioorthogonal" is often used to describe chemistries such as the radical-mediated thiol-ene chemistry described herein, that do not alter biologically active components (cells, tissue, proteins, peptides) within the polymerization mixture. Materials based on thiol-ene chemistry have been demonstrated in a number of applications, including wound healing, cartilage repair, and cell and drug delivery.

In a recent paper, McCall and Anseth evaluated the activity of lysozyme and TGFβ when encapsulated in a hydrogel created by reacting PEG-norbornene with PEG-dithiol in a radical-mediated thiol-ene reaction. Results from this study indicated "that thiol-ene click reactions are capable of proceeding rapidly at low initiator concentrations with little to no impact on in situ protein bioactivity."

For many applications, it is useful to incorporate proteins or peptides into the polymer backbone. For example, in Anderson et al., norbornene functionalized four-arm PEG macromers were crosslinked with a cysteine flanked matrix metalloproteinase (MMP)-degradable peptide, to create a hydrogel network that is degraded by cell-secreted MMPs. Human mesenchymal stem cells encapsulated within this hydrogel appeared to maintain their activity and were able to proliferate. In another example, Mariner et al. encapsulated recombinant bone morphogenic protein (BMP) in a similar hydrogel without observing loss of BMP activity. Of note, while the crosslinking dicysteine-bearing oligopeptide was covalently attached to the polymer backbone in the last example, the BMP, which lacks free thiols, was not covalently attached to the hydrogel and no loss of biological activity of BMP2 was detected. These methods of incorporating or attaching peptides or proteins via a cysteine residue is commonly used and within the field is thought not to result in loss of activity of biological components that are either encapsulated or incorporated within the network.

However, we unexpectedly found that proteins encapsulated within a thiol-ene hydrogel formed from norbornene-functionalized four-arm PEG macromers crosslinked with a cysteine flanked MMP degradable peptide were substantially modified by this reaction—even when the minimum amount of radical initiator and exposure time required to polymerize the hydrogel was used. Thus, there remains a need for methods for incorporating or attaching proteins or peptides to polymers via thiol-ene chemistry that do not require the generation of high concentrations of damaging free radicals.

BRIEF SUMMARY OF THE INVENTION

Disclosed are compositions and methods for linking polypeptides (including peptides and proteins) to another moiety using radical-mediated thiol-ene chemistries, for example, by reacting a reactive thiol group attached to the polypeptide (having higher activity than a cysteine thiol group) with an olefin or alkyne compound under conditions that promote radical-mediated thiol-ene or thiol-yne reactions. Also provided are biomaterials produced by these methods, and uses thereof in the medical field.

In one aspect, the invention provides a method for linking a polypeptide (including peptides and proteins) comprising a peptide backbone and one or more reactive thiol groups comprising reacting the one or more reactive thiol groups with an olefin or alkyne compound under conditions that promote radical-mediated thiol-ene or thiol-yne chemistry, wherein the thiol group has a higher reactivity for undergoing a radical thiol-ene or thiol-yne reaction than a cysteine thiol group under similar conditions. In some embodiments, the reactive thiol group of the polypeptide has a reactivity at least 2 times, 5 times or 10 times greater than a cysteine thiol group. In some embodiments, the reactive thiol group of the polypeptide is separated from the peptide backbone by at least two carbon atoms. In some embodiments, the reaction is started by a radical initiator. In some embodiments, the reaction may be started by light. In some embodiments, the reaction may be performed in a reduced oxygen environment or in the absence of oxygen.

In one aspect, a method is provided for linking a polypeptide, wherein the polypeptide comprises a peptide backbone and one or more reactive thiol groups, comprising reacting a reactive thiol group of the polypeptide with a radical initiator and an ene compound comprising one or more reactive ene groups or an yne compound comprising one or more reactive yne groups, wherein the reactive thiol group of the polypeptide is separated from the peptide backbone of the polypeptide by two or more carbon atoms.

In some embodiments, the reactive thiol group of the polypeptide is a thiol group attached to the side chain amino group of a lysine residue via a linker, such as a PEG linker.

In some embodiments, the radical initiator is a photoinitiator selected from the group consisting of lithium phenyl-2,4,6-trimethylbenzoylphosphinate (LAP), sodium phenyl-2,4,6-trimethylbenzoylphosphinate (NAP), 2-hydroxy-1-[4-(2-hydroxyethoxy)phenyl]-2-methyl-1-propanone (e.g., Irgacure® 2959), 1-hydroxy-cyclohexyl-phenyl-ketone (e.g., Irgacure® 184) and 2,2-dimethoxy-1,2-diphenylethan-1-one (e.g., Irgacure® 651).

In some embodiments, the thiol-ene reaction is initiated by exposing the photoinitiator to a light having a wavelength matching the excitation wavelength of the photoinitiator.

In some embodiments, the method further comprises controlling the amount of the photoinitiator, the intensity of the light and/or the time the photoinitiator is exposed to the light.

In some embodiments, the method further comprises partially or wholly removing oxygen from the reaction mixture.

In some embodiments, the thiol-ene reaction reaches between about 70% completion and about 95% completion as measured, for non-limiting example, by rheology or by consumption of free thiol using Elman's assay. In other embodiments, the thiol-ene reaction reaches between about 70% completion and 100% completion. In other embodiments, the thiol-ene reaction reaches between about 95% completion and 100% completion.

In some embodiments, the polypeptide comprises two or more reactive thiol groups each separated from the peptide backbone of the polypeptide by two or more carbon atoms.

In some embodiments, the ene compound comprises two or more reactive ene groups.

In some embodiments, the polypeptide comprises n reactive thiol groups, the ene compound comprises m reactive ene groups, wherein n and m are independently an integer ≥2 and n+m≥5.

In some embodiments, the ene compound is an ene-modified biocompatible monomer and the thiol-ene reaction provides a biocompatible cross-linked polymeric matrix.

In a preferred embodiment, the ene compound is a norbornene-modified polyethylene glycol (PEG).

In some embodiments, the ene compound is an ene-modified non-biocompatible monomer and the thiol-ene reaction provides a non-biocompatible cross-linked polymeric matrix.

In some variations of previous embodiments, the polypeptide further comprises a peptide sequence known to be sensitive to a protease, such as a peptide degradable by a matrix metalloprotease. In another variation, the polypeptide is an active thiol-flanked plasmin degradable peptide. In yet another variation, two plasmin degradable sequences are included within the peptide. Other variations containing one or more enzymatically degradable sequences will understood by one skilled in the art.

In some embodiments, the thiol-ene reaction provides a biocompatible cross-linked degradable hydrogel polymer.

In some embodiments, the thiol-ene reaction provides a biocompatible cross-linked non-degradable hydrogel polymer.

In some embodiments, the thiol-ene reaction provides a non-biocompatible cross-linked degradable hydrogel polymer.

In some embodiments, the thiol-ene reaction provides a non-biocompatible cross-linked non-degradable hydrogel polymer.

In another aspect, the ene compound comprises one reactive ene group.

In some embodiments, the ene compound comprises a polymer (e.g., PEG), a capture moiety (e.g., biotin), a label (e.g., a fluorescent label), a carbohydrate, a nucleic acid, or a second polypeptide.

In other embodiments, the ene compound comprises a biological active component (e.g., a drug, a toxin or a pesticide).

In some embodiments, the polypeptide comprises one reactive thiol group separated from the peptide backbone of the polypeptide by two or more carbon atoms.

In some embodiments, the polypeptide is selected from peptide or protein hormones, growth factors, cytokines, interleukins, receptors, solubilized receptors, therapeutic proteins, enzymes and structural proteins.

In yet another aspect, the polypeptide comprises one reactive thiol group separated from the peptide backbone of the polypeptide by two or more carbon atoms, and the ene compound comprises two or more reactive ene groups.

In some embodiments, the ene compound comprises two or more reactive ene groups.

In some embodiments, the method further comprises reacting a second thiol compound with the ene compound comprising two or more reactive ene groups, wherein the second thiol compound comprises two or more reactive thiol groups. In some embodiments, the ene compound is a non-biocompatible ene compound. In some embodiments, the second thiol compound is a non-biocompatible thiol compound. In some embodiments, the ene compound is a non-degradable ene compound. In some embodiments, the second thiol compound is a non-degradable thiol compound.

In some embodiments, the second thiol compound comprises j reactive thiol groups, the ene compound comprises k reactive ene groups, wherein j and k are independently an integer ≥2 and j+k≥5.

In some variations, the second thiol compound comprises a polymeric moiety selected from the group consisting of poly(lactic acid) (PLA); polyglycolide (PGA); a copolymer of PLA and PGA (PLGA); poly(vinyl alcohol) (PVA); poly(ethylene glycol) (PEG); poly(ethylene oxide); a poly(ethylene oxide)-co-poly(propylene oxide) block copolymer; a poloxamine; a polyanhydride; a polyorthoester; a poly(hydroxy acids); a polydioxanone; a polycarbonate; a polyaminocarbonate; a poly(vinyl pyrrolidone); a poly(ethyl oxazoline); a polyurethane; a carboxymethyl cellulose; a hydroxyalkylated cellulose; a polypeptide; a nucleic acid; a modified nucleic acid; a locked nucleic acid; a polysaccharide; a carbohydrate; heparan sulfate; chondroitin sulfate; heparin, alginate; and a combination thereof.

In other variations, the second thiol compound comprises a peptide backbone, a degradable peptide and two or more reactive thiol groups each separated from the peptide backbone by two or more carbon atoms. In yet other variations, the second thiol compound comprises a peptide backbone, a non-degradable peptide and two or more reactive thiol groups each separated from the peptide backbone by two or more carbon atoms.

In other variations, the second thiol compound comprises a peptide sequence known to be sensitive to a protease and two homocysteine residues flanking the peptide sequence.

In other variations, the second thiol compound comprises a polyethylene glycol and two terminal thiol groups attached to the polyethylene glycol.

In some embodiments, the ene compound comprises a polymeric moiety selected from the group consisting of poly(lactic acid) (PLA); polyglycolide (PGA); a copolymer of PLA and PGA (PLGA); poly(vinyl alcohol) (PVA); poly(ethylene glycol) (PEG); poly(ethylene oxide); a poly (ethylene oxide)-co-poly(propylene oxide) block copolymer; a poloxamine; a polyanhydride; a polyorthoester; a poly(hydroxy acids); a polydioxanone; a polycarbonate; a polyaminocarbonate; a poly(vinyl pyrrolidone); a poly(ethyl oxazoline); a polyurethane; a carboxymethyl cellulose; a hydroxyalkylated cellulose; a polypeptide; a nucleic acid; a modified nucleic acid; a locked nucleic acid; a polysaccharide; a carbohydrate; heparan sulfate; chondroitin sulfate; heparin, alginate; and a combination thereof.

In a variation of all previous aspects the method further comprises producing the polypeptide comprising one or more reactive thiol groups.

In some embodiments of the previous variation, producing the polypeptide comprising one or more reactive thiol groups comprises polypeptide synthesis using a protected thiol-containing amino acid wherein the thiol group is separated from the carbon atom adjacent to the carboxy group by two or more carbon atoms, such as a protected homocysteine or 2-amino-5-mercaptopentanoic acid, or a protected thiol-containing amino acid analog or a protected thiol-containing amino acid mimetic.

In some embodiments of the previous variation, producing the polypeptide comprising one or more reactive thiol groups comprises modifying a polypeptide using a thiolating agent (e.g., by reacting an amino group in a peptide with a thiolating agent such as N-succinimidyl-3-(acetylthio)propionate (SATP), N-acetyl homocysteine thiolactone, or NHS-PEG-SH).

In some embodiments of the previous variation, producing the polypeptide comprising one or more reactive thiol groups comprises chemical or enzymatic conversion of a methionine residue in a polypeptide to a homocysteine residue.

Also disclosed herein is a linked polypeptide produced by a method according to any one of the previous aspects, embodiments and variations. In some embodiments, the linked polypeptide is linked to a biocompatible cross-linked polymeric matrix. In some embodiments, the linked polypeptide is linked to a non-biocompatible cross-linked polymeric matrix.

In another aspect, is disclosed a method for producing a biocompatible cross-linked degradable hydrogel polymer comprising reacting a reactive thiol compound with a radical initiator and a reactive ene compound, wherein the reactive thiol compound comprises a peptide backbone, a degradable peptide and two or more reactive thiol groups each separated from the peptide backbone by two or more carbon atoms; and the reactive ene compound is an ene-modified biocompatible monomer comprising two or more reactive ene groups. In some embodiments, the ene compound contains any suitable ethylenically unsaturated group such as, but not limited to, vinylacetyl, vinyl ester, vinylsulfonyl, vinyl ether, allyl, acrylate ester, methacrylate ester, acrylamido, maleimido, propenyl ether, allyl ether, alkenyl, unsaturated ester, dienyl, N-vinylcarbamoyl

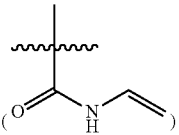 [SMILES: *C(=O)NC=C]

and norborn-2-en-5-yl

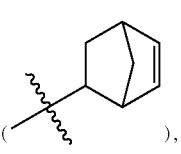 [SMILES: *C1CC2C=CC1C2]

or any combination thereof. In a preferred embodiment the ene compound is derivatized with a norbornene (e.g., norborn-2-en-5-yl) moiety. As is understood by a person of skill in the art, the ethylenically unsaturated group may be further substituted with one or more suitable substituents such as, for non-limiting example, halo, alkyl, alkoxy or oxo. In some embodiments, the reactive ene group of the ene compound may be selected from any suitable ethylenically unsaturated group such as, but not limited to, vinylacetyl, vinyl ester, vinylsulfonyl, vinyl ether, allyl, acrylate ester, methacrylate ester, acrylamido, maleimido, propenyl ether, allyl ether, alkenyl, unsaturated ester, dienyl, N-vinylcarbamoyl and norborn-2-en-5-yl, or any combination thereof. As is understood by a person of skill in the art, the reactive ene group of the ene compound may be further substituted with one or more suitable substituents such as, for non-limiting example, halo, alkyl, alkoxy or oxo. In some embodiments, the reactive ene group comprises a norbornene (e.g., norborn-2-en-5-yl) moiety. In some embodiments, the ene compound comprises one or more norbornene (e.g., norborn-2-en-5-yl) groups, such as a linear or branched PEG containing a norbornene moiety (e.g., norborn-2-en-5-yl) at each terminus. In some embodiments, the ene compound comprises two or more different ene groups, such as a PEG polymer comprising both a norbornene moiety (e.g., norborn-2-en-5-yl) and a vinyl ether moiety. In the case of a thiol-yne reaction in which a reactive thiol compound is reacted with an yne-modified biocompatible monomer the yne groups may be moieties such as ethynyl, propargyl, propiolate, cyclic alkynes and others, or any combination thereof.

In some embodiments, the method further comprises partially or wholly removing oxygen from the reaction mixture.

In some embodiments, the polypeptide comprises n reactive thiol groups, the ene compound comprises m reactive ene groups, wherein n and m are independently an integer $\geq 2$ and $n+m \geq 5$.

In some embodiments, the method further comprises adding a biologically active component to the reaction mixture, wherein the biologically active component is associated with (e.g., encapsulated in or covalently bound to (incorporated into or attached onto)) the polymer matrix of the biocompatible cross-linked degradable hydrogel polymer.

In some embodiments, the reactive thiol groups of the thiol compound are independently selected from a thiol group of a homocysteine residue of the polypeptide, a thiol group of a 2-amino-5-mercaptopentanoic acid residue of the polypeptide and a thiol group attached to the side chain amino group of a lysine residue via a linker.

In some embodiments, the radical initiator is a photoinitiator selected from the group consisting of lithium phenyl-2,4,6-trimethylbenzoylphosphinate (LAP), sodium phenyl-2,4,6-trimethylbenzoylphosphinate (NAP), 2-hydroxy-1-[4-(2-hydroxyethoxy)phenyl]-2-methyl-1-propanone (e.g., Irgacure® 2959), 1-hydroxy-cyclohexyl-phenyl-ketone (e.g., Irgacure® 184) and 2,2-dimethoxy-1,2-diphenylethan-1-one (e.g., Irgacure® 651).

In some embodiments, the reactive ene compound comprises a polymeric moiety selected from the group consisting of poly(lactic acid) (PLA); polyglycolide (PGA); a copolymer of PLA and PGA (PLGA); poly(vinyl alcohol) (PVA); poly(ethylene glycol) (PEG); poly(ethylene oxide); a poly(ethylene oxide)-co-poly(propylene oxide) block copolymer; a poloxamine; a polyanhydride; a polyorthoester; a poly(hydroxy acids); a polydioxanone; a polycarbonate; a polyaminocarbonate; a poly(vinyl pyrrolidone); a poly(ethyl oxazoline); a polyurethane; a carboxymethyl cellulose; a hydroxyalkylated cellulose; a polypeptide; a nucleic acid; a modified nucleic acid; a locked nucleic acid; a polysaccharide; a carbohydrate; heparan sulfate; chondroitin sulfate; heparin, alginate; and a combination thereof.

In some embodiments, the ene compound contains any suitable ethylenically unsaturated group such as, but not limited to, vinylacetyl, vinyl ester, vinylsulfonyl, vinyl ether, allyl, acrylate ester, methacrylate ester, acrylamido, maleimido, propenyl ether, allyl ether, alkenyl, unsaturated ester, dienyl, N-vinylcarbamoyl and norborn-2-en-5-yl, or any combination thereof. In a preferred embodiment the ene compound is a norbornene-derived compound such as an ene compound comprising a norborn-2-en-5-yl group. In some embodiments, the reactive ene group of the ene compound may be selected from any suitable ethylenically unsaturated group such as, but not limited to, vinylacetyl, vinyl ester, vinylsulfonyl, vinyl ether, allyl, acrylate ester, methacrylate ester, acrylamido, maleimido, propenyl ether, allyl ether, alkenyl, unsaturated ester, dienyl, N-vinylcarbamoyl and norborn-2-en-5-yl, or any combination thereof. In some embodiments, the reactive ene group is norborn-2-en-5-yl. As is understood by a person of skill in the art, the ethylenically unsaturated group may be further substituted with one or more suitable substituents such as, for non-limiting example, halo, alkyl, alkoxy or oxo. In some embodiments, the ene compound comprises one or more norborn-2-en-5-yl groups, such as a linear or branched PEG containing a norbornene moiety (e.g., norborn-2-en-5-yl) at each terminus. For thiol-yne reactions, the yne compound contains one or more alkyne groups such as one or more of ethynyl, propargyl, propiolate, cyclic alkynes and others, or any combination thereof.

In some embodiments, the biologically active component is a tissue, a cell, a protein, a peptide, a small molecule drug, a nucleic acid, an encapsulated nucleic acid (for example encapsulated in a lipid nanoparticle), a lipid, a carbohydrate, or an agricultural compound.

In some variations of the previous embodiments, the biologically active component is encapsulated in the polymer matrix of the biocompatible cross-linked degradable hydrogel polymer.

In other variations of the previous embodiments, the biologically active component is covalently bond to [e.g., incorporated into or attached onto] the polymer matrix of the biocompatible cross-linked degradable hydrogel polymer.

In other variations of the previous embodiments, the biologically active component is a biologically active polypeptide covalently bond to the polymer matrix via a thioether linkage formed by reacting a reactive thiol group of the biologically active polypeptide with an ene group, wherein the thio group of the thioether linkage is separated from the backbone of the biologically active polypeptide by two or more carbon atoms.

Also disclosed is a biocompatible cross-linked degradable hydrogel polymer produced by a method according to any one of the embodiments of the previous aspect.

Also disclosed is a biocompatible cross-linked degradable hydrogel polymer produced by a method according to any one of the embodiments of the previous aspect, further comprising a biologically active component associated with (e.g., encapsulated in or covalently bond to (incorporated into or attached onto)) the polymer matrix of the biocompatible cross-linked degradable hydrogel polymer.

As is understood by a person of skill in the art, in some variations, the methods of the previous aspect in any of its embodiments and variations can be applied with non-biocompatible and/or non-degradable ene compounds and/or non-biocompatible and/or non-degradable thiol compounds. Accordingly, also disclosed are non-biocompatible and/or non-degradable cross-linked hydrogel polymers produced by the methods of said variations.

Herein disclosed is a compound of formula (A):

P—[C$_t$—S—C—C-Q]$_x$ wherein P is a polypeptide, t≥2, C$_t$ is a linker comprising at least two carbon atoms [i.e., P is linked to one or more thioether moieties via a linker of two carbon atoms in length or longer], x is 1 or an integer greater than 1 [e.g. 2, 3, 4 or more] and Q is a biological active component [e.g., a drug, a toxin or a pesticide], a polymer [e.g., PEG], a capture moiety [e.g., biotin], a label [e.g., a fluorescent label], a carbohydrate, a nucleic acid, or a second polypeptide.

As is understood by a person of skill in the art, the C—C moiety between the sulfur atom and Q in formula A is a moiety resulting from the thiol-ene reaction of a reactive thiol group (the SH moiety of P—[C$_t$—SH]$_x$) and a reactive ene group (the —C=C— moiety of a Q bearing a suitable ethylenically unsaturated group). It is understood and described herein that the ethylenically unsaturated group (the —C=C— moiety) may be bound to Q directly or via a linker moiety, such as, for non-limiting example, an amide functionality, ester functionality or a combination thereof. It is further understood that the reactive ene group may be a terminal, unsubstituted ene group (e.g., CH$_2$=CH-Q) or may be substituted at one or more than one of the ethylenyl carbons, including substitutions in which the —C=C— moiety is part of a ring structure incorporating a double bond (e.g., a norbornene-derivatized Q or T-Q). It is further understood and described that the C$_t$ moiety of formula A is a linker of at least two atoms in length and that such a moiety may be unsubstituted or substituted.

In some embodiments, the compound of formula (A) is produced by reacting a compound of formula P—[C$_t$—SH]$_x$ and a compound of formula CH$_2$=CH-Q and a radical initiator, where P, C$_t$, x and Q are as defined for formula (A). In some embodiments, the compound of formula (A) is produced in a reduced oxygen environment or in the absence of oxygen.

In some embodiments, the compound of formula (A) in which the C—C moiety is derived from an alkene other than a terminal, unsubstituted alkene is also provided and may be produced by reacting a compound of formula P—[$C_t$—SH]$_x$ and a compound of formula T-Q and a radical initiator (such as a photoinitiator described herein), wherein P, $C_t$, t, Q and x are as defined for formula (A) and T indicates an alkene moiety other than a terminal, unsubstituted alkene moiety. In one aspect, T is a cyclic alkene moiety which can be a monocyclic or bicyclic cycloalkene, which can have up to two annular heteroatoms selected from O, S, and N, and which may be substituted, and where the bicyclic cycloalkene may be a fused, bridged or a spiro bicyclic ring. In some embodiments, T is comprises a norborn-2-en-5-yl group.

Also disclosed herein is a compound of formula (B):

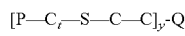

wherein P is a polypeptide, t≥2, $C_t$ is a linker comprising at least two carbon atoms [i.e., P is linked to the thioether moiety via a linker of two carbon atoms in length or longer], y is 1 or an integer greater than 1 [e.g. 2, 3, 4 or more] and Q is selected from the group consisting of poly(lactic acid) (PLA); polyglycolide (PGA); a copolymer of PLA and PGA (PLGA); poly(vinyl alcohol) (PVA); poly(ethylene glycol) (PEG); poly(ethylene oxide); a poly(ethylene oxide)-co-poly(propylene oxide) block copolymer; a poloxamine; a polyanhydride; a polyorthoester; a poly(hydroxy acids); a polydioxanone; a polycarbonate; a polyaminocarbonate; a poly(vinyl pyrrolidone); a poly(ethyl oxazoline); a polyurethane; a carboxymethyl cellulose; a hydroxyalkylated cellulose; a polypeptide; a nucleic acid; a modified nucleic acid; a locked nucleic acid; a polysaccharide; a carbohydrate; heparan sulfate; chondroitin sulfate; heparin, alginate; and a combination thereof.

As is understood by a person of skill in the art, the C—C moiety between the sulfur atom and Q in formula (B) is a moiety resulting from the thiol-ene reaction of a reactive thiol group (the SH moiety of P—$C_t$—SH) and a reactive ene group (the —C=C— moiety of a Q bearing a suitable ethylenically unsaturated group). It is understood and described herein that the ethylenically unsaturated group (the —C=C— moiety) may be bound to Q directly or via a linker moiety, such as, for non-limiting example, an amide functionality, ester functionality or a combination thereof. It is further understood that the reactive ene groups may be terminal, unsubstituted ene groups (e.g., [$CH_2$=CH]$_y$-Q) or may be substituted at one or more than one of the ethylenyl carbons, including substitutions in which the —C=C— moiety is part of a ring structure incorporating a double bond (e.g., a norbornene-derivatized Q). It is further understood and described that the $C_t$ moiety of formula (B) is a linker of two atoms in length and that such a moiety may be unsubstituted or substituted.

In some embodiments, the compound of formula (B) is produced by reacting a compound of formula P—$C_t$—SH and a compound of formula [$CH_2$=CH]$_y$Q and a radical initiator. P, $C_t$, y and Q are as defined for formula B. In some embodiments, the compound of formula (B) is produced in a reduced oxygen environment or in the absence of oxygen.

In some embodiments, the compound of formula (B) in which the C—C moiety is derived from an alkene other than a terminal, unsubstituted alkene is also provided and may be produced by reacting a compound of formula P—$C_t$—SH and a compound of formula [T]$_y$-Q and a radical initiator (such as a photoinitiator described herein), wherein P, $C_t$, t, Q and x are as defined for formula (B) and T indicates an alkene moiety other than a terminal, unsubstituted alkene moiety. In one aspect, T is a cyclic alkene moiety which can be a monocyclic or bicyclic cycloalkene, which can have up to two annular heteroatoms selected from O, S, and N, and which may be substituted, and where the bicyclic cycloalkene may be a fused, bridged or a spiro bicyclic ring. In some embodiments, T is comprises a norborn-2-en-5-yl group.

Also disclosed herein is a polymeric material [e.g. to a thiol-ene hydrogel] comprising repeating units of the formula (I):

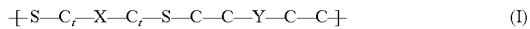

wherein X is a polypeptide, t≥2, $C_t$ is a linker comprising at least two carbon atoms [i.e., X is linked to at least two thioether moieties via a linker of two carbon atoms in length or longer], and Y is selected from the group consisting of poly(lactic acid) (PLA); polyglycolide (PGA); a copolymer of PLA and PGA (PLGA); poly(vinyl alcohol) (PVA); poly(ethylene glycol) (PEG); poly(ethylene oxide); a poly(ethylene oxide)-co-poly(propylene oxide) block copolymer; a poloxamine; a polyanhydride; a polyorthoester; a poly(hydroxy acids); a polydioxanone; a polycarbonate; a polyaminocarbonate; a poly(vinyl pyrrolidone); a poly(ethyl oxazoline); a polyurethane; a carboxymethyl cellulose; a hydroxyalkylated cellulose; a polypeptide; a nucleic acid; a modified nucleic acid; a locked nucleic acid; a polysaccharide; a carbohydrate; heparan sulfate; chondroitin sulfate; heparin, alginate; and a combination thereof.

In some embodiments, the polymeric material further comprises a biologically active component associated with (e.g., encapsulated in or covalently bond to (incorporated into or attached onto)) the polymer matrix of the polymeric material.

Also disclosed herein is a method for treating a condition or disorder in a subject (e.g. a human or an animal) in need thereof comprising administering a modified polypeptide; a biologically active component associated with (e.g., encapsulated in or covalently bond to (incorporated into or attached onto)) a biocompatible cross-linked degradable hydrogel polymer; a compound; or a biologically active component associated with (e.g., encapsulated in or covalently bond to (incorporated into or attached onto)) a polymeric material of previous aspects, embodiments and variations thereof.

Also disclosed herein is a method for regenerating tissue comprising releasing a cell or a tissue encapsulated in a biocompatible cross-linked degradable hydrogel polymer previous aspects at a site of damaged or defective tissue.

In some embodiments, the method further comprises producing a composition comprising the biocompatible cross-linked degradable hydrogel polymer at the site of damaged or defective tissue.

DETAILED DESCRIPTION OF THE INVENTION

Figure 1:
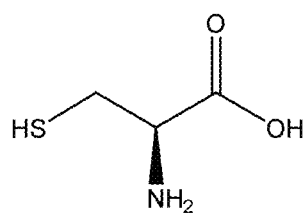
FIG. 1 shows representative structures of amino acids A) cysteine, B) homocysteine, C) 2-amino-5-sulfanylpentanoic acid, and thiolating agents D) HS-PEG-NHS, E) N-succinimidyl-S-acetylthiopropionate (SATP), F) N-acetyl homocysteine thiolactone, and G) NHS-Norbornene.
Figure 1:
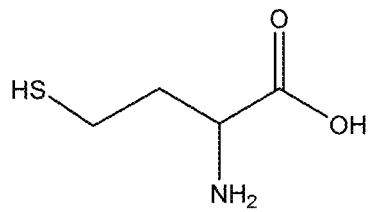
Figure 1:
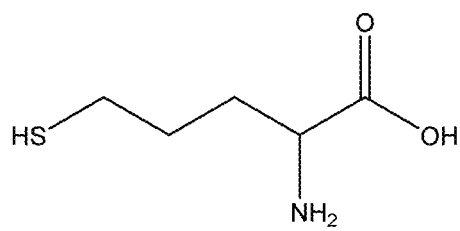
Figure 1:
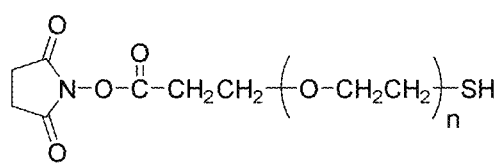
Figure 1:
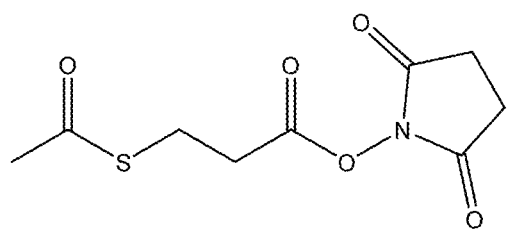
Figure 1:
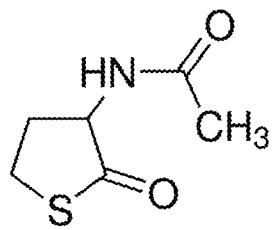
Figure 1:
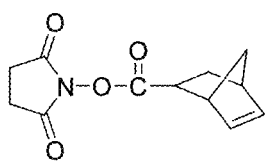

The invention provides compositions and methods for linking polypeptides (including peptides and proteins) to one or more other moieties using radical-mediated thiol-ene and thiol-yne chemistries. Some aspects of the methods comprise reacting a reactive thiol group attached to the polypeptide with an olefin or alkyne compound under conditions that promote radical-mediated thiol-ene or thiol-yne chemistry. The methods provide improved efficiency of coupling peptides and proteins to other moieties via radical-mediated thiol-ene or thiol-yne reactions compared to methods using cysteine thiols. The linked polypeptides produced using the methods, for example, protein and peptide conjugates and thiol-ene based biocompatible polymers are useful for treating human and animal diseases and as biomaterials for medical applications such as wound healing and tissue reconstruction.

The term "a" or "an" as used herein, unless clearly indicated otherwise, refers to one or more.

Reference to "about" a value or parameter herein includes (and describes) embodiments that are directed to that value or parameter per se. For example, description referring to "about X" includes description of "X".

Methods

One aspect of the invention provides a method for linking a polypeptide using radical-mediated thiol-ene or thiol-yne chemistries. Contrary to current teachings of current scientific and patent literature such as those references herein that considers thiol-ene reactions using a cysteine thiol group as a "bioorthogonal" method for linking polypeptides, we unexpectedly found that proteins encapsulated within a thiol-ene hydrogel formed from norbornene-functionalized four-arm PEG macromers crosslinked with a cysteine flanked MMP degradable peptide were substantially modified by this reaction—even when the minimum amount of radical initiator and exposure time required to polymerize the hydrogel was used. Further, we found that these same proteins were unmodified when encapsulated within a thiol-ene hydrogel formed from norbornene (e.g., norborn-2-en-5-yl) functionalized four-arm PEG macromers crosslinked with PEG-dithiol. The primary difference between the two experiments was that in the second case it was possible to fully polymerize the hydrogel using only one tenth (¹⁄₁₀) the amount of initiator as was used in the first case. This suggested that cysteine thiols in these peptides have a lower reactivity than the PEG thiols.

Surprisingly, we found that the reactivity of the reactive thiol for radical-mediated thiol-ene reactions can be enhanced by inserting one or more additional carbon atoms between the thiol group of a cysteine and the peptide backbone. For example, the reactivity of homocysteine, which has an additional carbon atom between the thiol and peptide backbone when compared to cysteine, is significantly enhanced when compared to cysteine. It will be appreciated that other compounds that similarly increase the distance between the thiol group and the peptide backbone will also enhance the activity of the thiol group. For example, the use of 2-amino-5-sulfanylpentanoic acid instead of cysteine adds an additional two carbon atoms between the thiol and the peptide backbone.

We also evaluated the ability of free cysteine to participate in a thiol-ene reaction. Surprisingly, free cysteine demonstrated substantially decreased activity relative to other small molecule thiols such as dithiothreitol, β-mercaptoethanol, homocysteine, cysteamine and 3-mercaptopropionic acid.

Together, these observations, which run contrary to current teachings in the field, suggest that the conditions required in order to use radical-mediated thiol-ene chemistry to react peptides with ene-containing moieties via cysteine residues within the peptide lead to the generation of high concentrations of damaging free radicals that can modify or otherwise damage biological active components contained within the reaction mixture. Thus, the often-cited property of radical-mediated thiol-ene chemistry, namely bioorthogonality, is not maintained under these conditions.

Using thiol groups with enhanced reactivities relative to cysteine thiols, lower concentrations of radical initiators are required for the reaction, lower concentrations of damaging free radicals are present in the reaction mixture, and/or shorter reaction time is needed to completion. The consequence of this finding is that using these enhanced thiols enables the desired property of bioorthogonality of thiol-ene reactions.

The use of homocysteine in radical-mediated thiol-ene or thiol-yne reactions has previously been described in a very limited context. In Yan et al. (2013), homocysteine was introduced into a non-peptide polymer through the use of prop-2-yn-1-yl-(2-oxotetrahydrothiophen-3-yl)carbamate. In a non-aqueous environment, aminolysis of prop-2-yn-1-yl(2-oxotetrahydrothiophen-3-yl)carbamate led to the formation of an alkyne-containing substituted homocysteine residue which could then polymerize through the reaction with the alkyne moiety of another molecule of this resulting compound or an alkene moiety of the generated polymer in the absence of a free-radical chemical initiator. Under the conditions used in this paper, this reaction proceeds to completion after irradiation with sunlight for cumulative 15 hours. In Espeel et al. (2011), homocysteine was introduced into a non-peptide polymer through the use of N-(allyloxy-carbonyl)homocysteine thiolactone. In a non-aqueous environment, aminolysis of N-(allyloxycarbonyl)homocysteine thiolactone led to the formation of an alkene-containing substituted homocysteine residue which could then polymerize through the reaction with the alkene moiety of another molecule of this resulting compound in the absence of a free-radical chemical initiator. Under the conditions used in this paper, this reaction proceeds to completion after irradiation with UV-light for 3 hours. The reactions described in Yan et al. and Espeel et al. proceeded relatively slowly and were performed in a non-aqueous environment using small monomers. Use of homocysteine in a thiol-ene reaction to preserve the activity of biologically active components encapsulated within an aqueous hydrogel has not been described previously.

Thus, in one aspect, provided is a method for linking a polypeptide, wherein the polypeptide comprises a peptide backbone and one or more reactive thiol groups, comprising reacting a reactive thiol group of the polypeptide with an ene compound comprising one or more reactive ene groups under conditions that promote a radical-mediated thiol-ene reaction. Also provided is a method for linking a polypeptide, wherein the polypeptide comprises a peptide backbone and one or more reactive thiol groups, comprising reacting a reactive thiol group of the polypeptide with an yne compound comprising one or more reactive yne groups under conditions that promote a radical-mediated thiol-yne reaction. The reactive thiol groups suitable for the methods of the invention are more reactive than a cysteine thiol group under conditions for radical thiol-ene or thiol-yne chemistries. In some embodiments, the reactive thiol group of the polypeptide has a reactivity for the radical-mediated thiol-ene reaction that is at least 2 times greater than that of a cysteine thiol group. In some embodiments, the reactive thiol group of the polypeptide has a reactivity for the radical-mediated thiol-ene reaction that is at least 3 times, at least 5 times, or at least 10 times greater than that of a cysteine thiol group. The relative reactivities of two thiol groups are the relative rate of the reaction for the thiol groups under identical reaction conditions, for example, as measured by the rate of consumption of the thiol groups (e.g., using Ellman's assay). In some embodiments, the relative reactivity means that under identical reaction conditions (for example in a photochemically initiated reaction identical concentrations of thiols, enes, and initiator, and identical wavelength and intensity of light are used) the reaction rate when using the reactive thiol group of the polypeptide will equal the reaction rate using a cysteine divided by the indicated value.

Thiol-ene reactions can be chemically or photochemically initiated. In some embodiments, the reaction is started by a radical initiator. In some instances, the reaction may be started by light (e.g., UV light or sun light) without an initiator compound. In a preferred embodiment, the radical initiator can be a photoinitiator compound. Any suitable photoinitiator may be used, such as those used by Bowman et al., for example the photoinitiators described in U.S. Pat. No. 7,288,608 and WO 2012/103445. In some embodiments, the photoinitiator is phenyl-2,4,6-trimethylbenzoylphosphinate (LAP) or sodium phenyl-2,4,6-trimethylbenzoylphosphinate (NAP). In some embodiments, the photoinitiator is 2-hydroxy-1-[4-(2-hydroxyethoxy)phenyl]-2-methyl-1-propanone (e.g., Irgacure® 2959), 1-hydroxy-cyclohexyl-phenyl-ketone (e.g., Irgacure® 184), or 2,2-dimethoxy-1,2-diphenylethan-1-one (e.g., Irgacure® 651).

The thiol-ene reactions typically are initiated by photolysis of the photoinitiator generating free radicals. Preferably, the wavelength of the light used is chosen to match the excitation wavelength of the photoinitiator. Thus in some embodiments, the thiol-ene reaction is initiated by exposing the photoinitiator to a light having a wavelength matching the excitation wavelength of the photoinitiator. In the case of LAP or NAP, the wavelength of the light is approximately 372 nm, with 360 nm or 380 nm being within acceptable range. In the case of 2-hydroxy-1-[4-(2-hydroxyethoxy) phenyl]-2-methyl-1-propanone (e.g., Irgacure® 2959), the wavelength of the light is approximately 276 nm or 331 nm. In the case of 1-hydroxy-cyclohexyl-phenyl-ketone (e.g., Irgacure® 184), the wavelength of the light is approximately 246 nm, 280 nm or 333 nm. In the case of 2,2-dimethoxy-1,2-diphenylethan-1-one (e.g., Irgacure® 651), the wavelength of the light is approximately 254 nm or 337 nm.

For optimal results, it is generally advised that the minimum photoinitiator amount and exposure time be chosen such that the thiol-ene reaction reaches (or nearly reaches) a desired completion. In particular embodiments the exposure time is chosen so the thiol-ene or thiol-yne reaction reaches less than 100% completion, for example about 98%, about 95%, about 90%, about 80%, or about 70% completion. This prevents excess radical damage to other components of the reaction mixture. In one embodiment of the current invention, network formation is monitored by rheology as a function of light intensity, exposure time, and initiator concentration. In another embodiment, the reaction is monitored via the consumption of free thiol using Elman's assay. In addition to rheology and thiol consumption, other methods of monitoring the reaction will be clear to those skilled in the art.

Thus in some embodiments, the method of linking a polypeptide using the thiol-ene chemistry further comprises controlling the amount of the photoinitiator, the intensity of the light and/or the time the photoinitiator is exposed to the light. In some instances, it may be desirable to allow the reaction to proceed to a point where the thiol-ene reaction is not 100% complete, but a certain goal is essentially achieved without allowing inducing substantial damage to other components of the reaction mixture. For instance, photo-induced polymerizations are often performed with relatively high concentrations of photoinitiator in order to ensure that a reasonably high rate of photopolymerization is achieved. In such instances, not all initiator is required to drive the reaction to 100% completion. For such cases, 100% complete thiol-ene reaction would completely exhaust thiol-ene reactants that afford protective effects from free radicals arising from photolysis of initiator, thus resulting in damage to the biologically active cargo. For these cases, a reasonable compromise between reaction completeness and cargo integrity can be easily found by driving the thiol-ene reaction to less than 100%. For an ad hoc example, driving a thiol-ene photopolymerization reaction under certain conditions to only 90% would result in a formation of a hydrogel with predictable mechano-elastic properties, while providing sufficient protection to an encapsulated biologically active cargo by virtue of remaining 10% thiols or enes. For example, in one embodiment, the photoinitiator is 0.01 wt. % LAP or 0.01 wt. % NAP, and the reaction mixture is subject to 19 mW/cm$^2$ 380 nm light for 10 seconds. In some embodiments, the thiol-ene reaction reaches greater than (lower limit) about 70%, 80%, 90%, 95%, or 98% completion. In some embodiments, the thiol-ene reaction reaches less than (upper limit) about 99.99%, 99.9%, 99.5%, 99%, 98%, 97%, 96%, 95%, 90% or 85%. That is the desired completion of the thiol-ene reaction can be any of a range of completions from about 70% to about 99.99% in which the lower limit is less than the upper limit. In some embodiments, the thiol-ene reaction reaches between about 70% completion and about 95% completion.

The thiol-ene or thiol-yne reactions may be carried out in any suitable media or solvents. However, in reactions involving proteins and other water soluble biomaterials, an aqueous media may be advantageous. Thus in some preferred embodiments, the method for linking a polypeptide using radical-mediated thiol-ene chemistry comprises reacting the reactive thiol group with the ene/yne compound in an aqueous environment or an aqueous medium. It is appreciated that the methods may produce a hydrogel comprising a polymer matrix, e.g., when the reactions are carried out in the presence of an aqueous solvent.

Typically, aqueous solutions in equilibrium with atmosphere contain about 200 μM concentration of dissolved oxygen, which is a known inhibitor of many radical-mediated reactions. Radical-mediated thiol-ene polymerization, however, has so far been considered to be insensitive to oxygen-mediated inhibition. The reported insensitivity of radical-mediated thiol-ene reactions to oxygen inhibition has been described in many publications, (see, for example, McCall, J. D., and Anseth, K. S., 2012., as well as Hoyle, C. E., Lee, T. Y. and Roper, T. 2004). However, it was unexpectedly found that at concentrations of norbornenes and thiols that are relevant for rapid biopolymer formation, for example, reactive thiol group and reactive ene group concentrations each between 1 mM and 50 mM, oxygen presents an inhibitory effect and that this can be bypassed by removing oxygen from the reactant solution. Therefore, in one aspect is provided a method for increasing the rate of reaction of a radical-mediated thiol-ene reaction by reducing exposure of the reaction to dissolved oxygen (e.g., by carrying out the reaction in a reduced oxygen environment). It is understood that carrying out a radical-mediated thiol-ene reaction in a reduced oxygen environment increases the rate of reaction and therefore can reduce unwanted side reactions for any thiol compound/ene compound pair, including a cysteine/norbornene pair and a homocysteine/norbornene pair. In one aspect, provided is a method for reducing radical mediated byproducts of a radical mediated thiol-ene reaction by carrying out the reaction under a reduced oxygen environment, such as by reacting a thiol compound and an ene compound in a degassed solution under conditions suitable for a radical-mediated thiol-ene reaction. In some embodiments, the thiol compound comprises a reactive thiol group wherein the reactive thiol group is the thiol group of a cysteine residue. In some embodiments, the thiol compound comprises a reactive thiol group wherein the reactive thiol group is the thiol group of a homocysteine residue. In some embodiments, the ene compound comprises one or more norborn-2-en-5-yl moieties. In a particular aspect, the thiol-ene reaction is carried out in a degassed solution, where the concentration of reactive thiol group is from 1 mM to 50 mM and the concentration of the reactive ene group is equal to or reasonably close to the concentration of reactive thiol group. In some variations, the reactive thiol group and reactive ene group concentrations are each between 1 mM and 50 mM. In some variations, the reactive thiol group and reactive ene group concentrations are each between 1 mM and 40 mM. In some variations, the reactive thiol group and reactive ene group concentrations are each between 1 mM and 30 mM. In some variations, the reactive thiol group and reactive ene group concentrations are each between 1 mM and 20 mM. In some variations, the reactive thiol group and reactive ene group concentrations are each between 1 mM and 10 mM. In some variations, the reactive thiol group and reactive ene group concentrations are each between 10 mM and 50 mM. In some variations, the reactive thiol group and reactive ene group concentrations are each between 20 mM and 50 mM. In some variations, the reactive thiol group and reactive ene group concentrations are each between 30 mM and 50 mM. In some variations, the reactive thiol group and reactive ene group concentrations are each between 40 mM and 50 mM.

The thiol-ene or thiol yne reactions may be carried out in a reduced oxygen environment, such as in the absence of oxygen or in the presence of a reduced amount of oxygen compared to a thiol-ene reaction in which no efforts are made to reduce exposure of the reaction to oxygen. For example, the reaction solution can be degassed prior to initiating the reaction by methods commonly applied in the art. In some embodiments, the method for linking a polypeptide using radical-mediated thiol-ene chemistry comprises removing oxygen from the reaction medium.

In some embodiments, the ene compound is a non-biocompatible ene compound. In some embodiments, the thiol compound is a non-biocompatible thiol compound. In some embodiments, the ene compound is a non-degradable ene compound. In some embodiments, the thiol compound is a non-degradable thiol compound.

Reactive Thiol-Containing Polypeptides

The reactive thiol group of the polypeptide suitable for the methods of the invention is more reactive toward radical-mediated thiol-ene reactions that a cysteine thiol group, which is separated from the peptide backbone by one carbon atom. In some embodiments, the reactive thiol group of the polypeptide is separated from the peptide backbone of the polypeptide by two or more carbon atoms. In some embodiments, the polypeptide contains one or more of the reactive thiol groups. In some embodiments, a polypeptide is modified to introduce one or more reactive thiol groups suitable for the method of this invention. In some embodiments, a polypeptide is modified to replace a cysteine residue with a rare amino acid, an unnatural amino acid, an amino acid analog or an amino acid mimetic. Non-limiting examples of reactive thiol groups which can be incorporated into polypeptides are illustrated in Table 1 below. Side chain modified amino acid residues in Table 1 illustrate amino acid residues that are suitable for incorporating into, or are present in, a polypeptide and which react with reactive ene group in a radical-mediated thiol-ene reaction. Such side chain modified amino acid residues have the desired property of having an extended alkanediyl moiety (which may include one or more additional linker groups such as, for non-limiting example, an amide and/or PEG moiety) between the polypeptide backbone and the thiol group as compared to cysteine. Without being bound by any theory, the extended alkanediyl moiety is believed to destabilize the thiol radical as compared to a radical formed from a cysteine thiol, resulting in an increase in the free-radical mediated thiol-ene reaction rate as compared to using a cysteine thiol. An increased reaction rate is beneficial and has significant implications, such as a reduced amount or extent of radical mediated side reactions, a decrease in damage to tissue or other biological products, enhanced selectivity for the peptide for which modification is desired (by decreasing the incidence of modification of endogenous cysteines) and a more rapid treatment protocol in a patient setting (e.g., reducing the time for the reaction to be complete by about 5-50 fold, such as from 90 seconds with a cysteine-based thiol to 2-10 seconds with the side chain modified amino acids). Backbone modified amino acid residues of Table 1 (e.g., β-amino acid residues, γ-amino acid residues, amino acid analogs and amino acid mimetics) illustrate amino acid residues that are suitable for incorporating into polypeptide and whose thiol moiety may react with an reactive ene group in a radical-mediated thiol-ene reaction. Such backbone modified amino acid residues are also believed to be useful in increasing the overall reaction rate of a thiol-ene reaction as compared to an unmodified polypeptide backbone, and are expected to exhibit the same beneficial properties as the side chain modified amino acid residues, such as reduced side reactions, greater selectivity and rapid treatment protocols.

TABLE 1

Exemplary reactive thiol groups

Side chain modified amino acid residues (P[Ct—SH]x

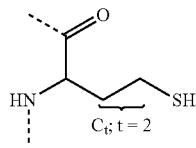

Homocysteine residue

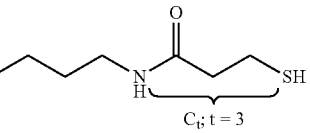

(3-mercaptopropanoyl)-modified lysine residue

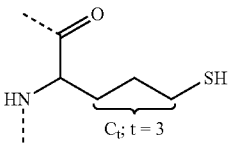

2-amino-5-mercaptopentanoic acid residue

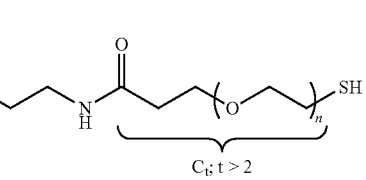

(3-mercaptopropanoyl)-modified lysine residue

Backbone modified amino acid residue

β-amino acid residues

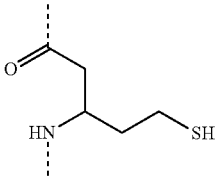

5-mercapto-3-aminopentanoic acid residue

TABLE 1-continued

Exemplary reactive thiol groups

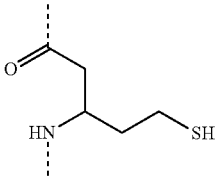

4-mercapto-2-(aminomethyl)butanoic acid residue

γ-amino acid residues

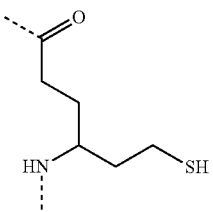

6-mercapto-4-aminohexanoic acid residue

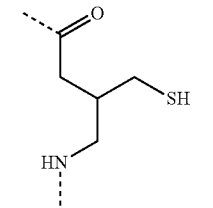

4-mercapto-3-(aminomethyl)butanoic acid residue

Amino acid analogs and amino acid mimetics

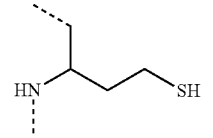

deoxygenated amino acid mimetic residue

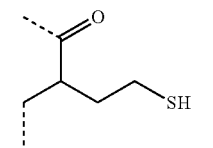

deaminated amino acid mimetic residue

Dashed lines represent attachment to the remainder of the polypeptide or protein chain.

As further illustrated in the Examples section below, there are a number of methods for incorporating a thiol into a peptide such that there are one or more carbon atoms between the peptide backbone and the thiol. These methods include, but are not limited to: 1) Peptide synthesis using a protected amino acid where there are two or more carbon atoms separating the thiol from the 2-position carbon atom (what will be peptide the backbone). Examples of such protected amino acids include, but are not limited to, Fmoc-protected building blocks (S)-2-(Fmoc-amino)-4-tritylsulfanyl-butyric acid (Bachem) or (S)-Fmoc-2-amino-5-(tritylthio)-pentanoic acid (PolyPeptide); 2) Modification of a peptide using a thiolating agent. Examples of such thiolating agents include, but are not limited to, N-succinimidyl-S- acetylthiopropionate (SATP), N-acetyl homocysteine thiolactone, and NHS-PEG-SH; 3) conversion of methionine to homocysteine by a methyl transferase reaction.

Figure 2:
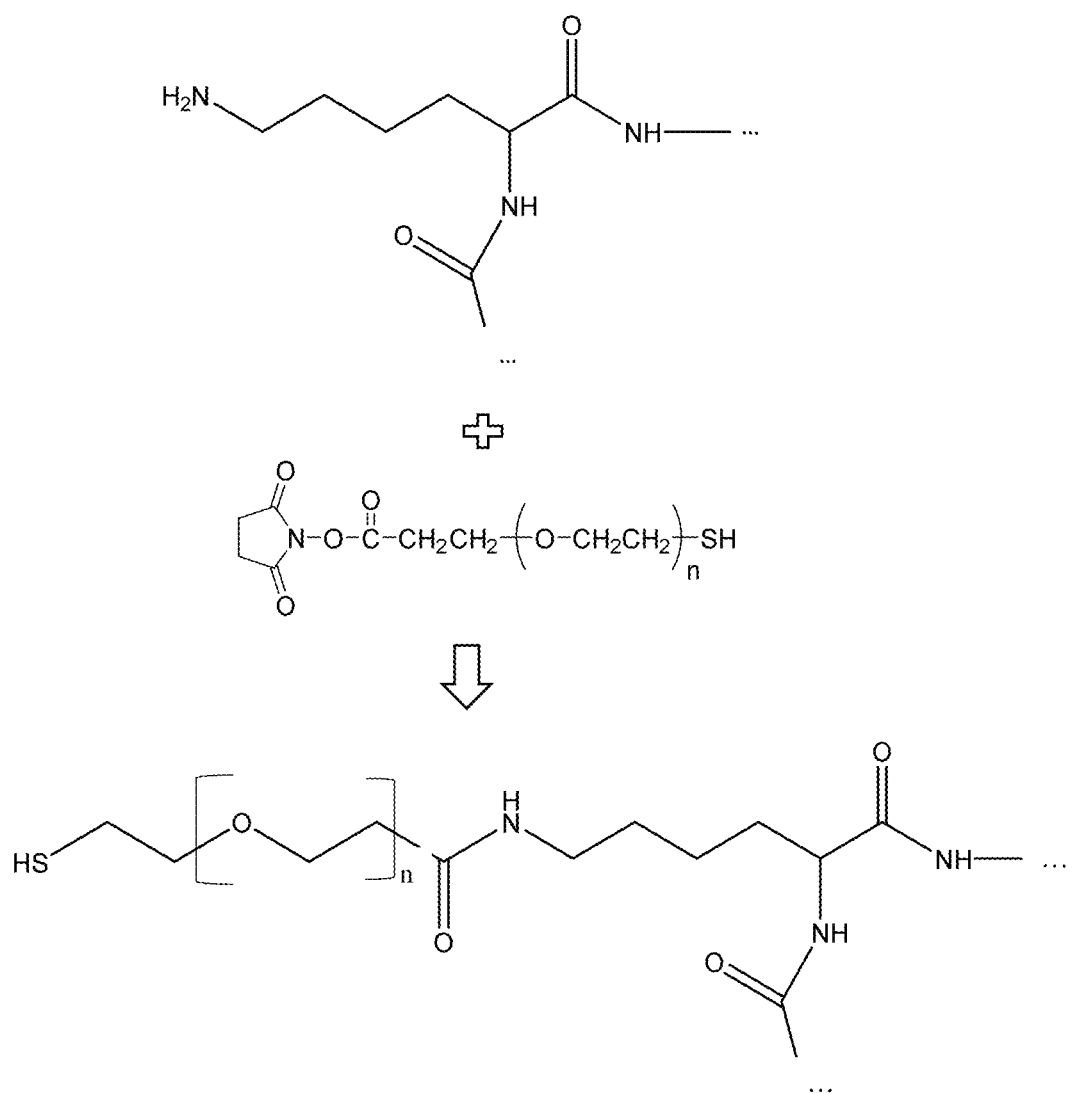
FIG. 2 shows the scheme for adding a reactive thiol group via HS-PEG-NHS modification of a lysine residue.

In some embodiments, the reactive thiol group of the polypeptide is a thiol group of a homocysteine residue of the polypeptide or a thiol group of a 2-amino-5-mercaptopentanoic acid residue of the polypeptide. Polypeptides containing homocysteine or 2-amino-5-mercaptopentanoic acid residues can be made using peptide synthesis methods known in the art, such as methods described herein. FIG. 2 illustrates the incorporation of a reactive thiol group to the side chain of a lysine residue using NHS-PEG-SH as a thiolating agent.

In some embodiments, the reactive thiol group of the polypeptide is a thiol group attached to the side chain amino group of an amino group (e.g., side chain amino group of a lysine residue or the N-terminal amino group) via a linker. The reactive thiol group of the polypeptide can be attached to the side chain amino group of a lysine using a thiolating agent. Examples of such thiolating agents include, but are not limited to, N-succinimidyl-S-acetylthiopropionate (SATP), N-acetyl homocysteine thiolactone, and NHS-PEG-SH.

Some embodiments of the method for linking a polypeptide further comprises producing the polypeptide comprising one or more reactive thiol groups prior to subjecting the reactive thiol groups to conditions that promote radical-mediated thiol-ene or thiol-yne reactions. In some embodiments, the method comprises polypeptide synthesis using a protected thiol-containing amino acid wherein the thiol group is separated from the carbon atom adjacent to the carboxy group by two or more carbon atoms, for example without limitation, a protected homocysteine (e.g., (S)-2-(Fmoc-amino)-4-tritylsulfanyl-butyric acid) or 2-amino-5-mercaptopentanoic acid (e.g., (S)-Fmoc-2-amino-5-(tritylthio)-pentanoic acid). In some embodiments, the method comprises modifying a polypeptide using a thiolating agent, for example, reacting an amino group in a peptide with a thiolating agent such as N-succinimidyl-3-(acetylthio)propionate (SATP), N-acetyl homocysteine thiolactone, or NHS-PEG-SH. In some embodiments, the method comprises chemical or enzymatic conversion of a methionine residue in a polypeptide to a homocysteine residue, for example, by a methyl transferase reaction.

In some embodiments, the reactive thiol group of the polypeptide is a thiol group attached to an unnatural amino acid such as a thiol substituted beta amino acid, a thiol substituted gamma amino acid, a thiol substituted delta amino acid or a thiol substituted epsilon amino acid. Polypeptides comprising thiol substituted beta amino acid, thiol substituted gamma amino acid, thiol substituted delta amino acid or thiol substituted epsilon amino acid residues can be made using peptide synthesis methods known in the art, such as methods described herein.

In some embodiments, the reactive thiol group of the polypeptide is a thiol group attached to an amino acid analog or an amino acid mimetic residue. In some embodiments, the amino acid analog or amino acid mimetic residue is derived from a natural amino acid, a rare amino acid or unnatural amino acid in which the carbonyl functionality is replaced by a methylene moiety or a longer carbon chain, optionally interspersed with one or more heteroatoms selected from oxygen, sulfur and nitrogen. In some embodiments, the amino acid analog or amino acid mimetic residue is derived from a natural amino acid, a rare amino acid or unnatural amino acid in which the amino functionality is replaced by a methylene moiety or a longer carbon chain, optionally interspersed with one or more heteroatoms selected from oxygen, sulfur and nitrogen.

In some variations of the previous embodiments, the thiol compound is a non-biocompatible thiol compound. In other variations of the previous embodiments, the thiol compound is a non-biocompatible thiol compound. In some variations of the previous embodiments, the thiol compound is a degradable thiol compound. In other variations of the previous embodiments, the thiol compound is a non-degradable thiol compound.

The method of the invention for linking a polypeptide may be used to link a protein or peptide to a second moiety, for example, to carry a biologically active component (such as those described herein), or to provide additional properties to the polypeptide, such as a polymer to extend the in vivo circulating half-life (such as PEG), an affinity tag such as biotin, an antibody, an aptamer (or other capture moiety or tag) to provide a capture function, a label (such as a fluorescent label, a chromophore, or a fluorophore), a sugar or other carbohydrate, a nucleic acid, a ribonucleoprotein, another polypeptide, a lipid or another hydrophobic moiety, an nanoparticle, a nanotube or a higher-order macromolecular assembly.

A variety of polypeptides may be modified using the method of the invention. In certain embodiments, the polypeptide can be selected from peptide and protein hormones, growth factors, cytokines, interleukins, receptors, solubilized receptors, therapeutic proteins, enzymes, and structural proteins. Growth factors may include AM, Ang, BMP, BDNF, GDNF, GCSF, GM-CSF, GDF, HGF, HDGF, KGF, MSF, NGF, TPO, FBS, EPO, IGF, EGF, FGF, TGF, PDGF and interleukins including their derivatives and family members. Structural proteins include fibrin, fibrinogen, fibronectins, keratins, actins, laminins and collagens.

The method of the invention may also be used to incorporate a degradable peptide into a thiol-ene or thiol-yne based hydrogel polymers. In some embodiments, the polypeptide further comprises a peptide sequence known to be sensitive to a protease. In another embodiment, the polypeptide is an active thiol-flanked plasmin degradable peptide. In another embodiment, two plasmin degradable sequences are included within the peptide. In a particular embodiment, the polypeptide is a homocysteine-flanked matrix metalloproteinase (MMP) degradable peptide, to create a hydrogel network that is degraded by cell-secreted MMPs.

In some embodiments, the method uses a polypeptide (including peptides and proteins) comprising one reactive thiol group separated from the peptide backbone of the polypeptide by two or more carbon atoms. In some embodiments, the polypeptide (including peptides and proteins) comprises two or more reactive thiol groups each separated from the peptide backbone of the polypeptide by two or more carbon atoms. In some embodiments, the polypeptide (including peptides and proteins) comprises two reactive thiol groups each separated from the peptide backbone of the polypeptide by two or more carbon atoms. In some embodiments, the polypeptide (including peptides and proteins) comprises three or four or more reactive thiol groups each separated from the peptide backbone of the polypeptide by two or more carbon atoms. In some embodiments, the reactive thiol group is a thiol group of a homocysteine residue, a thiol group of a 2-amino-5-mercaptopentanoic acid residue, or a thiol group attached to the side chain amino group of a lysine residue via a linker (e.g., a PEG linker).

Ene/yne-Containing Compounds

The ene compound or yne compound useful in the method of the invention can be any ene compound or yne compound suitable for radical-mediated thiol-ene or thiol-yne chemistries, such as a compound which contains an alkene or alkyne group that is reactive under radical thiol-ene or thiol-yne conditions ("a reactive ene group" or "a reactive yne group"). The ene compound (or ene-containing compound) comprise the reactive ene groups and an ene-bearing moiety which constitutes the scaffold carrying the reactive ene groups. A list of appropriate ene compounds, including an indication of their relative reaction rates can be found in Hoyle et al (2004) "Thiol-enes: Chemistry of the past with promise for the future" which is hereby incorporated by reference. The yne compound (or yne-containing compound) comprises the reactive yne groups and an yne-bearing moiety which constitutes the scaffold carrying the reactive yne groups.

In some variations of the previous embodiments, the ene compound is a non-biocompatible ene compound. In other variations of the previous embodiments, the ene compound is a non-biocompatible ene compound. In some variations of the previous embodiments, the ene compound is a degradable ene compound. In other variations of the previous embodiments, the thiol compound is a non-degradable ene compound.

In some embodiments, the ene compound contains any suitable ethylenically unsaturated group such as, but not limited to, vinylacetyl, vinyl ester, vinylsulfonyl, vinyl ether, allyl, acrylate ester, methacrylate ester, acrylamido, maleimido, propenyl ether, allyl ether, alkenyl, unsaturated ester, dienyl, N-vinylcarbamoyl and norborn-2-en-5-yl. In a preferred embodiment the ene compound comprises a norborn-2-en-5-yl group. In some embodiments, the reactive ene group of the ene compound may be selected from any suitable ethylenically unsaturated group such as, but not limited to, vinylacetyl, vinyl ester, vinylsulfonyl, vinyl ether, allyl, acrylate ester, methacrylate ester, acrylamido, maleimido, propenyl ether, allyl ether, alkenyl, unsaturated ester, dienyl, N-vinylcarbamoyl and norborn-2-en-5-yl. In some embodiments, the reactive ene group is norborn-2-en-5-yl. In some embodiments, the ene compound comprises one or more norborn-2-en-5-yl groups. As is understood by a person of skill in the art, the ethylenically unsaturated group may be further substituted with one or more suitable substituents such as, for non-limiting example, halo, alkyl, alkoxy or oxo. The yne compound contains one or more alkyne groups such as ethynyl, propargyl, propiolate, cyclic alkynes and others.

Non-limiting examples of reactive ene groups and their corresponding thiol-ene reaction product are illustrated in Table 2, where dashed lines indicate a point of attachment.

TABLE 2

Exemplary reactive ene groups and corresponding thiol-ene reaction products

| Reactive ene group | Corresponding Thiol-ene product |
|---|---|
| vinylacetyl | |
| vinylsulfonyl | |
| vinyl ether | |
| allyl | |
| acrylate ester | |
| methacrylate ester | |
| acrylamido | |
| maleimido | |
| propenyl ether | |
| allyl ether | |
| alkenyl | |
| N-vinyl carbamoyl | |

TABLE 2-continued

Exemplary reactive ene groups and
corresponding thiol-ene reaction products

| Reactive ene group | Corresponding Thiol-ene product |
|---|---|
| 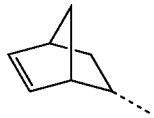 norborn-2-en-5-yl | 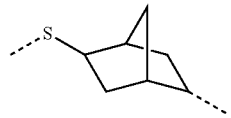 |

As is understood by a person skilled in the art, the sulfur atom of the reactive thiol group can be linked to either terminus of the carbon-carbon double bond of the reactive ene group. As is also understood by a person skilled in the art, the thiol-ene reaction can occur on either face of the planar carbon-carbon double bond of the reactive ene group. As a result, the product of the thiol-ene reaction can exhibit positional isomerism (attack on different carbon atoms of the carbon-carbon double bond) as well as stereoisomerism (attack on different faces of the carbon-carbon double bond). It is understood that all possible products are encompassed by the present invention. As is further understood by a person of skill in the art, an ene compound comprising more than one reactive ene group and having identical reactive ene groups can give rise to product wherein individual reactive ene groups may have reacted differently. For non-limiting example, a PEG dinorbornene (an ene compound with two norborn-2-en-5-yl reactive groups) may give rise to a product wherein one norbornene moiety (e.g., norborn-2-en-5-yl) gave rise to a thioether bond wherein the sulfur is 5-exo, and the other norbornene moiety (e.g., norborn-2-en-5-yl) gave rise to a thioether bond wherein the sulfur is 6-endo. It will be understood that such variations are also encompassed by the present invention.

The ene/yne-bearing moiety of the ene/yne compound is covalently linked to the reactive thiol-containing polypeptide by the radical-mediated thiol-ene or thiol-yne reaction of the invention. The ene/yne-bearing moiety can be chosen with respect to the specific functional property that the linking is sought to confer, for a non-limiting example, introduction of a fluorophore or chromophore, introduction of an affinity tag, introduction of enzymatic activity, introduction of a certain chemical moiety or moieties, introduction of a hydrophilic, hydrophobic or amphiphilic polymeric tail in order to manipulate solubility, pharmacokinetics, pharmacodynamics or interaction with biological membranes or solid surfaces, generation of a protein-containing polymer or of a telechelic monomer for further polymerization etc. The ene-bearing moiety may include appropriate derivatives of the following (non-limiting example): poly(lactic acid) (PLA), polyglycolide (PGA), copolymers of PLA and PGA (PLGA), poly(vinyl alcohol) (PVA), poly(ethylene glycol) (PEG), poly(ethylene oxide), poly(ethylene oxide)-co-poly(propylene oxide) block copolymers (poloxamers, meroxapols), poloxamines, polyanhydrides, polyorthoesters, poly(hydroxy acids), polydioxanones, polycarbonates, polyaminocarbonates, poly(vinyl pyrrolidone), poly(ethyl oxazoline), a polyurethane, carboxymethyl cellulose, hydroxyalkylated celluloses such as hydroxyethyl cellulose and methylhydroxypropyl cellulose, and natural polymers such as polypeptides, nucleic acids, polysaccharides or carbohydrates such as polysucrose, hyaluronic acid, dextran and similar derivatives thereof, heparan sulfate, chondroitin sulfate, heparin, or alginate, and proteins such as gelatin, collagen, albumin, or ovalbumin, fibrinogen, fibrin, laminin, fibronectin, vitronectin, fluorescent proteins such as green fluorescent protein or its analogs, fluorescent and non-fluorescent dyes, fluorescence quenchers, high-affinity tags, such as polypeptide tags (His-tag, FLAG-tag and others), antibodies and fragments thereof, nucleic acid aptamers, oligonucleotides and polynucleotides, high-order macromolecular assemblies such as ribonucleoproteins, viral capsids etc. The ene-bearing moiety may also include nucleic acids containing any known modifications ("a modified nucleic acid"), such as nucleic acids incorporating modified bases (e.g. modifications at one or more positions on a base, including the 2' and 5 position), and locked nucleic acids.

In some embodiments, the ene/yne compound comprises an ene/yne-bearing moiety selected from the group consisting of poly(lactic acid) (PLA); polyglycolide (PGA); a copolymer of PLA and PGA (PLGA); poly(vinyl alcohol) (PVA); poly(ethylene glycol) (PEG); poly(ethylene oxide); a poly(ethylene oxide)-co-poly(propylene oxide) block copolymer; a poloxamine; a polyanhydride; a polyorthoester; a poly(hydroxy acids); a polydioxanone; a polycarbonate; a polyaminocarbonate; a poly(vinyl pyrrolidone); a poly(ethyl oxazoline); a polyurethane; a carboxymethyl cellulose; a hydroxyalkylated cellulose; a polypeptide; a nucleic acid; a modified nucleic acid, a locked nucleic acid, a polysaccharide; a carbohydrate; heparan sulfate; chondroitin sulfate; heparin, alginate; and a combination thereof.

In some embodiments, the ene/yne-bearing moiety may comprise a biologically active component. In some embodiments, the ene/yne-bearing moiety may comprise a second moiety, which when linked to the polypeptide can provide additional properties to the polypeptide, such as a polymer to extend the in vivo circulating half-life (such as PEG), a biotin (or other capture moiety or tag) to provide a capture function, a label (such as a fluorescent label, a chromophore, or a fluorophore), a sugar or other carbohydrate, a nucleic acid, another polypeptide. In some embodiments, the ene/yne-bearing moiety comprises a polymer, a capture moiety, a label, a carbohydrate, a nucleic acid, or a second polypeptide. The ene/yne functional groups may be introduced into ene/yne-bearing moieties detailed herein and other suitable compounds by methods know in the art.

The biologically active components may be a wide variety of materials or compounds including, but not limited to, a tissue, a cell, a protein, a peptide, a toxin, a small molecule drug, a nucleic acid, an encapsulated nucleic acid (for example encapsulated in a lipid nanoparticle), a lipid, a carbohydrate, or an agricultural compound. Cell types include cells of epithelial and mesenchymal origin such as stem cells, fibroblasts, keratinocytes, osteoblasts, chondrocytes, and endothelial cells. For non-limiting example, types of proteins include adhesion peptides (such as RGD adhesion sequence), growth factors, cytokines, interleukins, hormones, antihormones, signaling compounds, enzymes, serum proteins, albumins, macroglobulins, globulins, agglutinins, lectins, extracellular matrix proteins, antibodies, and antigens. Other proteins include peptide and protein hormones, growth factors, cytokines, interleukins, receptors, solubilized receptors, therapeutic proteins, enzymes, and structural proteins. Growth factors may include AM, Ang, BMP, BDNF, GDNF, GCSF, GM-CSF, GDF, HGF, HDGF, KGF, MSF, NGF, TPO, FBS, EPO, IGF, EGF, FGF, TGF, PDGF and interleukins including their derivatives and family members. Structural proteins include fibrin, fibrinogen, fibronectins, keratins, actins, laminins and collagens. Types of small molecule drugs include, but are not limited to, analgesics, antipyretics, nonsteroidal anti-inflammatory drugs, antiallergics, antibacterial drugs, antianemia drugs, cytotoxic drugs, antihypertensive drugs, dermatological drugs, psychotherapeutic drugs, vitamins, minerals, anorexiants, dietetics, antiadiposity drugs, carbohydrate metabolism drugs, protein metabolism drugs, thyroid drugs, antithyroid drugs, and coenzymes. Types of agricultural compounds include, but are not limited to, fungicides, herbicides, fertilizers, pesticides, carbohydrates, nucleic acids, organic molecules, and inorganic biologically active molecules.

As will be understood by one skilled in the art, there are a number of ways to add an ene/yne group to the ene/yne-bearing moieties described herein. These methods may result in a linker group between the ene/yne-bearing moiety and the ene/yne functional group. In one embodiment, a PEG is modified with κ-norbornene-2-carboxylic acid such that one or more terminal norbornene moiety (norborn-2-en-5-yl) is added to the PEG via an ester linkage. In another embodiment, PEG amine is modified with NHS-Norbornene such that one or more terminal norbornene moiety (norborn-2-en-5-yl) is added to the PEG via an amide linkage. A non-limiting example is provided below and illustrates the formation of a norbornene modified PEG:

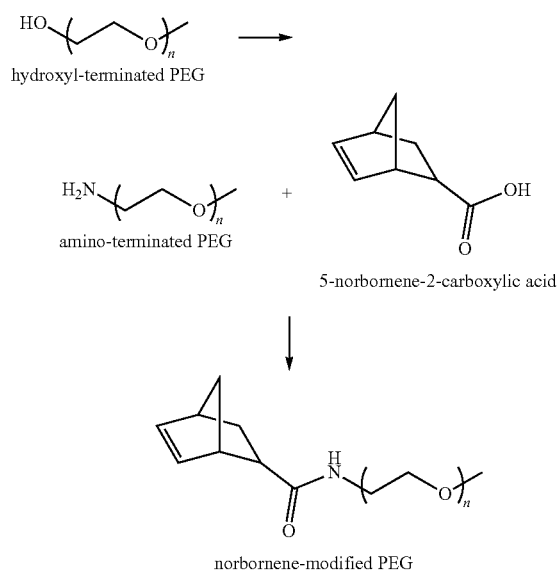

In some embodiments, the method uses an ene compound comprising one reactive ene group. In some embodiments, the ene compound comprises two or more reactive ene groups. In some embodiments, the ene compound comprises two reactive ene groups. In some embodiments, the ene compound comprises three or four or more reactive ene groups.

Polypeptide Modification/Derivatization

Figure 4A:
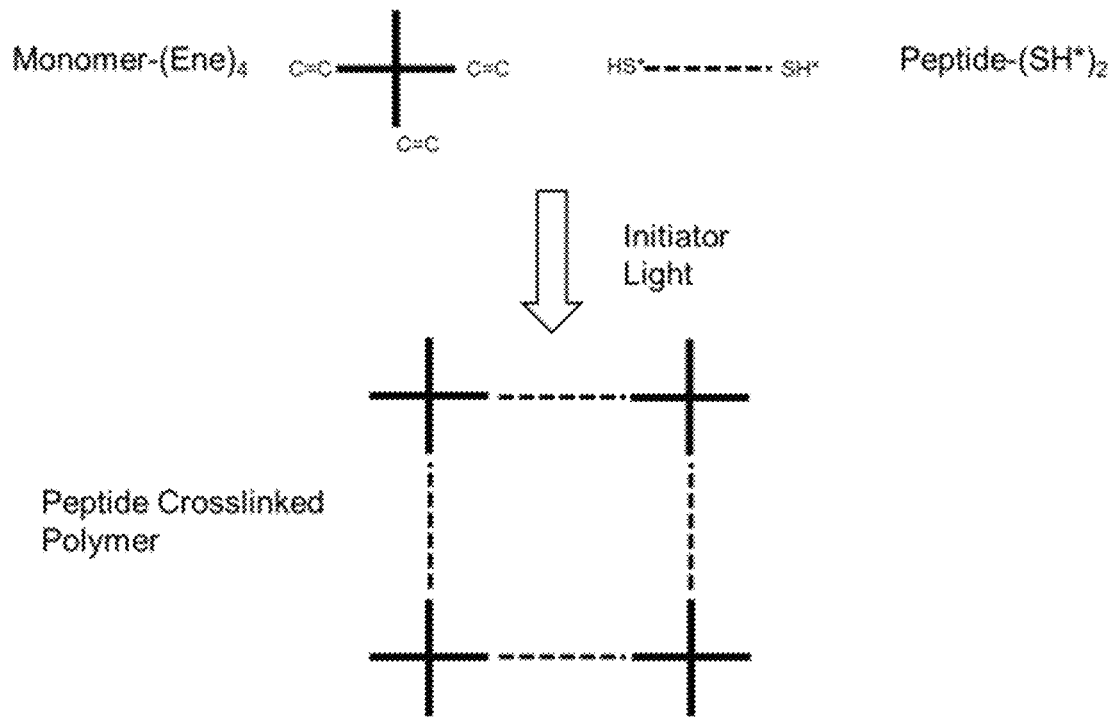
FIGS. 4A-4E show schematic exemplary aspects of associating a polypeptide with a polymer matrix.
Figure 4B:
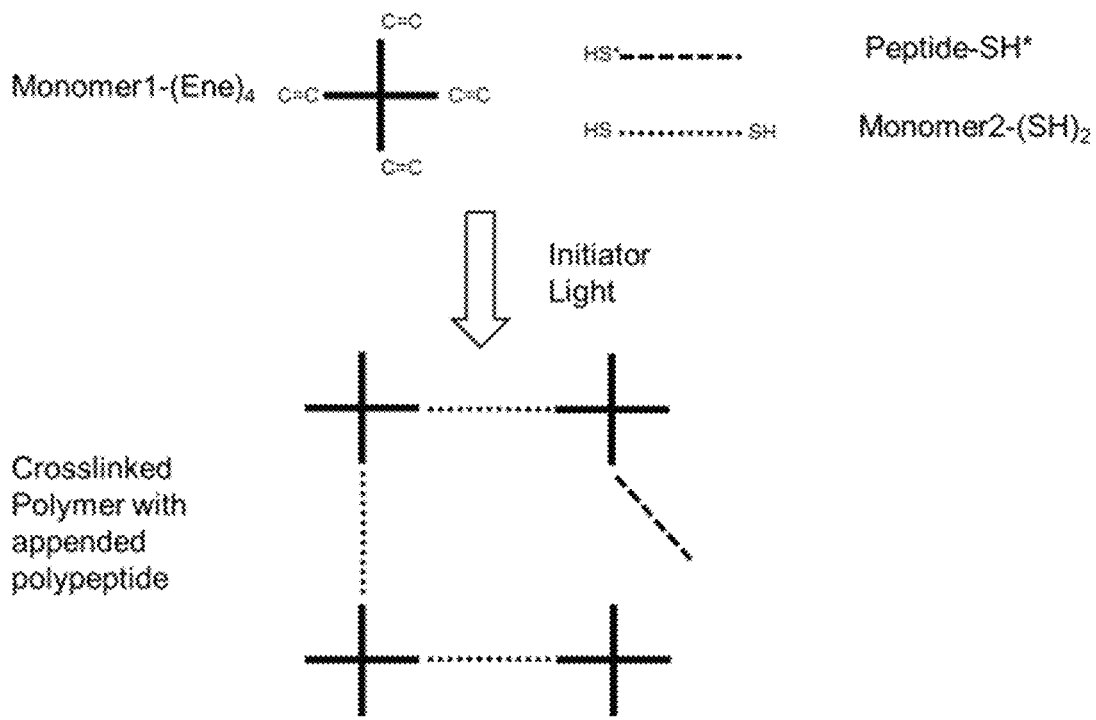

In some embodiments, a polypeptide is modified by attaching another moiety (the second moiety) to the polypeptide via a radical-mediated thiol-ene reaction. In some embodiments, the peptide has one or more reactive thiol groups. Said reactive thiol groups may be separated from the peptide backbone by two or more carbon atoms. The second moiety contains one or more reactive ene groups. In a preferred embodiment, the peptide has only one such reactive thiol group and the second moiety has only one reactive ene group (FIG. 4D).

In some embodiments of the method for linking a polypeptide using radical-mediated thiol-ene chemistry, the polypeptide comprises one or more reactive thiol groups described herein and the ene compound comprises one reactive ene group described herein. In such instances, one or more of the ene-bearing moieties described herein may be linked to the polypeptide via a thioether derived from the one or more reactive thiol groups of the polypeptide.

In certain embodiments the polypeptide can be selected from the following peptide and protein hormones, growth factors, cytokines, interleukins, receptors, solubilized receptors, therapeutic proteins, enzymes, and structural proteins. Growth factors may include AM, Ang, BMP, BDNF, GDNF, GCSF, GM-CSF, GDF, HGF, HDGF, KGF, MSF, NGF, TPO, FBS, EPO, IGF, EGF, FGF, TGF, PDGF and interleukins including their derivatives and family members. Structural proteins include fibrin, fibrinogen, fibronectins, keratins, actins, laminins and collagens.

In some embodiments, the ene compound comprises a biological active component, for example, a drug, a toxin or a pesticide. In some embodiments, the ene compound comprises a polymer (e.g., a polyethylene glycol), a capture moiety or tag (e.g., biotin), a label (e.g., a fluorescent label, a chromophore, or a fluorophore), a sugar or carbohydrate, a nucleic acid, or a second polypeptide.

In some embodiments of the method, the polypeptide comprises one reactive thiol group described herein and the ene compound comprises one reactive ene group described herein. In such instances, the polypeptide is linked to (conjugated with) the ene-bearing moiety of the ene compound via a thioether linkage formed by the thiol-ene reaction.

The methods may be used to link a protein or peptide to a second moiety, for example, to carry a biologically active component (such as a biological components described herein), or to provide additional properties to the polypeptide, such as a polymer to extend the in vivo circulating half-life (such as PEG), a biotin (or other capture moiety or tag) to provide a capture function, a label (such as a fluorescent label, a chromophore, or a fluorophore), a sugar or other carbohydrate, a nucleic acid, another polypeptide. One embodiment is the method is used to add a monomer such that it would change the ADME properties of a peptide. In another embodiment, a functional group is added.

One important advantage of this method is that it can be used to specifically derivatize a protein in the presence of one or multiple cysteine residues. That is, the increased activity of the thiol that is separated from the peptide backbone by two or more carbon atoms, the thiol-ene reaction will occur primarily at the active thiol relative to other cysteine thiol groups within the protein.

Also provided is a linked polypeptide (such as a polypeptide linked to a biological active component, a polymer, a capture moiety, a label, a carbohydrate, a nucleic acid, or a second polypeptide) produced by a method described herein.

In some embodiments of the method for linking a polypeptide using radical-mediated thiol-ene or thiol-yne chemistries, the polypeptide comprises one reactive thiol group described herein and the ene/yne compound comprises one or more reactive ene/yne groups described herein. In such instances, one or more of the polypeptide described herein may be linked to the ene/yne-bearing moieties described herein via a thioether derived from the reactive thiol group of the polypeptide.

In some of these embodiments, the ene/yne compound may comprise any of the ene/yne-bearing moieties described herein. In some embodiments, the ene compound may comprise a polymeric moiety selected from the group consisting of poly(lactic acid) (PLA); polyglycolide (PGA); a copolymer of PLA and PGA (PLGA); poly(vinyl alcohol) (PVA); poly(ethylene glycol) (PEG); poly(ethylene oxide); a poly(ethylene oxide)-co-poly(propylene oxide) block copolymer; a poloxamine; a polyanhydride; a polyorthoester; a poly(hydroxy acids); a polydioxanone; a polycarbonate; a polyaminocarbonate; a poly(vinyl pyrrolidone); a poly(ethyl oxazoline); a polyurethane; a carboxymethyl cellulose; a hydroxyalkylated cellulose; a polypeptide; a nucleic acid; a modified nucleic acid; a locked nucleic acid; a polysaccharide; a carbohydrate; heparan sulfate; chondroitin sulfate; heparin, alginate; and a combination thereof.

In some embodiments, the ene compound contains any suitable ethylenically unsaturated group such as, but not limited to, vinylacetyl, vinyl ester, vinylsulfonyl, vinyl ether, allyl, acrylate ester, methacrylate ester, acrylamido, maleimido, propenyl ether, allyl ether, alkenyl, unsaturated ester, dienyl, N-vinylcarbamoyl and norborn-2-en-5-yl. In a preferred embodiment the ene compound comprises a norborn-2-en-5-yl group. In some embodiments, the reactive ene group of the ene compound may be selected from any suitable ethylenically unsaturated group such as, but not limited to, vinylacetyl, vinyl ester, vinylsulfonyl, vinyl ether, allyl, acrylate ester, methacrylate ester, acrylamido, maleimido, propenyl ether, allyl ether, alkenyl, unsaturated ester, dienyl, N-vinylcarbamoyl and norborn-2-en-5-yl. In some embodiments, the ene compound comprises one or more norbornene (e.g., norborn-2-en-5-yl) groups. As is understood by a person of skill in the art, the ethylenically unsaturated group may be further substituted with one or more suitable substituents such as, for non-limiting example, halo, alkyl, alkoxy or oxo. The yne compound contains one or more alkyne groups such as ethynyl, propargyl, propiolate, cyclic alkynes and others.

Figure 4C:
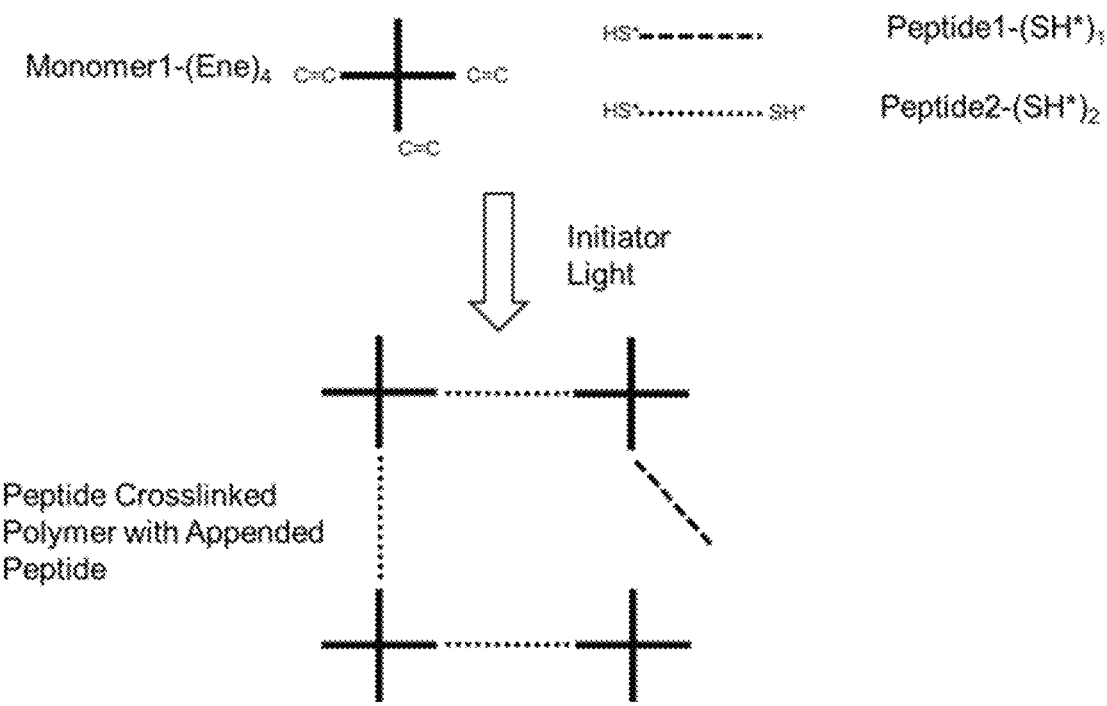
Figure 4D:
Figure 4E:
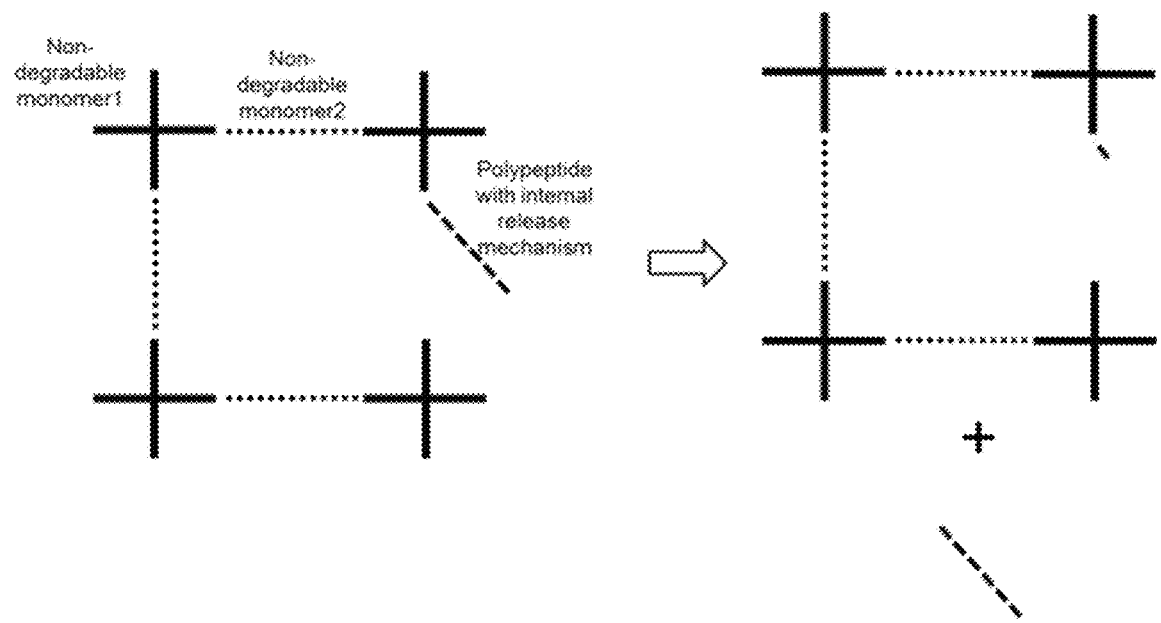

In some embodiments, a polypeptide is modified by attaching the peptide via a radical-mediated thiol-ene reaction into a polymer matrix formed via a radical mediated thiol-ene reaction (FIG. 4C). In certain embodiments, the polymer matrix is formed via a polymer-mediated thiol-ene reaction between a second thiol compound and an ene-containing compound. In some embodiments, the polymer matrix is biocompatible. In other embodiments, the polymer matrix is non-biocompatible. In some embodiments, the polymer matrix is degradable. In other embodiments, the polymer matrix is non-degradable.

In some embodiments of the method for linking a polypeptide using radical-mediated thiol-ene or thiol-yne chemistries, the polypeptide comprises one reactive thiol group described herein and the ene/yne compound comprises two or more reactive ene/yne groups described herein. Thus provided is a method for linking (or attaching) a polypeptide to a thiol-ene based polymer (e.g. a biocompatible cross-linked degradable hydrogel polymer), wherein the polypeptide comprises a peptide backbone and one reactive thiol group (e.g., a reactive thiol group separated from the peptide backbone by two or more carbon atoms), comprising reacting the reactive thiol group of the polypeptide and a second thiol compound with an ene compound comprising two or more reactive ene groups under conditions that promote a radical-mediated thiol-ene reaction (e.g. under conditions using a radical initiator and/or in an aqueous environment), wherein the second thiol compound comprises two or more reactive thiol groups.

In some of these embodiments, the peptide can be selected from the following peptide and protein hormones, growth factors, cytokines, interleukins, receptors, solubilized receptors, therapeutic proteins, enzymes, and structural proteins. Growth factors may include AM, Ang, BMP, BDNF, GDNF, GCSF, GM-CSF, GDF, HGF, HDGF, KGF, MSF, NGF, TPO, FBS, EPO, IGF, EGF, FGF, TGF, PDGF and interleukins including their derivatives and family members. Structural proteins include fibrin, fibrinogen, fibronectins, keratins, actins, laminins and collagens.

In some of these embodiments, the second thiol compound comprises j reactive thiol groups, the ene compound comprises k reactive ene groups, wherein j and k are independently an integer $\geq 2$ and $j+k \geq 5$.

In certain embodiments, the second thiol compound comprises a polymeric moiety selected from the group consisting of poly(lactic acid) (PLA); polyglycolide (PGA); a copolymer of PLA and PGA (PLGA); poly(vinyl alcohol) (PVA); poly(ethylene glycol) (PEG); poly(ethylene oxide); a poly(ethylene oxide)-co-poly(propylene oxide) block copolymer; a poloxamine; a polyanhydride; a polyorthoester; a poly(hydroxy acids); a polydioxanone; a polycarbonate; a polyaminocarbonate; a poly(vinyl pyrrolidone); a poly(ethyl oxazoline); a polyurethane; a carboxymethyl cellulose; a hydroxyalkylated cellulose; a polypeptide; a nucleic acid; a modified nucleic acid; a locked nucleic acid; a polysaccharide; a carbohydrate; heparan sulfate; chondroitin sulfate; heparin, alginate; and a combination thereof. In a preferred embodiment, the second thiol compound comprises a polymeric moiety selected from the group consisting of poly (lactic acid) (PLA), poly(vinyl alcohol) (PVA), and poly (ethylene glycol) (PEG), and a combination thereof.

Some applications require that the attached thiol-ene based polymer has a degradable polymer matrix for controlled release of the attached polypeptide. Other applications may require a non-degradable polymeric matrix for holding the attached polypeptide or releasing the attached polypeptide via an alternative mechanism built in the attached polypeptide.

Thus in some embodiments, the second thiol compound comprises a peptide backbone, a degradable peptide and two or more reactive thiol groups each separated from the peptide backbone by two or more carbon atoms. In some embodiments, the second thiol compound comprises a peptide sequence known to be sensitive to a protease. In a particular embodiment, the second thiol compound comprises a peptide sequence known to be sensitive to a protease and flanked by two homocysteine residues such as a di-homocysteine flanked metalloproteinase (MMP) degradable peptide, to create a hydrogel network that is degraded by cell-secreted MMPs. In another embodiment, the polypeptide is an active thiol-flanked plasmin degradable peptide. In another, two plasmin degradable sequences are included within the peptide.

In other embodiments, the second thiol compound comprises a polyethylene glycol and two terminal thiol groups attached to the polyethylene glycol. In some embodiments, the polypeptide comprises one reactive thiol group, wherein the reactive thiol group is separated from the peptide backbone by a linker comprising at least two carbon atoms and a degradable moiety, thus the attached polypeptide may be released without degrading the polymer matrix. In some of these embodiments, the method further comprises producing the polypeptide comprising the reactive thiol group separated from the peptide backbone by a linker comprising a degradable moiety.

In certain embodiments, the ene compound comprises a polymeric moiety selected from the group consisting of poly(lactic acid) (PLA); polyglycolide (PGA); a copolymer of PLA and PGA (PLGA); poly(vinyl alcohol) (PVA); poly(ethylene glycol) (PEG); poly(ethylene oxide); a poly (ethylene oxide)-co-poly(propylene oxide) block copolymer; a poloxamine; a polyanhydride; a polyorthoester; a poly(hydroxy acids); a polydioxanone; a polycarbonate; a polyaminocarbonate; a poly(vinyl pyrrolidone); a poly(ethyl oxazoline); a polyurethane; a carboxymethyl cellulose; a hydroxyalkylated cellulose; a polypeptide; a nucleic acid; a modified nucleic acid; a locked nucleic acid; a polysaccharide; a carbohydrate; heparan sulfate; chondroitin sulfate; heparin, alginate; and a combination thereof. In a preferred embodiment, the ene compound comprises a polymeric moiety selected from the group consisting of polypeptide, poly(lactic acid) (PLA), poly(vinyl alcohol) (PVA), and poly(ethylene glycol) (PEG), and a combination thereof.

In some embodiments, the ene compound contains any suitable ethylenically unsaturated group such as, but not limited to, vinylacetyl, vinyl ester, vinylsulfonyl, vinyl ether, allyl, acrylate ester, methacrylate ester, acrylamido, maleimido, propenyl ether, allyl ether, alkenyl, unsaturated ester, dienyl, N-vinylcarbamoyl and norborn-2-en-5-yl. In a preferred embodiment the ene compound comprises a norborn-2-en-5-yl group. In some embodiments, the reactive ene group of the ene compound may be selected from any suitable ethylenically unsaturated group such as, but not limited to, vinylacetyl, vinyl ester, vinylsulfonyl, vinyl ether, allyl, acrylate ester, methacrylate ester, acrylamido, maleimido, propenyl ether, allyl ether, alkenyl, unsaturated ester, dienyl, N-vinylcarbamoyl and norborn-2-en-5-yl. In some embodiments, the reactive ene group is norborn-2-en-5-yl. As is understood by a person of skill in the art, the ethylenically unsaturated group may be further substituted with one or more suitable substituents such as, for non-limiting example, halo, alkyl, alkoxy or oxo.

Further provided is compound comprising one or more linked polypeptides (such as a compound comprising multiple polypeptides linked to an ene-bearing moiety or a thiol-ene based polymer) produced by a method described herein.

Cross-Linking

In some embodiments of the method for linking a polypeptide using radical-mediated thiol-ene chemistry, the polypeptide comprises two reactive thiol groups described herein and the ene compound comprises two reactive ene groups described herein. In such instances, a linear polymer is formed having repeating units comprising the polypeptide linked to the ene-bearing moiety via thioether linkages derived from radical-mediated thiol-ene reactions.

In some embodiments of the method for linking a polypeptide using radical-mediated thiol-ene or thiol-yne chemistries, the polypeptide comprises two or more reactive thiol groups described herein and the ene/yne compound comprises two or more reactive ene/yne groups described herein. In such instances, one or more of the polypeptide described herein may be linked to the ene/yne-bearing moieties described herein via a thioether derived from the reactive thiol group of the polypeptide.

In certain embodiments, the method uses a polypeptide comprising n reactive thiol groups, and an ene compound comprising m reactive ene groups, wherein n and m are independently an integer ≥2 and n+m≥5. The polypeptide is cross-linked via the reactive thiol groups with the ene-bearing moiety to produce a thiol-ene based polymeric matrix.

The ene group may be selected from any suitable ethylenically unsaturated group such as, but not limited to, vinylacetyl, vinyl ester, vinylsulfonyl, vinyl ether, allyl, acrylate ester, methacrylate ester, acrylamido, maleimido, propenyl ether, allyl ether, alkenyl, unsaturated ester, dienyl, N-vinylcarbamoyl and norborn-2-en-5-yl. In a preferred embodiment, the ene group is norborn-2-en-5-yl. As is understood by a person of skill in the art, the ethylenically unsaturated group may be further substituted with one or more suitable substituents such as, for non-limiting example, halo, alkyl, alkoxy or oxo.

The yne compound may contain one or more alkyne groups such as ethynyl, propargyl, propiolate, cyclic alkynes and others.

In some embodiments, the ene compound can be any of the ene-containing compounds described herein. In some embodiments, the ene compound is an ene-modified biocompatible monomer, and the thiol-ene reaction provides a biocompatible cross-linked polymeric matrix.

As will be understood by one skilled in the art, there are a number of ways to add an ene/yne group to the ene/yne-bearing moieties described herein. These methods may result in a linker group between the ene/yne-bearing moiety and the ene/yne functional group. In one embodiment, a PEG is modified with 5-norbornene-2-carboxylic acid such that one or more terminal norbornene (norborn-2-en-5-yl) moiety is added to the PEG via an ester linkage. In another embodiment, PEG amine is modified with NHS-Norbornene such that one or more terminal norbornene moiety (e.g., norborn-2-en-5-yl) is added to the PEG via an amide linkage.

In some embodiments, the yne compound can be any of the yne-containing compounds described herein. In some embodiments, the yne is an yne-modified biocompatible monomer, and the thiol-yne and subsequent thiol-ene reactions provide a biocompatible cross-linked polymeric material.

In some embodiments, the polypeptide further comprises a peptide sequence known to be sensitive to a protease, for example, a peptide degradable by a matrix metalloprotease. In some embodiments, the polypeptide comprises a peptide sequence known to be sensitive to a protease and flanked by two homocysteine residues such as a di-homocysteine flanked metalloproteinase (MMP) degradable peptide. The hydrogel network created using such polypeptide is degradable by cell-secreted MMPs. One particular example of such polypeptide is "hC MMPA", a di-homocysteine analog MMPA (amino acid sequence KCGPQGIAGQCK (SEQ ID NO: 1)), which has identical sequence to MMPA but replacing each cysteine residue with homocysteine. In another embodiment, the polypeptide is an active thiol-flanked plasmin degradable peptide. In another, two plasmin degradable sequences are included within the peptide.

In some embodiments, the ene compound is an ene-modified biocompatible monomer and the polypeptide comprises a peptide sequence known to be sensitive to a protease and flanked by two homocysteine residues (e.g., a di-homocysteine flanked metalloproteinase (MMP) degradable peptide). In such case, the thiol-ene reaction provides a biocompatible cross-linked degradable hydrogel polymer (e.g., degradable by MMPs).

In some embodiments, an alkyne-containing compound (or yne compound) is used in place or in addition to the ene compound used in the crosslinking reaction. The primary thiol-yne adduct may undergo further thiol-ene reaction with a reactive thiol, thus providing further cross-linking.

Also provided is a cross-linked polypeptide (such as a cross-linked thiol-ene based polymer) produced by a method described herein.

Cross-Linked Degradable Hydrogel Polymer

Figure 3:
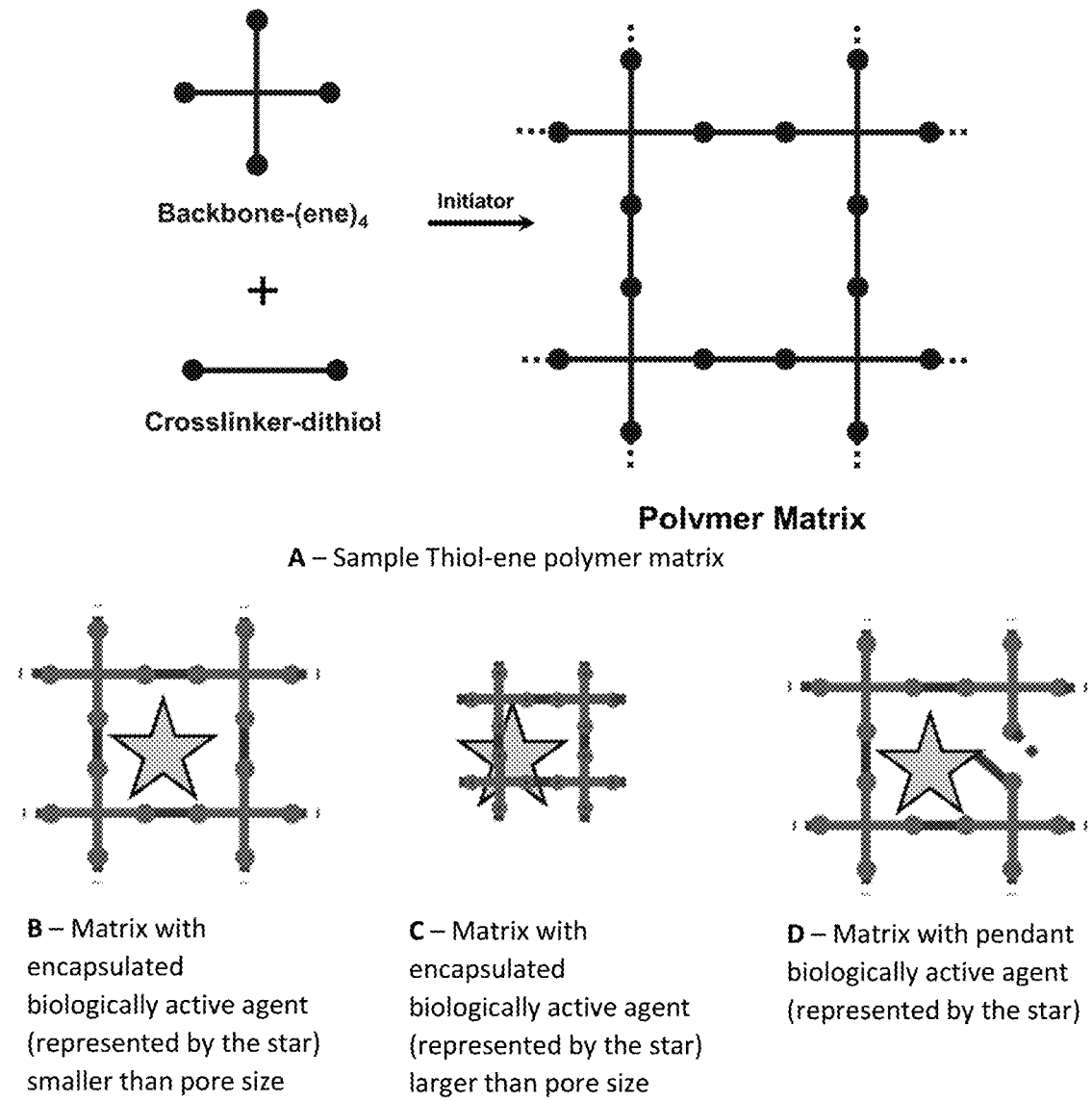
FIG. 3 shows schematic exemplary aspects of associating a biologically active ingredient with a polymer matrix.

In one aspect, a thiol containing polypeptide crosslinker is used to crosslink an ene compound in order to create a bio-compatible polymer (for example, as illustrated in FIG. 3A or FIG. 4A). The polypeptide is synthesized or otherwise modified to contain two (2) or more reactive thiol groups. Said reactive thiol groups may be separated from the polypeptide backbone by two (2) or more carbon atoms. In a particular embodiment, two (2) or more homocysteine residues are incorporated in the polypeptide to provide the two (2) or more thiols.

In some embodiments, provided is a method for producing a biocompatible cross-linked degradable hydrogel polymer comprising reacting a reactive thiol compound with a radical initiator and a reactive ene compound, wherein the reactive thiol compound comprising a peptide backbone, a degradable peptide and two or more reactive thiol groups each separated from the peptide backbone by two or more carbon atoms; and the reactive ene compound is an ene-modified biocompatible monomer comprising two or more reactive ene groups.

In certain embodiments, the polypeptide comprises n reactive thiol groups, the ene compound comprises m reactive ene groups, wherein n and m are independently an integer ≥2 and n+m≥5.

In some embodiments, the reactive thiol group of the polypeptide is separated from the peptide backbone of the polypeptide by two or more carbon atoms. In some embodiments, the reactive thiol groups of the reactive thiol compound are independently selected from a thiol group of a homocysteine residue of the polypeptide, a thiol group of a 2-amino-5-mercaptopentanoic acid residue of the polypeptide and a thiol group attached to the side chain amino group of a lysine residue via a linker. In some embodiments, the method further comprises producing the polypeptide by introducing reactive thiol groups into a polypeptide by a method/process describe herein to producing such a polypeptide, for example, by peptide synthesis using an amino acid having the desired thiol group or by attaching a reactive thiol group to a polypeptide via an amino group of a lysine residue. The reactive thiol group of the polypeptide can be attached to the side chain amino group of a lysine using a thiolating agent. Examples of such thiolating agents include, but are not limited to, N-succinimidyl-S-acetylthiopropionate (SATP), N-acetyl homocysteine thiolactone, and NHS-PEG-SH.

In some embodiments, the polypeptide may comprise two or more reactive thiol groups each separated from the peptide backbone of the polypeptide by two or more carbon atoms.

The thiol-ene reaction can be chemically or photochemically initiated. In some embodiments, the reaction is started by a radical initiator, for example, a photoinitiator. In some embodiments, the radical initiator is a photoinitiator selected from the group consisting of lithium phenyl-2,4,6-trimethylbenzoylphosphinate (LAP), sodium phenyl-2,4,6-trimethylbenzoylphosphinate (NAP), 2-hydroxy-1-[4-(2-hydroxyethoxy)phenyl]-2-methyl-1-propanone (e.g., Irgacure® 2959), 1-hydroxy-cyclohexyl-phenyl-ketone (e.g., Irgacure® 184) and 2,2-dimethoxy-1,2-diphenylethan-1-one (e.g., Irgacure® 651). In some embodiments, the wavelength of the light is chosen to match the excitation wavelength of the photoinitiator. In some embodiments, the thiol-ene reaction is controlled to reach between about 70% completion and about 95% completion, for example, as measured by rheology or by consumption of free thiol using Elman's assay. In some embodiments, the thiol-ene reaction is performed in an aqueous environment or an aqueous medium.

In some embodiments, the ene compound can be any suitable ethylenically unsaturated group such as, but not limited to, vinylacetyl, vinyl ester, vinylsulfonyl, vinyl ether, allyl, acrylate ester, methacrylate ester, acrylamido, maleimido, propenyl ether, allyl ether, alkenyl, unsaturated ester, dienyl, N-vinylcarbamoyl and norborn-2-en-5-yl. In a preferred embodiment the ene compound comprises a norbon-2-en-5-yl group.

In some embodiments, the ene compound can be selected from any ene-modified biocompatible monomers, including without limitation poly(lactic acid) (PLA); polyglycolide (PGA); a copolymer of PLA and PGA (PLGA); poly(vinyl alcohol) (PVA); poly(ethylene glycol) (PEG); poly(ethylene oxide); a poly(ethylene oxide)-co-poly(propylene oxide) block copolymer; a poloxamine; a polyanhydride; a polyorthoester; a poly(hydroxy acids); a polydioxanone; a polycarbonate; a polyaminocarbonate; a poly(vinyl pyrrolidone); a poly(ethyl oxazoline); a polyurethane; a carboxymethyl cellulose; a hydroxyalkylated cellulose; a polypeptide; a nucleic acid; a modified nucleic acid; a locked nucleic acid; a polysaccharide; a carbohydrate; heparan sulfate; chondroitin sulfate; heparin, alginate; and a combination thereof. In a particular embodiment, the ene compound is an ene-modified polyethylene glycol (PEG). In a preferred embodiment, a PEG is modified with 5-norbornene-2-carboxylic acid such that terminal norbornene(s) (norborn-2-en-5-yl) will be added to the PEG via an ester linkage. In another embodiment, PEG amine is modified with NHS-Norbornene such that terminal norbornene(s) (norborn-2-en-5-yl) will be added to the PEG via an amide linkage.

In some embodiments, the resultant biopolymer forms a 3-dimensional network. In particular embodiments, the biopolymer forms a hydrogel containing >98%, >95%, >90%, >80%, or >70% water.

For many biomedical applications, it is desirable to encapsulate or incorporate a biologically active component into the polymer matrix.

In many cases, it is desirable to simply include the above biologically active components within the polymer matrix. In some instances, the non-covalently encapsulated components can be released as the polymer matrix degrades (FIG. 3C). In other instances, where the component is smaller than the polymer matrix pore size, the component will be released by diffusion out of the polymer network (FIG. 3B). In some embodiments, the biologically active component can first be encapsulated in a nano- or micro-particle, which is then encapsulated within the polymer matrix. Methods for encapsulation of biologically active components within particles are known to those skilled in the art.

In other cases, it is desirable to attach or incorporate the biologically active component into the polymer network. That is, to attach or incorporate the component to the polymer matrix through one or more covalent bonds. For example, for biologically active components that are smaller than the pore size, it may be desirable to covalently attach the component to the network such that it will only be released when the network is degraded (FIG. 3D). In some embodiments, the biologically active component is attached to the polymer network via the same peptide that is used to crosslink the network. In other embodiments, the biologically active component is attached by a degradable or non-degradable linker. In some instances the degradable linker is a hydrolytically or enzymatically degradable linker. In particular embodiments, enzymatically degradable linker is a protease cleavable peptide. In each of the above cases, if the biologically active component is to be attached or incorporated into the network (either with or without an intervening linker) via a thiol on a peptide, that thiol should be separated from the peptide backbone by two or more carbon atoms.

In some embodiments, the method further comprises adding a biologically active component to the reaction mixture, wherein the biologically active component is associated with the polymer matrix of the biocompatible cross-linked degradable hydrogel polymer. In some of these embodiments, the biologically active component is encapsulated in the polymer matrix, where there is no covalent bond between the biologically active component and the polymer matrix. In some of these embodiments, the biologically active component is covalently bound to the polymer matrix. Depending on the location of the biologically active component relative to the polymer matrix, the biologically active component is said to be incorporated into the polymer matrix or attached onto the polymer matrix.

The biologically active component may be any of applicable biomaterial such the biologically active component described herein, for example, a tissue, a cell, a protein, a peptide, a small molecule drug, a nucleic acid, an encapsulated nucleic acid (for example encapsulated in a lipid nanoparticle), a lipid, a carbohydrate, or an agricultural compound described herein.

The biologically active component may be incorporated into a biologically active polypeptide, which can be modified by introducing a reactive thiol group suitable for use in the thiol-ene reaction of the invention.

Thus in some embodiments, the method comprises introducing a reactive thiol group to a biologically active polypeptide (for example, by linking a thiol group to a lysine side chain amine using an NHS-PEG-SH reagent as described herein) and reacting the reactive thiol group with an ene group of the ene compound.

In some embodiments, the biologically active component is a biologically active polypeptide covalently bound to the polymer matrix via a thioether linkage formed by reacting a reactive thiol group of the biologically active polypeptide with an ene group, wherein the thio group of the thioether linkage is separated from the backbone of the biologically active polypeptide by two or more carbon atoms.

Further provided is a biocompatible cross-linked degradable hydrogel polymer produced by a method described herein. In some embodiments, the biocompatible cross-linked degradable hydrogel polymer further comprises a biologically active component associated with the polymer matrix of the biocompatible cross-linked degradable hydrogel polymer. In some of these embodiments, the biologically active component is encapsulated in the polymer matrix. In some of these embodiments, the biologically active component is covalently bound to (e.g., incorporated into or attached onto) the polymer matrix.

Compositions

Using the methods described herein for reacting a reactive thiol group of a polypeptide (for example a thiol group that is separated from the peptide backbone by at least two carbon atoms) with an olefin containing compound (ene compound) under conditions that promote radical-mediated thiol-ene reactions (for example in the presence of a radical initiator), compounds and compositions are produced comprising a polypeptide (such as a peptide or a protein) covalently bond to another moiety via a thioether linkage that is formed by a free radical reaction between the reactive thiol group and an ene group of the olefin containing compound; a biocompatible cross-linked degradable hydrogel polymer that is formed by a free radical reaction between the reactive thiol group and an ene group of the olefin containing compound; and a biocompatible cross-linked degradable hydrogel polymer further comprising a biologically active component associated with [e.g., encapsulated in or covalently bond to (incorporated into or attached onto)] the polymer matrix of the biocompatible cross-linked degradable hydrogel polymer that is formed by a free radical reaction between the reactive thiol group and an ene group of the olefin containing compound. Depending on the number of reactive thiol groups in each molecule of the thiol-containing polypeptide and the number of reactive ene groups in the ene compound, a variety of compounds or compositions can be produced. As is understood by a person of skill in the art, biocompatible or non-biocompatible compounds and compositions can be produced using the methods described herein depending on the biocompatible or non-biocompatible nature of the ene compound and one or more thiol compounds. As is also understood by a person of skill in the art, degradable or non-degradable compounds and compositions can be produced using the methods described herein depending on the degradable or non-degradable nature of the ene compound and one or more thiol compounds. As is further understood by a person of skill in the art, the compounds and compositions, which can be produced using the methods described herein, may be tailored to comprises both degradable and non-degradable sections, for non-limiting example, a degradable polypeptide can be linked to a non-degradable polymer matrix. Degradable compounds and compositions may be degraded through enzymatic, biological, chemical, or physical processes.

When a thiol-containing polypeptide comprising one or more reactive thiol group reacts with an ene compound that contains only one reactive ene group, the polypeptide is modified to carry one or more "terminal" moieties derived from the ene containing compound as each ene containing compound is capable of reacting with only one reactive thiol group.

Thus provided is compound of formula (A):

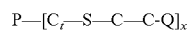

P—[$C_t$—S—C—C—Q]$_x$ wherein P is a polypeptide, $C_t$ is a linker comprising at least two carbon atoms, (t≥2), x is 1 or an integer greater than 1 and Q is a biological active component (e.g., a drug, a toxin or a pesticide), a polymer moiety (e.g., PEG), a capture moiety (e.g., biotin), a label (e.g., a fluorescent label, a chromophore, or a fluorophore), a sugar or carbohydrate, a nucleic acid, or a second polypeptide. In some embodiments, $C_t$ is selected from the group consisting of ($C_2$-$C_6$) alkanediyl-, —C(=O)—($C_1$-$C_6$)-alkanediyl- and —C(=O)—($C_1$-$C_6$)-alkanediyl-(O—$CH_2CH_2$)$_z$— where z is an integer from 1-10,000. In some embodiments, $C_t$ may be further substituted with one or more substituents selected from halo, alkyl, and alkoxy. As is understood by a person of skill in the art, the C—C moiety between the sulfur atom and Q is a moiety resulting from the thiol-ene reaction of a reactive thiol group with a reactive ene group, such as a reactive ene group selected from the group consisting of vinylacetyl, vinyl ester, vinylsulfonyl, vinyl ether, allyl, acrylate ester, methacrylate ester, acrylamido, maleimido, propenyl ether, allyl ether, alkenyl, unsaturated ester, dienyl, N-vinylcarbamoyl and norborn-2-en-5-yl. In some embodiments, the C—C moiety between the sulfur atom and Q is a moiety resulting from the thiol-ene reaction of a reactive thiol group with a reactive ene group, wherein the reactive ene group is norborn-2-en-5-yl. As is understood by a person of skill in the art, the ethylenically unsaturated group may be further substituted with one or more suitable substituents such as, for non-limiting example, halo, alkyl, alkoxy or oxo. As will be understood by one skilled in the art, there are a number of ways to add a C—C moiety to the Q group. These methods may result in a linker group between the ene/yne-bearing moiety and the ene/yne functional group, such as, for non-limiting example, an amide functionality, ester functionality or a combination thereof. In one embodiment, a PEG is modified with 5-norbornene-2-carboxylic acid such that one or more terminal norbornene moiety (norborn-2-en-5-yl) is added to the PEG via an ester linkage. In another embodiment, PEG amine is modified with NHS-Norbornene such that one or more terminal norbornene moiety (norborn-2-en-5-yl) is added to the PEG via an amide linkage. In some embodiments, the C—C moiety between the sulfur atom and Q is a moiety selected from the group consisting of —CH$_2$—CH$_2$—CH$_2$—C(=O)—, —CH$_2$—CH$_2$—OC(=O)—, —CH$_2$—CH$_2$—S(=O)$_2$—, —CH$_2$—CH$_2$—O—, —(C$_2$-C$_6$)-alkanediyl-, —CH$_2$—CH$_2$—C(=O)O—, —CH$_2$—CH(CH$_3$)—C(=O)O—, —CH$_2$—CH$_2$—C(=O)NH—, —CH(CH$_3$)—CH$_2$—O—, —CH$_2$—CH$_2$—CH$_2$—O—, —CH$_2$—CH$_2$—NHC(=O)—,

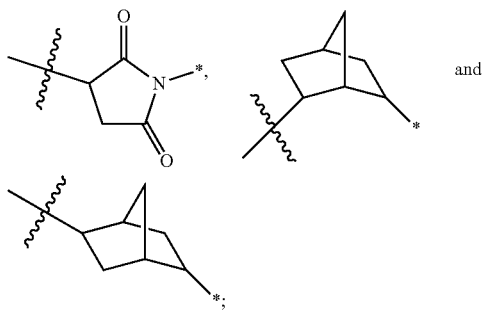

and wherein the first dash (—C—C) or wavy line represents bonding to the sulfur atom and the second dash (C—C—) or bonding to the Q group which may be a direct bond or via a linker moiety, such as, for non-limiting example, an amide functionality, ester functionality or a combination thereof. It will be appreciated that such C—C moieties are derived from an ene group comprising a moiety selected from the group consisting of vinylacetyl, vinyl ester, vinylsulfonyl, vinyl ether, allyl, acrylate ester, methacrylate ester, acrylamido, maleimido, propenyl ether, allyl ether, alkenyl, unsaturated ester, dienyl, N-vinylcarbamoyl and norborn-2-en-5-yl.

In such embodiments, polypeptide P is linked to one or more thioether moieties via a linker of two carbon atoms in length or longer. Each thioether moiety is also attached to a Q moiety via the ethylene unit derived from the ene group.

In some embodiments of formula (A), P can be selected from peptide and protein hormones, growth factors, cytokines, interleukins, receptors, solubilized receptors, therapeutic proteins, enzymes, and structural proteins. Growth factors may include AM, Ang, BMP, BDNF, GDNF, GCSF, GM-CSF, GDF, HGF, HDGF, KGF, MSF, NGF, TPO, FBS, EPO, IGF, EGF, FGF, TGF, PDGF and interleukins including their derivatives and family members. Structural proteins include fibrin, fibrinogen, fibronectins, keratins, actins, laminins and collagens.

In some embodiments of formula (A), the polypeptide P further comprises a peptide sequence known to be sensitive to a protease. In another embodiment, the polypeptide is an active thiol-flanked plasmin degradable peptide. In another, two plasmin degradable sequences are included within the peptide. In a particular embodiment, the polypeptide is a homocysteine-flanked matrix metalloproteinase (MMP) degradable peptide, to create a hydrogel network that is degraded by cell-secreted MMPs.

In some embodiments, x is 1, where one Q moiety is linked to the polypeptide P. In some embodiments, x is 2, 3, 4 or a greater integer.

In certain embodiments of the formula (A), the P moiety is selected from peptide and protein hormones, growth factors, cytokines, interleukins, receptors, solubilized receptors, therapeutic proteins, enzymes, and structural proteins. Growth factors may include AM, Ang, BMP, BDNF, GDNF, GCSF, GM-CSF, GDF, HGF, HDGF, KGF, MSF, NGF, TPO, FBS, EPO, IGF, EGF, FGF, TGF, PDGF and interleukins including their derivatives and family members. Structural proteins include fibrin, fibrinogen, fibronectins, keratins, actins, laminins and collagens.

In some embodiments, the Q moiety, which is linked to the polypeptide P, is chosen with respect to the specific functional property that the modification is sought to confer, for a non-limiting example, introduction of a fluorophore or chromophore, introduction of an affinity tag, introduction of enzymatic activity, introduction of a certain chemical moiety or moieties, introduction of a hydrophilic, hydrophobic or amphiphilic polymeric tail in order to manipulate solubility, pharmacokinetics, pharmacodynamics or interaction with biological membranes or solid surfaces, generation of a polypeptide-containing polymer or of a telechelic monomer for further polymerization etc., and may include appropriate derivatives of the following (non-limiting example): poly(lactic acid) (PLA), polyglycolide (PGA), copolymers of PLA and PGA (PLGA), poly(vinyl alcohol) (PVA), poly(ethylene glycol) (PEG), poly(ethylene oxide), poly(ethylene oxide)-co-poly(propylene oxide) block copolymers (poloxamers, meroxapols), poloxamines, polyanhydrides, polyorthoesters, poly(hydroxy acids), polydioxanones, polycarbonates, polyaminocarbonates, poly(vinyl pyrrolidone), poly(ethyl oxazoline), a polyurethane, carboxymethyl cellulose, hydroxyalkylated celluloses such as hydroxyethyl cellulose and methylhydroxypropyl cellulose, and natural polymers such as polypeptides, polysaccharides or carbohydrates such as polysucrose, hyaluranic acid, dextran and similar derivatives thereof, heparan sulfate, chondroitin sulfate, heparin, or alginate, and proteins such as gelatin, collagen, albumin, or ovalbumin, fibrinogen, fibrin, laminin, fibronectin, vitronectin, fluorescent proteins such as green fluorescent protein or its analogs, fluorescent and non-fluorescent dyes, fluorescence quenchers, high-affinity tags, such as polypeptide tags (His-tag, FLAG-tag and others), antibodies and fragments thereof, nucleic acid aptamers, oligonucleotides and polynucleotides, high-order macromolecular assemblies such as ribonucleoproteins, viral capsids etc. The reactive ene group of the second moiety may be selected from any suitable ethylenically unsaturated group such as, but not limited to, vinylacetyl, vinyl ester, vinylsulfonyl, vinyl ether, allyl, acrylate ester, methacrylate ester, acrylamido, maleimido, propenyl ether, allyl ether, alkenyl, unsaturated ester, dienyl, N-vinylcarbamoyl and norborn-2-en-5-yl. The Q moiety, which is linked to the polypeptide P, may comprise a polymeric moiety such as, but not limited to, poly(lactic acid) (PLA); polyglycolide (PGA); a copolymer of PLA and PGA (PLGA); poly(vinyl alcohol) (PVA); poly(ethylene glycol) (PEG); poly(ethylene oxide); a poly(ethylene oxide)-co-poly(propylene oxide) block copolymer; a poloxamine; a polyanhydride; a polyorthoester; a poly(hydroxy acids); a polydioxanone; a polycarbonate; a polyaminocarbonate; a poly(vinyl pyrrolidone); a poly(ethyl oxazoline); a polyurethane; a carboxymethyl cellulose; a hydroxyalkylated cellulose; a polypeptide; a nucleic acid; a modified nucleic acid; a locked nucleic acid; a polysaccharide; a carbohydrate; heparan sulfate; chondroitin sulfate; heparin, alginate; and a combination thereof. In some embodiments, the second moiety may comprise a biologically active component.

In certain embodiments of the formula (A), the Q moiety, which is linked to the polypeptide P, may comprise a biologically active component such as any one of the biologically active components described herein. In some embodiments, the Q moiety comprises a polymer, a capture moiety, a label, a carbohydrate, a nucleic acid, or a second polypeptide as described herein.

In some embodiments, the compound of formula (A) is produced by reacting a compound of formula P—[$C_t$—SH]$_x$ and a compound of formula $CH_2$=CH-Q and a radical initiator (such as a photoinitiator described herein), for example, under conditions described herein that promote a radical-mediated thiol-ene reaction, wherein P, $C_t$, t, Q and x are as defined for formula (A) or any variations thereof. In one aspect the $CH_2$=CH— moiety of $CH_2$=CH-Q is a reactive ene group selected from the group consisting of vinylacetyl, vinyl ester, vinylsulfonyl, vinyl ether, allyl, acrylate ester, methacrylate ester, acrylamido, allyl ether, alkenyl, unsaturated ester, dienyl, and N-vinylcarbamoyl.

It is understood that $CH_2$=CH-Q represents an ene group bearing a terminal, unsubstituted alkene moiety, but that substituted alkenes may also be employed and are also described herein. Thus, it will be appreciated that the compound of formula (A) in which the C—C moiety is derived from an alkene other than a terminal, unsubstituted alkene is also provided and may be produced by reacting a compound of formula P—[$C_t$—SH]$_x$ and a compound of formula T-Q and a radical initiator (such as a photoinitiator described herein), wherein P, $C_t$, t, Q and x are as defined for formula (A) or any variations thereof and T indicates an alkene moiety other than a terminal, unsubstituted alkene moiety, under free radical-mediated reaction conditions. In one aspect, T-Q is a cyclic alkene moiety of the following formula

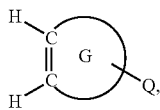

wherein ring G is a monocyclic or bicyclic cycloalkene, which can have one or more annular heteroatoms selected from O, S, and N, and which may be substituted with one or more substituents selected from the group consisting of oxo, halo, alkyl and alkoxy, and where the bicyclic cycloalkene may be a fused, bridged or a spiro bicyclic ring. It will be appreciated that Q may be directly attached to T or may be linked to T via a linker moiety, such as, for non-limiting example, an amide functionality, ester functionality or a combination thereof. Examples of T-Q include Q moieties derivatized with a maleimido group, a propenyl ether group, a norborn-2-en-5-yl group or any combination thereof, any one or more of which may be directly connected to Q or connected to Q via a linker moiety, such as, for non-limiting example, an amide functionality, ester functionality or a combination thereof.

In some embodiments, the T moiety of T-Q is norborn-2-en-5-yl. As will be understood by one skilled in the art, there are a number of ways to add a $CH_2$=CH— moiety to the Q group of $CH_2$=CH-Q or to add a T moiety to the Q group of T-Q. These methods may result in a linker group between the ene/yne-bearing moiety and the ene/yne functional group, such as, for non-limiting example, an amide functionality, ester functionality or a combination thereof. In a preferred embodiment, a PEG is modified with 5-norbornene-2-carboxylic acid such that terminal norbornene(s) (norborn-2-en-5-yl) will be added to the PEG via an ester linkage. In another embodiment, PEG amine is modified with NHS-Norbornene such that terminal norbornene(s) (norborn-2-en-5-yl) will be added to the PEG via an amide linkage. In some embodiments, the $CH_2$=CH— moiety of $CH_2$=CH-Q is a moiety selected from the group consisting of $CH_2$=CH—C(=O)—, $CH_2$=CH—S(=O)$_2$—, $CH_2$=CH—O—, $CH_2$=CH—($C_0$-$C_4$)-alkanediyl-, $CH_2$=CH—C(=O)O—, $CH_2$=C($CH_3$)—C(=O)O—, $CH_2$=CH—C(=O)NH—, $CH_2$=CH—$CH_2$—O—, and $CH_2$=CH—NHC(=O)—, and the T moiety of T-Q is selected from the group consisting of

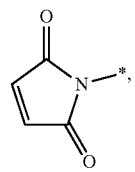

—CH($CH_3$)=CH—O— and

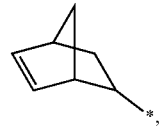

wherein the asterisk represents bonding to the Q group which may be a direct bond or via a linker moiety, such as, for non-limiting example, an amide functionality, ester functionality or a combination thereof.

In some embodiments, the compound of formula (A) is produced in a reduced oxygen environment or in the absence of oxygen, such as in the presence of a degassed solvent.

Non-limiting examples for various compounds of formula $CH_2$=CH-Q and T-Q and corresponding compounds of formula (A), wherein x is 1 (i.e. (A) is of the formula P—$C_t$—S—C—C-Q) are illustrated in Table 3 below. Non-limiting examples for various compounds of formula P—$C_t$—SH and corresponding compounds of formula (A), wherein x is 1 (i.e. (A) is of the formula P—$C_t$—S—C—C-Q) are illustrated in Table 4 below.

TABLE 3

| $CH_2$=CH—Q or T—Q | P—$C_t$—S—C—C—Q |
|---|---|
| ![vinylacetyl structure] | ![product structure] |
| vinylacetyl | |

TABLE 3-continued

| CH₂=CH—Q or T—Q | P—C$_t$—S—C—C—Q |
|---|---|
| vinylsulfonyl | P—C$_t$—S—CH₂CH₂—SO₂—Q |
| vinyl ether | P—C$_t$—S—CH₂CH₂—O—Q |
| allyl | P—C$_t$—S—CH₂CH₂CH₂—Q |
| acrylate ester | P—C$_t$—S—CH₂CH₂—C(=O)—O—Q |
| methacrylate ester | P—C$_t$—S—CH₂—CH(CH₃)—C(=O)—O—Q |
| acrylamido | P—C$_t$—S—CH₂CH₂—C(=O)—NH—Q |

| CH₂=CH—Q or T—Q | P—C$_t$—S—C—C—Q |
|---|---|
| maleimido | P—C$_t$—S-(succinimidyl)-N—Q |
| propenyl ether | P—C$_t$—S—CH(CH₃)—CH₂—O—Q |
| allyl ether | P—C$_t$—S—CH₂CH₂CH₂—O—Q |
| alkenyl | P—C$_t$—S—CH₂CH₂—Q |
| N-vinylcarbamoyl | P—C$_t$—S—CH₂CH₂—NH—C(=O)—Q |
| norborn-2-en-5-yl | P—C$_t$—S-(norbornyl)-Q |

TABLE 4

| P—C$_t$—SH | P—C$_t$—S—C—C—Q |
|---|---|
| P—CH₂CH₂CH₂—SH | P—CH₂CH₂CH₂—S—C—C—Q |
| —(C2-C6)-alkylene-linker | |
| P—C(=O)—CH₂CH₂—SH | P—C(=O)—CH₂CH₂—S—C—C—Q |
| —C(=O)—(C2-C6)-alkylene-linker | |
| P—C(=O)—CH₂CH₂—(O—CH₂CH₂)$_z$—SH | P—C(=O)—CH₂CH₂—(O—CH₂CH₂)$_z$—S—C—C—Q |
| —C(=O)—(C1-C6)-alkylene-(O—CH2CH2)z-linker | |

Also provided is a compound of formula (B):

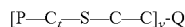

wherein P is a polypeptide, t≥2, $C_t$ is a linker comprising at least two carbon atoms (i.e., P is linked to the thioether moiety via a linker of two carbon atoms in length or longer), y is 1 or an integer greater than 1 (e.g. 2, 3, 4 or more) and Q is selected from the group consisting of poly(lactic acid) (PLA); polyglycolide (PGA); a copolymer of PLA and PGA (PLGA); poly(vinyl alcohol) (PVA); poly(ethylene glycol) (PEG); poly(ethylene oxide); a poly(ethylene oxide)-co-poly(propylene oxide) block copolymer; a poloxamine; a polyanhydride; a polyorthoester; a poly(hydroxy acids); a polydioxanone; a polycarbonate; a polyaminocarbonate; a poly(vinyl pyrrolidone); a poly(ethyl oxazoline); a polyurethane; a carboxymethyl cellulose; a hydroxyalkylated cellulose; a polypeptide; a nucleic acid; a modified nucleic acid; a locked nucleic acid; a polysaccharide; a carbohydrate; heparan sulfate; chondroitin sulfate; heparin, alginate; and a combination thereof. All variations of P, $C_t$, t and Q that are described for formula (A) are equally applicable to, and described for, formula (B) the same as if each and every description, variation, aspect or embodiment were specifically and individually listed for formula (B). That is, it is appreciated that formula (A) describes materials in which more than one —$C_t$—S—C—C-Q may be appended to a given P and that formula (B) describes materials in which more than one P—$C_t$—S—C—C— may be appended to a given Q, but that the underlying P, $C_t$, t and Q may be the same in both formulae.

In some embodiments, $C_t$ is selected from the group consisting of $(C_2-C_6)$alkanediyl-, —C(=O)—$(C_1-C_6)$-alkanediyl- and —C(=O)—$(C_1-C_6)$-alkanediyl-(O—$CH_2CH_2)_z$— where z is an integer from 1-10,000. In some embodiments, $C_t$ may be further substituted with one or more substituents selected from halo, alkyl, and alkoxy. As is understood by a person of skill in the art, each C—C moiety between the sulfur atom and Q is a moiety resulting from the thiol-ene reaction of a reactive thiol group with a reactive ene group, such as a reactive ene group independently selected from the group consisting of vinylacetyl, vinyl ester, vinylsulfonyl, vinyl ether, allyl, acrylate ester, methacrylate ester, acrylamido, maleimido, propenyl ether, allyl ether, alkenyl, unsaturated ester, dienyl, N-vinylcarbamoyl and norborn-2-en-5-yl. In some embodiments, the C—C moiety between the sulfur atom and Q is a moiety resulting from the thiol-ene reaction of a reactive thiol group with a reactive ene group, wherein the reactive ene group is norborn-2-en-5-yl. As will be understood by one skilled in the art, there are a number of ways to add a C—C moiety to the Q group. These methods may result in a linker group between the ene/yne-bearing moiety and the ene/yne functional group, such as, for non-limiting example, an amide functionality, ester functionality or a combination thereof. In one embodiment, a PEG is modified with 5-norbornene-2-carboxylic acid such that one or more terminal norbornene moiety is added to the PEG via an ester linkage. In another embodiment, PEG amine is modified with NHS-Norbornene such that one or more terminal norbornene moiety is added to the PEG via an amide linkage. In some embodiments, each C—C moiety between the sulfur atom and Q is a moiety independently selected from the group consisting of —$CH_2$—$CH_2$—$CH_2$—C(=O)—, —$CH_2$—$CH_2$—OC(=O)—, —$CH_2$—$CH_2$—S(=O)$_2$—, —$(C_2-C_6)$-alkanediyl-, —$CH_2$—$CH_2$—C(=O)O—, —$CH_2$—CH($CH_3$)—C(=O)O—, —$CH_2$—$CH_2$—C(=O)NH—, —CH($CH_3$)—$CH_2$—O—, —$CH_2$—$CH_2$—$CH_2$—O—, —$CH_2$—$CH_2$—NHC(=O)—,

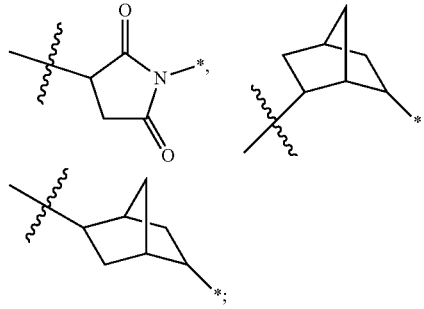

wherein the first dash (—C—C) or wavy line represents bonding to the sulfur atom and the second dash (C—C—) or bonding to the Q group which may be a direct bond or via a linker moiety, such as, for non-limiting example, an amide functionality, ester functionality or a combination thereof. It will be appreciated that such C—C moieties are derived from an ene group comprising a moiety selected from the group consisting of vinylacetyl, vinyl ester, vinylsulfonyl, vinyl ether, allyl, acrylate ester, methacrylate ester, acrylamido, maleimido, propenyl ether, allyl ether, alkenyl, unsaturated ester, dienyl, N-vinylcarbamoyl and norborn-2-en-5-yl.

In some embodiments, the compound of formula (B) is produced by reacting a compound of formula P—$C_t$—SH and a compound of formula $[CH_2=CH]_y$Q and a radical initiator (such as a photoinitiator described herein), for example, under conditions described herein that promote a radical-mediated thiol-ene reaction, wherein P, $C_t$, t, Q and y are as defined for formula (B) or any variations thereof.

In one aspect each $CH_2=CH$— moiety of $[CH_2=CH]_y$Q is a reactive ene group independently selected from the group consisting of vinylacetyl, vinyl ester, vinylsulfonyl, vinyl ether, allyl, acrylate ester, methacrylate ester, acrylamido, allyl ether, alkenyl, unsaturated ester, dienyl, and N-vinylcarbamoyl.

It is understood that $[CH_2=CH]_y$Q represents an ene group bearing one or more terminal, unsubstituted alkene moieties, but that substituted alkenes may also be employed and are also described herein. Thus, it will be appreciated that the compound of formula (B) in which the C—C moiety is derived from an alkene other than a terminal, unsubstituted alkene is also provided and may be produced by reacting a compound of formula P—$C_t$—SH and a compound of formula $[T]_y$-Q and a radical initiator (such as a photoinitiator described herein), wherein P, $C_t$, t, Q and x are as defined for formula (B) or any variations thereof and T indicates an alkene moiety other than a terminal, unsubstituted alkene moiety, under free radical-mediated reaction conditions. In one aspect, $[T]_y$-Q comprises one or more a cyclic alkene moiety and $[T]_y$-Q is of the following formula

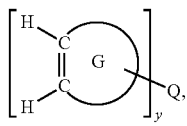

wherein each ring G is independently a monocyclic or bicyclic cycloalkene, which can have one or more annular heteroatoms selected from O, S, and N, and which may be substituted with one or more substituents selected from the group consisting of oxo, halo, alkyl and alkoxy, and where the bicyclic cycloalkene may be a fused, bridged or a spiro bicyclic ring. It will be appreciated that Q may be directly, independently for each of the one or more T moieties, attached to T or may be linked to T via a linker moiety, such as, for non-limiting example, an amide functionality, ester functionality or a combination thereof. Examples of $[T]_y$-Q include Q moieties derivatized with one or more groups independently selected from maleimido group, a propenyl ether group, a norborn-2-en-5-yl group and any combination thereof, any one or more of which may be directly connected to Q or connected to Q via a linker moiety, such as, for non-limiting example, an amide functionality, ester functionality or a combination thereof.

In some embodiments, each T moiety of $[T]_y$-Q is norborn-2-en-5-yl. As will be understood by one skilled in the art, there are a number of ways to add one or more $CH_2=CH$-moieties to the Q group of $[CH_2=CH]_yQ$ or to add one or more T moiety to the Q group of $[T]_y$-Q. These methods may result in a linker group between the ene/yne-bearing moiety and the ene/yne functional group, such as, for non-limiting example, an amide functionality, ester functionality or a combination thereof. In a preferred embodiment, a PEG is modified with 5-norbornene-2-carboxylic acid such that terminal norbornene(s) will be added to the PEG via an ester linkage. In another embodiment, PEG amine is modified with NHS-Norbornene such that terminal norbornene(s) will be added to the PEG via an amide linkage. In some embodiments, each $CH_2=CH-$ moiety of $[CH_2=CH]_yQ$ is a moiety independently selected from the group consisting of $CH_2=CH-C(=O)-$, $CH_2=CH-S(=O)_2-$, $CH_2=CH-O-$, $CH_2=CH-(C_0-C_4)$-alkanediyl-, $CH_2=CH-C(=O)O-$, $CH_2=C(CH_3)-C(=O)O-$, $CH_2=CH-C(=O)NH-$, $CH_2=CH-CH_2-O-$, and $CH_2=CH-NHC(=O)-$, and each T moiety of $[T]_y$-Q is independently selected from the group consisting of

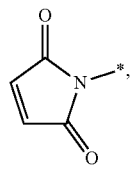

$-CH(CH_3)=CH-O-$ and

wherein the asterisk represents bonding to the Q group which may be a direct bond or via a linker moiety, such as, for non-limiting example, an amide functionality, ester functionality or a combination thereof. In some embodiments, the compound of formula (B) is produced in a reduced oxygen environment or in the absence of oxygen, such as in the presence of a degassed solvent.

In some embodiments, the compound of formula (B) is produced in a reduced oxygen environment or in the absence of oxygen.

In some embodiments of formula (B), P can be selected from peptide and protein hormones, growth factors, cytokines, interleukins, receptors, solubilized receptors, therapeutic proteins, enzymes, and structural proteins. Growth factors may include AM, Ang, BMP, BDNF, GDNF, GCSF, GM-CSF, GDF, HGF, HDGF, KGF, MSF, NGF, TPO, FBS, EPO, IGF, EGF, FGF, TGF, PDGF and interleukins including their derivatives and family members. Structural proteins include fibrin, fibrinogen, fibronectins, keratins, actins, laminins and collagens.

In some embodiments of formula (B), the polypeptide P further comprises a peptide sequence known to be sensitive to a protease. In a particular embodiment, the polypeptide is a homocysteine-flanked matrix metalloproteinase (MMP) degradable peptide, to create a hydrogel network that is degraded by cell-secreted MMPs. In another embodiment, the polypeptide is an active thiol-flanked plasmin degradable peptide. In another, two plasmin degradable sequences are included within the peptide.

In some embodiments of formula (B), Q is a polymeric moiety of formula (Qa):

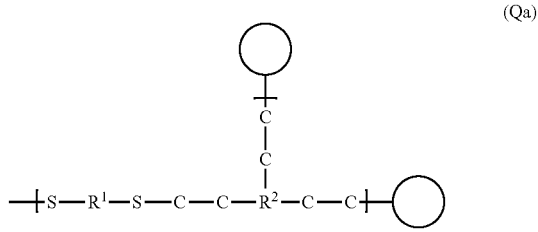

wherein, $R^1$ and $R^2$ are independently selected from the group consisting of poly(lactic acid) (PLA); polyglycolide (PGA); a copolymer of PLA and PGA (PLGA); poly(vinyl alcohol) (PVA); poly(ethylene glycol) (PEG); poly(ethylene oxide); a poly(ethylene oxide)-co-poly(propylene oxide) block copolymer; a poloxamine; a polyanhydride; a polyorthoester; a poly(hydroxy acids); a polydioxanone; a polycarbonate; a polyaminocarbonate; a poly(vinyl pyrrolidone); a poly(ethyl oxazoline); a polyurethane; a carboxymethyl cellulose; a hydroxyalkylated cellulose; a polypeptide; a nucleic acid; a modified nucleic acid; a locked nucleic acid; a polysaccharide; a carbohydrate; heparan sulfate; chondroitin sulfate; heparin, alginate; and a combination thereof; and wherein —O represents a point of attachment to either one of the sulfur atom of one of the $P-C_t-S-$ moieties of formula (B) or a thioether moiety of another subunit of the polymeric moiety of formula (Qa). In some embodiments, $R^1$ is a polypeptide of formula $-C_t-R^{1a}-C_t-$, wherein $R^{1a}$ is a polypeptide, $t \geq 2$ and $C_t$ is a linker comprising at least two carbon atoms. In some embodiments, $C_t$ is selected from the group consisting of $(C_2-C_6)$alkanediyl-, $-C(=O)-(C_1-C_6)$-alkanediyl- and $-C(=O)-(C_1-C_6)$-alkanediyl-$(O-CH_2CH_2)_z-$ where z is an integer from 1-10,000. In some embodiments, $C_t$ may be further substituted with one or more substituents selected from halo, alkyl, and alkoxy. As is understood by a person of skill in the art, each C—C moiety between the sulfur atom and $R^2$ is a moiety resulting from the thiol-ene reaction of a reactive thiol group with a reactive ene group, such as a reactive ene group independently selected from the group consisting of vinylacetyl, vinyl ester, vinylsulfonyl, vinyl ether, allyl, acrylate ester, methacrylate ester, acrylamido, maleimido, propenyl ether, allyl ether, alkenyl, unsaturated ester, dienyl, N-vinylcarbamoyl and norborn-2-en-5-yl. In some embodiments, the C—C moiety between the sulfur atom and $R^2$ is a moiety resulting from the thiol-ene reaction of a reactive thiol group with a reactive ene group, wherein the reactive ene group is norborn-2-en-5-yl. As will be understood by one skilled in the art, there are a number of ways to add a C—C moiety to the $R^2$ group. These methods may result in a linker group between the ene/yne-bearing moiety and the ene/yne functional group, such as, for non-limiting example, an amide functionality, ester functionality or a combination thereof. In one embodiment, a PEG is modified with 5-norbornene-2-carboxylic acid such that one or more terminal norbornene moiety (norborn-2-en-5-yl) is added to the PEG via an ester linkage. In another embodiment, PEG amine is modified with NHS-Norbornene such that one or more terminal norbornene moiety (norborn-2-en-5-yl) is added to the PEG via an amide linkage. In some embodiments, each C—C moiety between the sulfur atom and $R^2$ is a moiety independently selected from the group consisting of —$CH_2$—$CH_2$—$CH_2$—C(=O)—, —$CH_2$—$CH_2$—OC(=O)—, —$CH_2$—$CH_2$—S(=O)$_2$—, —$CH_2$—$CH_2$—O—, —($C_2$-$C_6$)-alkanediyl-, —$CH_2$—$CH_2$—C(=O)O—, —$CH_2$—CH($CH_3$)—C(=O)O—, —$CH_2$—$CH_2$—C(=O)NH—, —CH($CH_3$)—$CH_2$—O—, —$CH_2$—$CH_2$—$CH_2$—O—, —$CH_2$—$CH_2$—NHC(=O)—,

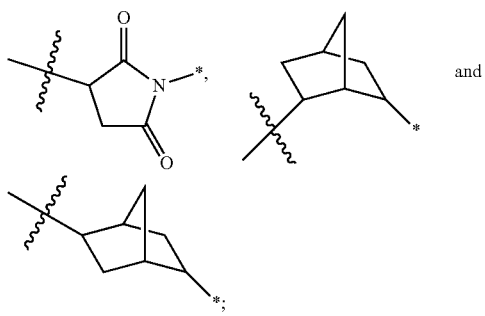

and wherein the first dash (—C—C) or wavy line represents bonding to the sulfur atom and the second dash (C—C—) or bonding to the $R^2$ group which may be a direct bond or via a linker moiety, such as, for non-limiting example, an amide functionality, ester functionality or a combination thereof. It will be appreciated that such C—C moieties are derived from an ene group comprising a moiety selected from the group consisting of vinylacetyl, vinyl ester, vinylsulfonyl, vinyl ether, allyl, acrylate ester, methacrylate ester, acrylamido, maleimido, propenyl ether, allyl ether, alkenyl, unsaturated ester, dienyl, N-vinylcarbamoyl and norborn-2-en-5-yl.

$R^1$ and $R^2$ can vary in size depending upon desired properties for the resulting polymeric material. More particularly, the molecular weight for $R^1$ and $R^2$ can range from about 30 Da to about 50000 Da. Prior to formation of the polymeric material of the present invention, $R^1$ can be derivatized to include two or more reactive thiol groups and $R^2$ can be derivatized to include three or more reactive ene group such that they can participate in photo-initiated thiol-ene polymerization that they can participate in photo-initiated thiol-ene polymerization. Thiolated macromers such as poly(ethylene glycol) dithiol are available commercially. The reactive ene groups can be selected from any suitable compound having a carbon-carbon double bond. For example, the reactive ene group can be selected from any suitable ethylenically unsaturated group such as, but not limited to, vinylacetyl, vinyl ester, vinylsulfonyl, vinyl ether, allyl, acrylate ester, methacrylate ester, acrylamido, maleimido, propenyl ether, allyl ether, alkenyl, unsaturated ester, dienyl, N-vinylcarbamoyl and norborn-2-en-5-yl. Thus, it will be appreciated that in the repeating unit shown above, the carbons can be $CH_2$ or can be substituted at one or more than one of the carbons within the repeating group, even including ring structures incorporating a double bond. If $R^1$ is derivatized with two reactive thiol and $R^2$ is derivatized with two reactive ene groups, the resulting thiol-ene polymer would be a linear copolymer composed of alternating $R^1$ and $R^2$ segments. However, the thiol-ene polymeric material is preferably formed to contain cross-linking and branching. Thus, the derivatized $R^1$ and $R^2$ segments preferably have more than two reactive thiol groups or reactive ene groups per molecule that can participate in crosslinking and polymerization. The extent of the branching and cross-linking can be controlled by the use of differently derivatized $R^1$ and $R^2$ segments and control over the concentration of the starting materials. In some embodiments, $R^1$ is a polypeptide of formula —$C_t$—$R^{1b}$—$C_t$, wherein $R^{1b}$ is a polypeptide, t≥1 and $C_t$ is a linker comprising at least one carbon atom, wherein each residue of $R^{1b}$ comprising a $C_t$ linker may be selected from the group consisting of a natural amino acid residue, a rare amino acid residue, an unnatural amino acid residue, an amino acid analog residue or an amino acid mimetic residue, provided that the natural amino acid residue comprising the $C_t$ linker is not a cysteine residue. In some embodiments, the unnatural amino acid residue is a thiol substituted beta amino acid residue, a thiol substituted gamma amino acid residue, a thiol substituted delta amino acid residue or a thiol substituted epsilon amino acid residue. In some embodiments, the amino acid analog residue or amino acid mimetic residue is derived from a natural amino acid residue or unnatural amino acid residue in which the carbonyl functionality is replaced by a methylene moiety. In some embodiments, the amino acid analog residue or the amino acid mimetic residue is derived from a natural amino acid residue or unnatural amino acid residue in which the amino functionality is replaced by a methylene moiety. In some embodiments, $C_t$ is selected from the group consisting of ($C_2$-$C_6$)alkanediyl-, —C(=O)—($C_1$-$C_6$)-alkanediyl- and —C(=O)—($C_1$-$C_6$)-alkanediyl-(O—$CH_2CH_2$)$_z$— where z is an integer from 1-10,000. In some embodiments, $C_t$ may be further substituted with one or more substituents selected from halo, alkyl, and alkoxy.

In some embodiments of formula (B), Q is a polymeric moiety of formula (Qb):

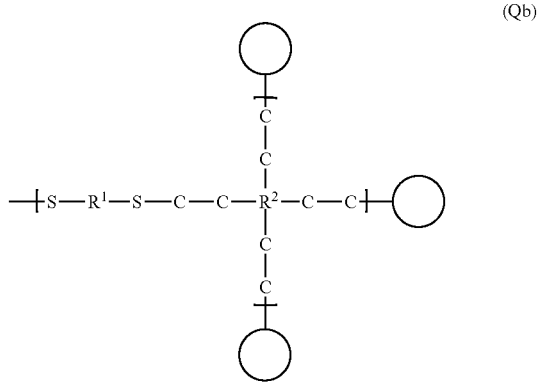

(Qb)

wherein, $R^1$ and $R^2$ are independently selected from the group consisting of poly(lactic acid) (PLA); polyglycolide (PGA); a copolymer of PLA and PGA (PLGA); poly(vinyl alcohol) (PVA); poly(ethylene glycol) (PEG); poly(ethylene oxide); a poly(ethylene oxide)-co-poly(propylene oxide) block copolymer; a poloxamine; a polyanhydride; a polyorthoester; a poly(hydroxy acids); a polydioxanone; a polycarbonate; a polyaminocarbonate; a poly(vinyl pyrrolidone); a poly(ethyl oxazoline); a polyurethane; a carboxymethyl cellulose; a hydroxyalkylated cellulose; a polypeptide; a nucleic acid; a modified nucleic acid; a locked nucleic acid; a polysaccharide; a carbohydrate; heparan sulfate; chondroitin sulfate; heparin, alginate; and a combination thereof; and wherein —O represents a point of attachment to either one of the sulfur atom of one of the P—$C_t$—S— moieties of formula (B) or a thioether moiety of another subunit of the polymeric moiety of formula (Qb). In some embodiments, $R^1$ is a polypeptide of formula —$C_t$—$R^{1a}$—$C_t$—, wherein $R^{1a}$ is a polypeptide, t≥2 and $C_t$ is a linker comprising at least two carbon atoms. In some embodiments, $C_t$ is selected from the group consisting of ($C_2$-$C_6$)alkanediyl-, —C(=O)—($C_1$-$C_6$)-alkanediyl- and —C(=O)—($C_1$-$C_6$)-alkanediyl-(O—$CH_2CH_2$)$_z$— where z is an integer from 1-10,000. In some embodiments, $C_t$ may be further substituted with one or more substituents selected from halo, alkyl, and alkoxy. As is understood by a person of skill in the art, each C—C moiety between the sulfur atom and $R^2$ is a moiety resulting from the thiol-ene reaction of a reactive thiol group with a reactive ene group, such as a reactive ene group independently selected from the group consisting of vinylacetyl, vinyl ester, vinylsulfonyl, vinyl ether, allyl, acrylate ester, methacrylate ester, acrylamido, maleimido, propenyl ether, allyl ether, alkenyl, unsaturated ester, dienyl, N-vinylcarbamoyl and norborn-2-en-5-yl. In some embodiments, the C—C moiety between the sulfur atom and $R^2$ is a moiety resulting from the thiol-ene reaction of a reactive thiol group with a reactive ene group, wherein the reactive ene group is norborn-2-en-5-yl. As will be understood by one skilled in the art, there are a number of ways to add a C—C moiety to the $R^2$ group. These methods may result in a linker group between the ene/yne-bearing moiety and the ene/yne functional group, such as, for non-limiting example, an amide functionality, ester functionality or a combination thereof. In one embodiment, a PEG is modified with 5-norbornene-2-carboxylic acid such that one or more terminal norbornene moiety (norborn-2-en-5-yl) is added to the PEG via an ester linkage. In another embodiment, PEG amine is modified with NHS-Norbornene such that one or more terminal norbornene moiety (norborn-2-en-5-yl) is added to the PEG via an amide linkage. In some embodiments, each C—C moiety between the sulfur atom and $R^2$ is a moiety independently selected from the group consisting of —$CH_2$—$CH_2$—$CH_2$—C(=O)—, —$CH_2$—$CH_2$—OC(=O)—, —$CH_2$—$CH_2$—S(=O)$_2$—, —$CH_2$—$CH_2$—O—, —($C_2$-$C_6$)-alkanediyl-, —$CH_2$—$CH_2$—C(=O)O—, —$CH_2$—CH($CH_3$)—C(=O)O—, —$CH_2$—$CH_2$—C(=O)NH—, —CH($CH_3$)—$CH_2$—O—, —$CH_2$—$CH_2$—$CH_2$—O—, —$CH_2$—$CH_2$—NHC(=O)—,

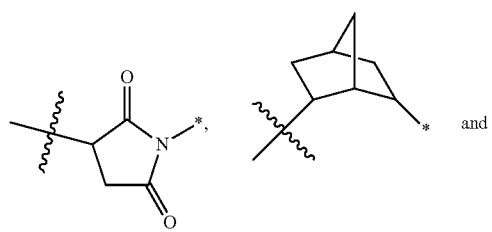

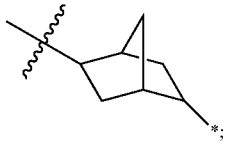

wherein the first dash (—C—C) or wavy line represents bonding to the sulfur atom and the second dash (C—C—) or bonding to the $R^2$ group which may be a direct bond or via a linker moiety, such as, for non-limiting example, an amide functionality, ester functionality or a combination thereof. It will be appreciated that such C—C moieties are derived from an ene group comprising a moiety selected from the group consisting of vinylacetyl, vinyl ester, vinylsulfonyl, vinyl ether, allyl, acrylate ester, methacrylate ester, acrylamido, maleimido, propenyl ether, allyl ether, alkenyl, unsaturated ester, dienyl, N-vinylcarbamoyl and norborn-2-en-5-yl. In some embodiments, $R^1$ is a polypeptide of formula —$C_t$—$R^{1b}$—$C_t$—, wherein $R^{1b}$ is a polypeptide, t≥1 and $C_t$ is a linker comprising at least one carbon atom, wherein each residue of $R^{1b}$ comprising a $C_t$ linker may be selected from the group consisting of a natural amino acid residue, a rare amino acid residue, an unnatural amino acid residue, an amino acid analog residue or an amino acid mimetic residue, provided that the natural amino acid residue comprising the $C_t$ linker is not a cysteine residue. In some embodiments, the unnatural amino acid residue is a thiol substituted beta amino acid residue, a thiol substituted gamma amino acid residue, a thiol substituted delta amino acid residue or a thiol substituted epsilon amino acid residue. In some embodiments, the amino acid analog residue or amino acid mimetic residue is derived from a natural amino acid residue or unnatural amino acid residue in which the carbonyl functionality is replaced by a methylene moiety. In some embodiments, the amino acid analog residue or the amino acid mimetic residue is derived from a natural amino acid residue or unnatural amino acid residue in which the amino functionality is replaced by a methylene moiety. In some embodiments, $C_t$ is selected from the group consisting of ($C_2$-$C_6$)alkanediyl-, —C(=O)—($C_1$-$C_6$)-alkanediyl- and —C(=O)—($C_1$-$C_6$)-alkanediyl-(O—$CH_2CH_2$)$_z$— where z is an integer from 1-10,000. In some embodiments, $C_t$ may be further substituted with one or more substituents selected from halo, alkyl, and alkoxy.

$R^1$ and $R^2$ can vary in size depending upon desired properties for the resulting polymeric material. More particularly, the molecular weight for $R^1$ and $R^2$ can range from about 30 Da to about 50000 Da. Prior to formation of the polymeric material of the present invention, $R^1$ can be derivatized to include two or more reactive thiol groups and $R^2$ can be derivatized to include three or more reactive ene group such that they can participate in photo-initiated thiol-ene polymerization that they can participate in photo-initiated thiol-ene polymerization. Thiolated macromers such as poly(ethylene glycol) dithiol are available commercially. The reactive ene groups can be selected from any suitable compound having a carbon-carbon double bond. For example, the reactive ene group can be selected from any suitable ethylenically unsaturated group such as, but not limited to, vinylacetyl, vinyl ester, vinylsulfonyl, vinyl ether, allyl, acrylate ester, methacrylate ester, acrylamido, maleimido, propenyl ether, allyl ether, alkenyl, unsaturated ester, dienyl, N-vinylcarbamoyl and norborn-2-en-5-yl. Thus, it will be appreciated that in the repeating unit shown above, the carbons can be $CH_2$ or can be substituted at one or more than one of the carbons within the repeating group, even including ring structures incorporating a double bond. If $R^1$ is derivatized with two reactive thiol and $R^2$ is derivatized with two reactive ene groups, the resulting thiol-ene polymer would be a linear copolymer composed of alternating $R^1$ and $R^2$ segments. However, the thiol-ene polymeric material is preferably formed to contain cross-linking and branching. Thus, the derivatized $R^1$ and $R^2$ segments preferably have more than two reactive thiol groups or reactive ene groups per molecule that can participate in crosslinking and polymerization. The extent of the branching and cross-linking can be controlled by the use of differently derivatized $R^1$ and $R^2$ segments and control over the concentration of the starting materials.

Also provided is a polymeric material (e.g. a thiol-ene hydrogel) comprising repeating units of the formula (I):

$$\{S-C_t-X-C_t-S-C-C-Y-C-C\} \quad (I)$$

wherein X is a polypeptide, $t \geq 2$, $C_t$ is a linker comprising at least two carbon atoms (i.e., X is linked to at least two thioether moieties via a linker of two carbon atoms in length or longer), and Y is selected from the group consisting of poly(lactic acid) (PLA); polyglycolide (PGA); a copolymer of PLA and PGA (PLGA); poly(vinyl alcohol) (PVA); poly(ethylene glycol) (PEG); poly(ethylene oxide); a poly (ethylene oxide)-co-poly(propylene oxide) block copolymer; a poloxamine; a polyanhydride; a polyorthoester; a poly(hydroxy acids); a polydioxanone; a polycarbonate; a polyaminocarbonate; a poly(vinyl pyrrolidone); a poly(ethyl oxazoline); a polyurethane; a carboxymethyl cellulose; a hydroxyalkylated cellulose; a polypeptide; a nucleic acid; a modified nucleic acid; a locked nucleic acid; a polysaccharide; a carbohydrate; heparan sulfate; chondroitin sulfate; heparin, alginate; and a combination thereof. In some embodiments, $C_t$ is selected from the group consisting of $(C_2-C_6)$alkanediyl-, $-C(=O)-(C_1-C_6)$-alkanediyl- and $-C(=O)-(C_1-C_6)$-alkanediyl-$(O-CH_2CH_2)_z-$ where z is an integer from 1-10,000. In some embodiments, $C_t$ may be further substituted with one or more substituents selected from halo, alkyl, and alkoxy. As is understood by a person of skill in the art, each C—C moiety between the sulfur atom and Y is a moiety resulting from the thiol-ene reaction of a reactive thiol group with a reactive ene group, such as a reactive ene group independently selected from the group consisting of vinylacetyl, vinyl ester, vinylsulfonyl, vinyl ether, allyl, acrylate ester, methacrylate ester, acrylamido, maleimido, propenyl ether, allyl ether, alkenyl, unsaturated ester, dienyl, N-vinylcarbamoyl and norborn-2-en-5-yl. In some embodiments, the C—C moiety between the sulfur atom and Y is a moiety resulting from the thiol-ene reaction of a reactive thiol group with a reactive ene group, wherein the reactive ene group is norborn-2-en-5-yl. As will be understood by one skilled in the art, there are a number of ways to add a C—C moiety to the Y group. These methods may result in a linker group between the ene/yne-bearing moiety and the ene/yne functional group, such as, for non-limiting example, an amide functionality, ester functionality or a combination thereof. In one embodiment, a PEG is modified with 5-norbornene-2-carboxylic acid such that one or more terminal norbornene moiety (norborn-2-en-5-yl) is added to the PEG via an ester linkage. In another embodiment, PEG amine is modified with NHS-Norbornene such that one or more terminal norbornene moiety (norborn-2-en-5-yl) is added to the PEG via an amide linkage. In some embodiments, each C—C moiety between the sulfur atom and Y is a moiety independently selected from the group consisting of $-CH_2-CH_2-CH_2-C(=O)-$, $-CH_2-CH_2-OC(=O)-$, $-CH_2-CH_2-S(=O)_2-$, $-(C_2-C_6)$-alkanediyl-, $-CH_2-CH_2-C(=O)O-$, $-CH_2-CH(CH_3)-C(=O)O-$, $-CH_2-CH_2-C(=O)NH-$, $-CH(CH_3)-CH_2-O-$, $-CH_2-CH_2-CH_2-O-$, $-CH_2-CH_2-NHC(=O)-$,

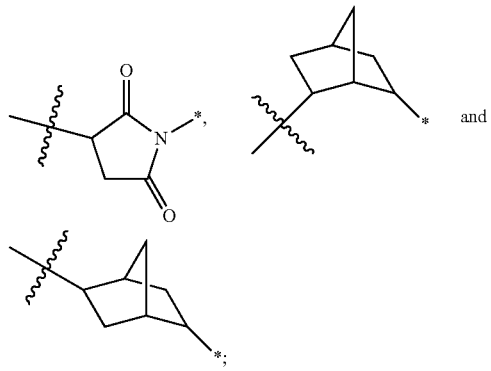

wherein the first dash (—C—C) or wavy line represents bonding to the sulfur atom and the second dash (C—C—) or bonding to the Y group which may be a direct bond or via a linker moiety, such as, for non-limiting example, an amide functionality, ester functionality or a combination thereof. It will be appreciated that such C—C moieties are derived from an ene group comprising a moiety selected from the group consisting of vinylacetyl, vinyl ester, vinylsulfonyl, vinyl ether, allyl, acrylate ester, methacrylate ester, acrylamido, maleimido, propenyl ether, allyl ether, alkenyl, unsaturated ester, dienyl, N-vinylcarbamoyl and norborn-2-en-5-yl.

Also provided is a polymeric material [e.g. to a thiol-ene hydrogel] comprising repeating units of the formula (II):

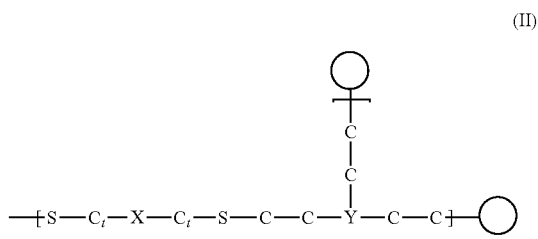

(II)

wherein X is a polypeptide, $t \geq 2$, $C_t$ is a linker comprising at least two carbon atoms (i.e., X is linked to at least two thioether moieties via a linker of two carbon atoms in length or longer), and Y is selected from the group consisting of poly(lactic acid) (PLA); polyglycolide (PGA); a copolymer of PLA and PGA (PLGA); poly(vinyl alcohol) (PVA); poly(ethylene glycol) (PEG); poly(ethylene oxide); a poly (ethylene oxide)-co-poly(propylene oxide) block copolymer; a poloxamine; a polyanhydride; a polyorthoester; a poly(hydroxy acids); a polydioxanone; a polycarbonate; a polyaminocarbonate; a poly(vinyl pyrrolidone); a poly(ethyl oxazoline); a polyurethane; a carboxymethyl cellulose; a hydroxyalkylated cellulose; a polypeptide; a nucleic acid; a modified nucleic acid; a locked nucleic acid; a polysaccharide; a carbohydrate; heparan sulfate; chondroitin sulfate; heparin, alginate; and a combination thereof; wherein —O represents a point of attachment to a thioether moiety of another subunit of the polymeric moiety of formula (II).

In some embodiments, $C_t$ is selected from the group consisting of $(C_2$-$C_6)$alkanediyl-, —C(=O)—$(C_1$-$C_6)$-alkanediyl- and —C(=O)—$(C_1$-$C_6)$-alkanediyl-(O—$CH_2CH_2)_z$— where z is an integer from 1-10,000. In some embodiments, $C_t$ may be further substituted with one or more substituents selected from halo, alkyl, and alkoxy. As is understood by a person of skill in the art, each C—C moiety between the sulfur atom and Y is a moiety resulting from the thiol-ene reaction of a reactive thiol group with a reactive ene group, such as a reactive ene group independently selected from the group consisting of vinylacetyl, vinyl ester, vinylsulfonyl, vinyl ether, allyl, acrylate ester, methacrylate ester, acrylamido, maleimido, propenyl ether, allyl ether, alkenyl, unsaturated ester, dienyl, N-vinylcarbamoyl and norborn-2-en-5-yl. In some embodiments, the C—C moiety between the sulfur atom and Y is a moiety resulting from the thiol-ene reaction of a reactive thiol group with a reactive ene group, wherein the reactive ene group is norborn-2-en-5-yl. As will be understood by one skilled in the art, there are a number of ways to add a C—C moiety to the Y group. These methods may result in a linker group between the ene/yne-bearing moiety and the ene/yne functional group, such as, for non-limiting example, an amide functionality, ester functionality or a combination thereof. In one embodiment, a PEG is modified with 5-norbornene-2-carboxylic acid such that one or more terminal norbornene moiety (norborn-2-en-5-yl) is added to the PEG via an ester linkage. In another embodiment, PEG amine is modified with NHS-Norbornene such that one or more terminal norbornene moiety (norborn-2-en-5-yl) is added to the PEG via an amide linkage. In some embodiments, each C—C moiety between the sulfur atom and Y is a moiety independently selected from the group consisting of —$CH_2$—$CH_2$—$CH_2$—C(=O)—, —$CH_2$—$CH_2$—OC(=O)—, —$CH_2$—$CH_2$—S(=O)$_2$—, —$CH_2$—$CH_2$—O—, —$(C_2$-$C_6)$-alkanediyl-, —$CH_2$—$CH_2$—C(=O)O—, —$CH_2$—CH$(CH_3)$—C(=O)O—, —$CH_2$—$CH_2$—C(=O)NH—, —CH$(CH_3)$—$CH_2$—O—, —$CH_2$—$CH_2$—$CH_2$—O—, —$CH_2$—$CH_2$—NHC(=O)—,

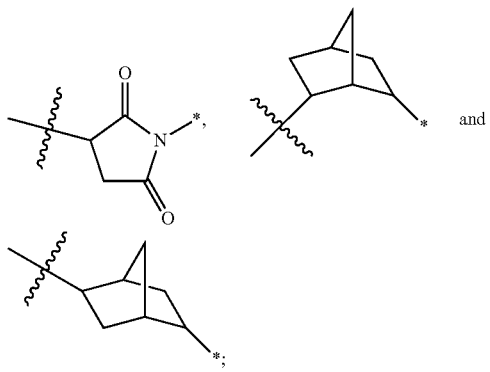

wherein the first dash (—C—C) or wavy line represents bonding to the sulfur atom and the second dash (C—C—) or bonding to the Y group which may be a direct bond or via a linker moiety, such as, for non-limiting example, an amide functionality, ester functionality or a combination thereof. It will be appreciated that such C—C moieties are derived from an ene group comprising a moiety selected from the group consisting of vinylacetyl, vinyl ester, vinylsulfonyl, vinyl ether, allyl, acrylate ester, methacrylate ester, acrylamido, maleimido, propenyl ether, allyl ether, alkenyl, unsaturated ester, dienyl, N-vinylcarbamoyl and norborn-2-en-5-yl.

Also provided is a polymeric material [e.g. to a thiol-ene hydrogel] comprising repeating units of the formula (III):

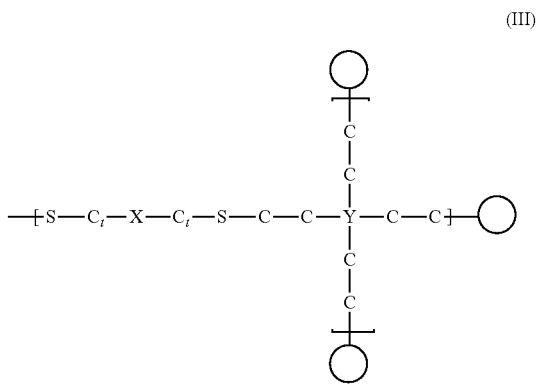

(III)

wherein X is a polypeptide, t≥2, $C_t$ is a linker comprising at least two carbon atoms (i.e., X is linked to at least two thioether moieties via a linker of two carbon atoms in length or longer), and Y is selected from the group consisting of poly(lactic acid) (PLA); polyglycolide (PGA); a copolymer of PLA and PGA (PLGA); poly(vinyl alcohol) (PVA); poly(ethylene glycol) (PEG); poly(ethylene oxide); a poly(ethylene oxide)-co-poly(propylene oxide) block copolymer; a poloxamine; a polyanhydride; a polyorthoester; a poly(hydroxy acids); a polydioxanone; a polycarbonate; a polyaminocarbonate; a poly(vinyl pyrrolidone); a poly(ethyl oxazoline); a polyurethane; a carboxymethyl cellulose; a hydroxyalkylated cellulose; a polypeptide; a nucleic acid; a modified nucleic acid; a locked nucleic acid; a polysaccharide; a carbohydrate; heparan sulfate; chondroitin sulfate; heparin, alginate; and a combination thereof; wherein —○ represents a point of attachment to a thioether moiety of another subunit of the polymeric moiety of formula (III). In some embodiments, $C_t$ is selected from the group consisting of $(C_2$-$C_6)$alkanediyl-, —C(=O)—$(C_1$-$C_6)$-alkanediyl- and —C(=O)—$(C_1$-$C_6)$-alkanediyl-(O—$CH_2CH_2)_z$— where z is an integer from 1-10,000. In some embodiments, $C_t$ may be further substituted with one or more substituents selected from halo, alkyl, and alkoxy. As is understood by a person of skill in the art, each C—C moiety between the sulfur atom and Y is a moiety resulting from the thiol-ene reaction of a reactive thiol group with a reactive ene group, such as a reactive ene group independently selected from the group consisting of vinylacetyl, vinyl ester, vinylsulfonyl, vinyl ether, allyl, acrylate ester, methacrylate ester, acrylamido, maleimido, propenyl ether, allyl ether, alkenyl, unsaturated ester, dienyl, N-vinylcarbamoyl and norborn-2-en-5-yl. In some embodiments, the C—C moiety between the sulfur atom and Y is a moiety resulting from the thiol-ene reaction of a reactive thiol group with a reactive ene group, wherein the reactive ene group is norborn-2-en-5-yl. As will be understood by one skilled in the art, there are a number of ways to add a C—C moiety to the Y group. These methods may result in a linker group between the ene/yne-bearing moiety and the ene/yne functional group, such as, for non-limiting example, an amide functionality, ester functionality or a combination thereof. In one embodiment, a PEG is modified with 5-norbornene-2-carboxylic acid such that one or more terminal norbornene moiety (norborn-2-en-5-yl) is added to the PEG via an ester linkage. In another embodiment, PEG amine is modified with NHS-Norbornene such that one or more terminal norbornene moiety (norborn-2-en-5-yl) is added to the PEG via an amide linkage. In some embodiments, each C—C moiety between the sulfur atom and Y is a moiety independently selected from the group consisting of —CH$_2$—CH$_2$—CH$_2$—C(=O)—, —CH$_2$—CH$_2$—OC(=O)—, —CH$_2$—CH$_2$—S(=O)$_2$—, —CH$_2$—CH$_2$—O—, —(C$_2$-C$_6$)-alkanediyl-, —CH$_2$—CH$_2$—C(=O)O—, —CH$_2$—CH(CH$_3$)—C(=O)O—, —CH$_2$—CH$_2$—C(=O)NH—, —CH(CH$_3$)—CH$_2$—O—, —CH$_2$—CH$_2$—CH$_2$—O—, —CH$_2$—CH$_2$—NHC(=O)—,

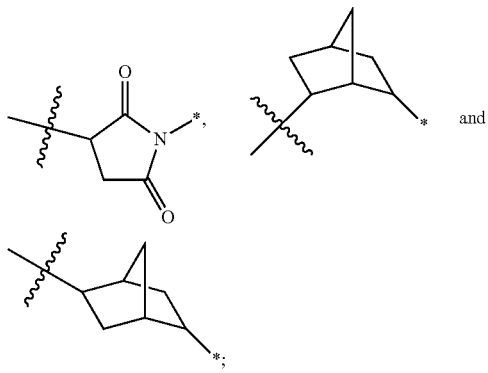

wherein the first dash (—C—C) or wavy line represents bonding to the sulfur atom and the second dash (C—C—) or bonding to the Y group which may be a direct bond or via a linker moiety, such as, for non-limiting example, an amide functionality, ester functionality or a combination thereof. It will be appreciated that such C—C moieties are derived from an ene group comprising a moiety selected from the group consisting of vinylacetyl, vinyl ester, vinylsulfonyl, vinyl ether, allyl, acrylate ester, methacrylate ester, acrylamido, maleimido, propenyl ether, allyl ether, alkenyl, unsaturated ester, dienyl, N-vinylcarbamoyl and norborn-2-en-5-yl.

In some embodiments, the polymeric material of formula (I), (II) or (III) may further comprise a biologically active component associated with the polymer matrix of the polymeric material. In some of these embodiments, the biologically active component is encapsulated in the polymer matrix. In some of these embodiments, the biologically active component is covalently bound to (e.g., incorporated into or attached onto) the polymer matrix. This biologically active component may be any of applicable biologically active component described herein, such as a tissue, a cell, a protein, a peptide, a small molecule drug, a nucleic acid, an encapsulated nucleic acid (for example encapsulated in a lipid nanoparticle), a lipid, a carbohydrate, or an agricultural compound described herein.

It will be appreciated that in the repeating unit shown in formulae (A), (B), (I), (II) and (III), the carbon atoms can be CH$_2$ or can be substituted at one or more than one of the carbons within the repeating group, even including ring structures incorporating a double bond. Further, it will be appreciated that in order to derivatize the biological active compound with the ene/yne, there may be one or more linking groups between the biologically active compound and the carbon.

When a thiol-containing polypeptide comprising one or more reactive thiol group reacts with an ene compound that contains only one reactive ene group, the polypeptide is modified to carry one or more "terminal" moieties derived from the ene containing compound as each ene containing compound is capable of reacting with only one reactive thiol group.

Thus provided is a compound of formula (C):

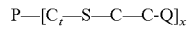

P—[C$_t$—S—C—C-Q]$_x$ wherein P is a polypeptide, C$_t$ is a linker comprising at least one carbon atom, t≥1, x is 1 or an integer greater than 1 and Q is a biological active component (e.g., a drug, a toxin or a pesticide), a polymer moiety (e.g., PEG), a capture moiety (e.g., biotin), a label (e.g., a fluorescent label, a chromophore, or a fluorophore), a sugar or carbohydrate, a nucleic acid, or a second polypeptide and wherein each residue of P comprising a C$_t$ linker may be selected from the group consisting of a natural amino acid residue, a rare amino acid residue, an unnatural amino acid residue, an amino acid analog residue or an amino acid mimetic residue, provided that the natural amino acid residue comprising the C$_t$ linker is not a cysteine residue. In some embodiments, the unnatural amino acid residue is a thiol substituted beta amino acid residue, a thiol substituted gamma amino acid residue, a thiol substituted delta amino acid residue or a thiol substituted epsilon amino acid residue. In some embodiments, the amino acid analog residue or amino acid mimetic residue is derived from a natural amino acid residue or unnatural amino acid residue in which the carbonyl functionality is replaced by a methylene moiety. In some embodiments, the amino acid analog residue or the amino acid mimetic residue is derived from a natural amino acid residue or unnatural amino acid residue in which the amino functionality is replaced by a methylene moiety. In some embodiments, C$_t$ is selected from the group consisting of (C$_2$-C$_6$)alkanediyl-, —C(=O)—(C$_1$-C$_6$)-alkanediyl- and —C(=O)—(C$_1$-C$_6$)-alkanediyl-(O—CH$_2$CH$_2$)$_z$— where z is an integer from 1-10,000. In some embodiments, C$_t$ may be further substituted with one or more substituents selected from halo, alkyl, and alkoxy. As is understood by a person of skill in the art, the C—C moiety between the sulfur atom and Q is a moiety resulting from the thiol-ene reaction of a reactive thiol group with a reactive ene group, such as a reactive ene group selected from the group consisting of vinylacetyl, vinyl ester, vinylsulfonyl, vinyl ether, allyl, acrylate ester, methacrylate ester, acrylamido, maleimido, propenyl ether, allyl ether, alkenyl, unsaturated ester, dienyl, N-vinylcarbamoyl and norborn-2-en-5-yl. In some embodiments, the C—C moiety between the sulfur atom and Q is a moiety resulting from the thiol-ene reaction of a reactive thiol group with a reactive ene group, wherein the reactive ene group is norborn-2-en-5-yl. As will be understood by one skilled in the art, there are a number of ways to add a C—C moiety to the Q group. These methods may result in a linker group between the ene/yne-bearing moiety and the ene/yne functional group, such as, for non-limiting example, an amide functionality, ester functionality or a combination thereof. In one embodiment, a PEG is modified with 5-norbornene-2-carboxylic acid such that one or more terminal norbornene moiety (norborn-2-en-5-yl) is added to the PEG via an ester linkage. In another embodiment, PEG amine is modified with NHS-Norbornene such that one or more terminal norbornene moiety (norborn-2-en-5-yl) is added to the PEG via an amide linkage. In some embodiments, the C—C moiety between the sulfur atom and Q is a moiety selected from the group consisting of —CH$_2$—CH$_2$—

CH₂—C(=O)—, —CH₂—CH₂—OC(=O)—, —CH₂—CH₂—S(=O)₂—, —CH₂—CH₂—O—, —(C₂-C₆)-alkanediyl-, —CH₂—CH₂—C(=O)O—, —CH₂—CH(CH₃)—C(=O)O—, —CH₂—CH₂—C(=O)NH—, —CH(CH₃)—CH₂—O—, —CH₂—CH₂—CH₂—O—, —CH₂—CH₂—NHC(=O)—,

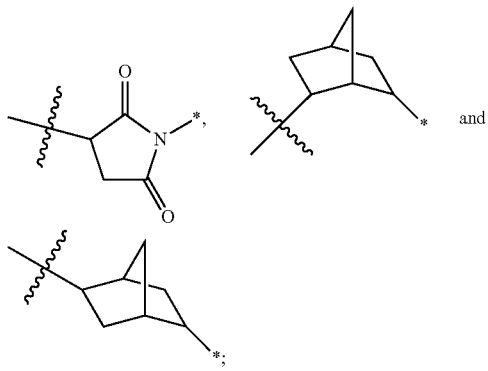

wherein the first dash (—C—C) or wavy line represents bonding to the sulfur atom and the second dash (C—C—) or bonding to the Q group which may be a direct bond or via a linker moiety, such as, for non-limiting example, an amide functionality, ester functionality or a combination thereof. It will be appreciated that such C—C moieties are derived from an ene group comprising a moiety selected from the group consisting of vinylacetyl, vinyl ester, vinylsulfonyl, vinyl ether, allyl, acrylate ester, methacrylate ester, acrylamido, maleimido, propenyl ether, allyl ether, alkenyl, unsaturated ester, dienyl, N-vinylcarbamoyl and norborn-2-en-5-yl.

In such embodiments, polypeptide P is linked to one or more thioether moieties via a linker of two carbon atoms in length or longer. Each thioether moiety is also attached to a Q moiety via the ethylene unit derived from the ene group.

In some embodiments of formula (C), P can be selected from peptide and protein hormones, growth factors, cytokines, interleukins, receptors, solubilized receptors, therapeutic proteins, enzymes, and structural proteins. Growth factors may include AM, Ang, BMP, BDNF, GDNF, GCSF, GM-CSF, GDF, HGF, HDGF, KGF, MSF, NGF, TPO, FBS, EPO, IGF, EGF, FGF, TGF, PDGF and interleukins including their derivatives and family members. Structural proteins include fibrin, fibrinogen, fibronectins, keratins, actins, laminins and collagens.

In some embodiments of formula (C), the polypeptide P further comprises a peptide sequence known to be sensitive to a protease. In another embodiment, the polypeptide is an active thiol-flanked plasmin degradable peptide. In another, two plasmin degradable sequences are included within the peptide. In a particular embodiment, the polypeptide is a homocysteine-flanked matrix metalloproteinase (MMP) degradable peptide, to create a hydrogel network that is degraded by cell-secreted MMPs.

In some embodiments, x is 1, where one Q moiety is linked to the polypeptide P. In some embodiments, x is 2, 3, 4 or a greater integer.

In certain embodiments of the formula (C), the P moiety is selected from peptide and protein hormones, growth factors, cytokines, interleukins, receptors, solubilized receptors, therapeutic proteins, enzymes, and structural proteins. Growth factors may include AM, Ang, BMP, BDNF, GDNF, GCSF, GM-CSF, GDF, HGF, HDGF, KGF, MSF, NGF, TPO, FBS, EPO, IGF, EGF, FGF, TGF, PDGF and interleukins including their derivatives and family members. Structural proteins include fibrin, fibrinogen, fibronectins, keratins, actins, laminins and collagens.

In some embodiments, the Q moiety, which is linked to the polypeptide P, is chosen with respect to the specific functional property that the modification is sought to confer, for a non-limiting example, introduction of a fluorophore or chromophore, introduction of an affinity tag, introduction of enzymatic activity, introduction of a certain chemical moiety or moieties, introduction of a hydrophilic, hydrophobic or amphiphilic polymeric tail in order to manipulate solubility, pharmacokinetics, pharmacodynamics or interaction with biological membranes or solid surfaces, generation of a polypeptide-containing polymer or of a telechelic monomer for further polymerization etc., and may include appropriate derivatives of the following (non-limiting example): poly(lactic acid) (PLA), polyglycolide (PGA), copolymers of PLA and PGA (PLGA), poly(vinyl alcohol) (PVA), poly(ethylene glycol) (PEG), poly(ethylene oxide), poly(ethylene oxide)-co-poly(propylene oxide) block copolymers (poloxamers, meroxapols), poloxamines, polyanhydrides, polyorthoesters, poly(hydroxy acids), polydioxanones, polycarbonates, polyaminocarbonates, poly(vinyl pyrrolidone), poly(ethyl oxazoline), a polyurethane, carboxymethyl cellulose, hydroxyalkylated celluloses such as hydroxyethyl cellulose and methylhydroxypropyl cellulose, and natural polymers such as polypeptides, polysaccharides or carbohydrates such as polysucrose, hyaluronic acid, dextran and similar derivatives thereof, heparan sulfate, chondroitin sulfate, heparin, or alginate, and proteins such as gelatin, collagen, albumin, or ovalbumin, fibrinogen, fibrin, laminin, fibronectin, vitronectin, fluorescent proteins such as green fluorescent protein or its analogs, fluorescent and non-fluorescent dyes, fluorescence quenchers, high-affinity tags, such as polypeptide tags (His-tag, FLAG-tag and others), antibodies and fragments thereof, nucleic acid aptamers, oligonucleotides and polynucleotides, high-order macromolecular assemblies such as ribonucleoproteins, viral capsids etc. The reactive ene group of the second moiety may be selected from any suitable ethylenically unsaturated group such as, but not limited to, vinylacetyl, vinyl ester, vinylsulfonyl, vinyl ether, allyl, acrylate ester, methacrylate ester, acrylamido, maleimido, propenyl ether, allyl ether, alkenyl, unsaturated ester, dienyl, N-vinylcarbamoyl and norborn-2-en-5-yl. The Q moiety, which is linked to the polypeptide P, may comprise a polymeric moiety such as, but not limited to, poly(lactic acid) (PLA); polyglycolide (PGA); a copolymer of PLA and PGA (PLGA); poly(vinyl alcohol) (PVA); poly(ethylene glycol) (PEG); poly(ethylene oxide); a poly(ethylene oxide)-co-poly(propylene oxide) block copolymer; a poloxamine; a polyanhydride; a polyorthoester; a poly(hydroxy acids); a polydioxanone; a polycarbonate; a polyaminocarbonate; a poly(vinyl pyrrolidone); a poly(ethyl oxazoline); a polyurethane; a carboxymethyl cellulose; a hydroxyalkylated cellulose; a polypeptide; a nucleic acid; a modified nucleic acid; a locked nucleic acid; a polysaccharide; a carbohydrate; heparan sulfate; chondroitin sulfate; heparin, alginate; and a combination thereof. In some embodiments, the second moiety may comprise a biologically active component.

In certain embodiments of the formula (C), the Q moiety, which is linked to the polypeptide P, may comprise a biologically active component such as any one of the biologically active components described herein. In some embodiments, the Q moiety comprises a polymer, a capture moiety, a label, a carbohydrate, a nucleic acid, or a second polypeptide as described herein.

In some embodiments, the compound of formula (C) is produced by reacting a compound of formula P—[$C_t$—SH]$_x$ and a compound of formula $CH_2$=CH-Q and a radical initiator (such as a photoinitiator described herein), for example, under conditions described herein that promote a radical-mediated thiol-ene reaction, wherein P, $C_t$, t, Q and x are as defined for formula (C) or any variations thereof. In one aspect the $CH_2$=CH— moiety of $CH_2$=CH-Q is a reactive ene group selected from the group consisting of vinylacetyl, vinyl ester, vinylsulfonyl, vinyl ether, allyl, acrylate ester, methacrylate ester, acrylamido, allyl ether, alkenyl, unsaturated ester, dienyl, and N-vinylcarbamoyl.

It is understood that $CH_2$=CH-Q represents an ene group bearing a terminal, unsubstituted alkene moiety, but that substituted alkenes may also be employed and are also described herein. Thus, it will be appreciated that the compound of formula (C) in which the C—C moiety is derived from an alkene other than a terminal, unsubstituted alkene is also provided and may be produced by reacting a compound of formula P—[$C_t$—SH]$_x$ and a compound of formula T-Q and a radical initiator (such as a photoinitiator described herein), wherein P, $C_t$, t, Q and x are as defined for formula (C) or any variations thereof and T indicates an alkene moiety other than a terminal, unsubstituted alkene moiety, under free radical-mediated reaction conditions. In one aspect, T-Q is a cyclic alkene moiety of the following formula

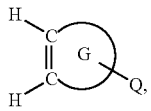

wherein ring G is a monocyclic or bicyclic cycloalkene, which can have one or more annular heteroatoms selected from O, S, and N, and which may be substituted with one or more substituents selected from the group consisting of oxo, halo, alkyl and alkoxy, and where the bicyclic cycloalkene may be a fused, bridged or a spiro bicyclic ring. It will be appreciated that Q may be directly attached to T or may be linked to T via a linker moiety, such as, for non-limiting example, an amide functionality, ester functionality or a combination thereof. Examples of T-Q include Q moieties derivatized with a maleimido group, a propenyl ether group, a norborn-2-en-5-yl group or any combination thereof, any one or more of which may be directly connected to Q or connected to Q via a linker moiety, such as, for non-limiting example, an amide functionality, ester functionality or a combination thereof.

In some embodiments, the T moiety of T-Q is norborn-2-en-5-yl. As will be understood by one skilled in the art, there are a number of ways to add a $CH_2$=CH— moiety to the Q group of $CH_2$=CH-Q or to add a T moiety to the Q group of T-Q. These methods may result in a linker group between the ene/yne-bearing moiety and the ene/yne functional group, such as, for non-limiting example, an amide functionality, ester functionality or a combination thereof. In a preferred embodiment, a PEG is modified with 5-norbornene-2-carboxylic acid such that terminal norbornene(s) (norborn-2-en-5-yl) will be added to the PEG via an ester linkage. In another embodiment, PEG amine is modified with NHS-Norbornene such that terminal norbornene(s) (norborn-2-en-5-yl) will be added to the PEG via an amide linkage. In some embodiments, the $CH_2$=CH— moiety of $CH_2$=CH-Q is a moiety selected from the group consisting of $CH_2$=CH—C(=O)—, $CH_2$=CH—S(=O)$_2$—, $CH_2$=CH—O—, $CH_2$=CH—($C_0$-$C_4$)-alkanediyl-, $CH_2$=CH—C(=O)O—, $CH_2$=C($CH_3$)—C(=O)O—, $CH_2$=CH—C(=O)NH—, $CH_2$=CH—$CH_2$—O—, and $CH_2$=CH—NHC(=O)—, and the T moiety of T-Q is selected from the group consisting of

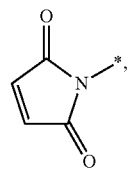

—CH($CH_3$)=CH—O— and

wherein the asterisk represents bonding to the Q group which may be a direct bond or via a linker moiety, such as, for non-limiting example, an amide functionality, ester functionality or a combination thereof.

In some embodiments, the compound of formula (C) is produced in a reduced oxygen environment or in the absence of oxygen, such as in the presence of a degassed solvent.

Also provided is a compound of formula (D):

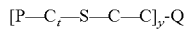

wherein P is a polypeptide, $C_t$ is a linker comprising at least one carbon atom, t≥1, wherein each residue of P comprising a $C_t$ linker may be selected from the group consisting of a natural amino acid residue, a rare amino acid residue, an unnatural amino acid residue, an amino acid analog residue or an amino acid mimetic residue, provided that the natural amino acid residue comprising the $C_t$ linker is not a cysteine residue; y is 1 or an integer greater than 1 (e.g. 2, 3, 4 or more) and Q is selected from the group consisting of poly(lactic acid) (PLA); polyglycolide (PGA); a copolymer of PLA and PGA (PLGA); poly(vinyl alcohol) (PVA); poly(ethylene glycol) (PEG); poly(ethylene oxide); a poly (ethylene oxide)-co-poly(propylene oxide) block copolymer; a poloxamine; a polyanhydride; a polyorthoester; a poly(hydroxy acids); a polydioxanone; a polycarbonate; a polyaminocarbonate; a poly(vinyl pyrrolidone); a poly(ethyl oxazoline); a polyurethane; a carboxymethyl cellulose; a hydroxyalkylated cellulose; a polypeptide; a nucleic acid; a modified nucleic acid; a locked nucleic acid; a polysaccharide; a carbohydrate; heparan sulfate; chondroitin sulfate; heparin, alginate; and a combination thereof. All variations of P, $C_t$, t and Q that are described for formula (C) are equally applicable to, and described for, formula (D) the same as if each and every description, variation, aspect or embodiment were specifically and individually listed for formula (D). That is, it is appreciated that formula (C) describes materials in which more than one —$C_t$—S—C—C-Q may be appended to a given P and that formula (D) describes materials in which more than one P—$C_t$—S—C—

C— may be appended to a given Q, but that the underlying P, $C_t$, t and Q may be the same in both formulae.

In some embodiments, the unnatural amino acid residue is a thiol substituted beta amino acid residue, a thiol substituted gamma amino acid residue, a thiol substituted delta amino acid residue or a thiol substituted epsilon amino acid residue. In some embodiments, the amino acid analog residue or amino acid mimetic residue is derived from a natural amino acid residue or unnatural amino acid residue in which the carbonyl functionality is replaced by a methylene moiety. In some embodiments, the amino acid analog residue or the amino acid mimetic residue is derived from a natural amino acid residue or unnatural amino acid residue in which the amino functionality is replaced by a methylene moiety. In some embodiments, $C_t$ is selected from the group consisting of $(C_2-C_6)$alkanediyl-, —C(=O)—$(C_1-C_6)$-alkanediyl- and —C(=O)—$(C_1-C_6)$-alkanediyl-(O—$CH_2CH_2$)$_z$— where z is an integer from 1-10,000. In some embodiments, $C_t$ may be further substituted with one or more substituents selected from halo, alkyl, and alkoxy. As is understood by a person of skill in the art, each C—C moiety between the sulfur atom and Q is a moiety resulting from the thiol-ene reaction of a reactive thiol group with a reactive ene group, such as a reactive ene group independently selected from the group consisting of vinylacetyl, vinyl ester, vinylsulfonyl, vinyl ether, allyl, acrylate ester, methacrylate ester, acrylamido, maleimido, propenyl ether, allyl ether, alkenyl, unsaturated ester, dienyl, N-vinylcarbamoyl and norborn-2-en-5-yl. In some embodiments, the C—C moiety between the sulfur atom and Q is a moiety resulting from the thiol-ene reaction of a reactive thiol group with a reactive ene group, wherein the reactive ene group is norborn-2-en-5-yl. As will be understood by one skilled in the art, there are a number of ways to add a C—C moiety to the Q group. These methods may result in a linker group between the ene/yne-bearing moiety and the ene/yne functional group, such as, for non-limiting example, an amide functionality, ester functionality or a combination thereof. In one embodiment, a PEG is modified with 5-norbornene-2-carboxylic acid such that one or more terminal norbornene moiety (norborn-2-en-5-yl) is added to the PEG via an ester linkage. In another embodiment, PEG amine is modified with NHS-Norbornene such that one or more terminal norbornene moiety (norborn-2-en-5-yl) is added to the PEG via an amide linkage. In some embodiments, each C—C moiety between the sulfur atom and Q is a moiety independently selected from the group consisting of —$CH_2$—$CH_2$—$CH_2$—C(=O)—, —$CH_2$—$CH_2$—OC(=O)—, —$CH_2$—$CH_2$—S(=O)$_2$—, —$CH_2$—$CH_2$—O—, —$(C_2-C_6)$-alkanediyl-, —$CH_2$—$CH_2$—C(=O)O—, —$CH_2$—CH($CH_3$)—C(=O)O—, —$CH_2$—$CH_2$—C(=O)NH—, —CH($CH_3$)—$CH_2$—O—, —$CH_2$—$CH_2$—$CH_2$—O—, —$CH_2$—$CH_2$—NHC(=O)—,

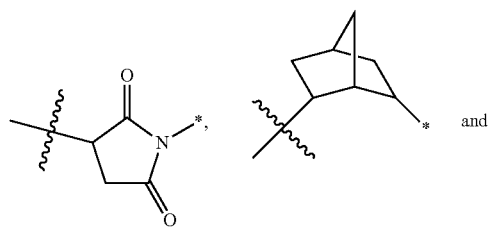

-continued

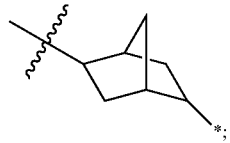

wherein the first dash (—C—C) or wavy line represents bonding to the sulfur atom and the second dash (C—C—) or bonding to the Q group which may be a direct bond or via a linker moiety, such as, for non-limiting example, an amide functionality, ester functionality or a combination thereof. It will be appreciated that such C—C moieties are derived from an ene group comprising a moiety selected from the group consisting of vinylacetyl, vinyl ester, vinylsulfonyl, vinyl ether, allyl, acrylate ester, methacrylate ester, acrylamido, maleimido, propenyl ether, allyl ether, alkenyl, unsaturated ester, dienyl, N-vinylcarbamoyl and norborn-2-en-5-yl.

In some embodiments, the compound of formula (D) is produced by reacting a compound of formula P—$C_t$—SH and a compound of formula $[CH_2=CH]_y$Q and a radical initiator (such as a photoinitiator described herein), for example, under conditions described herein that promote a radical-mediated thiol-ene reaction, wherein P, $C_t$, t, Q and y are as defined for formula (D) or any variations thereof.

In one aspect each $CH_2=CH$— moiety of $[CH_2=CH]_y$Q is a reactive ene group independently selected from the group consisting of vinylacetyl, vinyl ester, vinylsulfonyl, vinyl ether, allyl, acrylate ester, methacrylate ester, acrylamido, allyl ether, alkenyl, unsaturated ester, dienyl, and N-vinylcarbamoyl.

It is understood that $[CH_2=CH]_y$Q represents an ene group bearing one or more terminal, unsubstituted alkene moieties, but that substituted alkenes may also be employed and are also described herein. Thus, it will be appreciated that the compound of formula (D) in which the C—C moiety is derived from an alkene other than a terminal, unsubstituted alkene is also provided and may be produced by reacting a compound of formula P—$C_t$—SH and a compound of formula $[T]_y$-Q and a radical initiator (such as a photoinitiator described herein), wherein P, t, Q and x are as defined for formula (D) or any variations thereof and T indicates an alkene moiety other than a terminal, unsubstituted alkene moiety, under free radical-mediated reaction conditions. In one aspect, $[T]_y$-Q comprises one or more a cyclic alkene moiety and $[T]_y$-Q is of the following formula

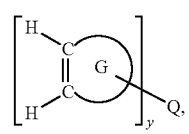

wherein each ring G is independently a monocyclic or bicyclic cycloalkene, which can have one or more annular heteroatoms selected from O, S, and N, and which may be substituted with one or more substituents selected from the group consisting of oxo, halo, alkyl and alkoxy, and where the bicyclic cycloalkene may be a fused, bridged or a spiro bicyclic ring. It will be appreciated that Q may be directly, independently for each of the one or more T moieties, attached to T or may be linked to T via a linker moiety, such as, for non-limiting example, an amide functionality, ester functionality or a combination thereof. Examples of $[T]_y$-Q include Q moieties derivatized with one or more groups independently selected from maleimido group, a propenyl ether group, a norborn-2-en-5-yl group and any combination thereof, any one or more of which may be directly connected to Q or connected to Q via a linker moiety, such as, for non-limiting example, an amide functionality, ester functionality or a combination thereof.

In some embodiments, each T moiety of $[T]_y$-Q is norborn-2-en-5-yl. As will be understood by one skilled in the art, there are a number of ways to add one or more $CH_2=CH$-moieties to the Q group of $[CH_2=CH]_yQ$ or to add one or more T moiety to the Q group of $[T]_y$-Q. These methods may result in a linker group between the ene/yne-bearing moiety and the ene/yne functional group, such as, for non-limiting example, an amide functionality, ester functionality or a combination thereof. In a preferred embodiment, a PEG is modified with 5-norbornene-2-carboxylic acid such that terminal norbornene(s) (norborn-2-en-5-yl) will be added to the PEG via an ester linkage. In another embodiment, PEG amine is modified with NHS-Norbornene such that terminal norbornene(s) (norborn-2-en-5-yl) will be added to the PEG via an amide linkage. In some embodiments, each $CH_2=CH$— moiety of $[CH_2=CH]_yQ$ is a moiety independently selected from the group consisting of $CH_2=CH-C(=O)-$, $CH_2=CH-S(=O)_2-$, $CH_2=CH-O-$, $CH_2=CH-(C_0-C_4)$-alkanediyl-, $CH_2=CH-C(=O)O-$, $CH_2=C(CH_3)-C(=O)O-$, $CH_2=CH-C(=O)NH-$, $CH_2=CH-CH_2-O-$, and $CH_2=CH-NHC(=O)-$, and each T moiety of $[T]_y$-Q is independently selected from the group consisting of

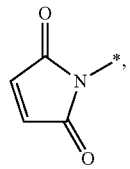

—CH(CH$_3$)=CH—O— and

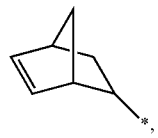

wherein the asterisk represents bonding to the Q group which may be a direct bond or via a linker moiety, such as, for non-limiting example, an amide functionality, ester functionality or a combination thereof. In some embodiments, the compound of formula (D) is produced in a reduced oxygen environment or in the absence of oxygen, such as in the presence of a degassed solvent.

In some embodiments, the compound of formula (D) is produced in a reduced oxygen environment or in the absence of oxygen.

In some embodiments of formula (D), P can be selected from peptide and protein hormones, growth factors, cytokines, interleukins, receptors, solubilized receptors, therapeutic proteins, enzymes, and structural proteins. Growth factors may include AM, Ang, BMP, BDNF, GDNF, GCSF, GM-CSF, GDF, HGF, HDGF, KGF, MSF, NGF, TPO, FBS, EPO, IGF, EGF, FGF, TGF, PDGF and interleukins includ-ing their derivatives and family members. Structural proteins include fibrin, fibrinogen, fibronectins, keratins, actins, laminins and collagens.

In some embodiments of formula (D), the polypeptide P further comprises a peptide sequence known to be sensitive to a protease. In a particular embodiment, the polypeptide is a homocysteine-flanked matrix metalloproteinase (MMP) degradable peptide, to create a hydrogel network that is degraded by cell-secreted MMPs. In another embodiment, the polypeptide is an active thiol-flanked plasmin degradable peptide. In another, two plasmin degradable sequences are included within the peptide.

In some embodiments of formula (D), Q is a polymeric moiety of formula (Qc):

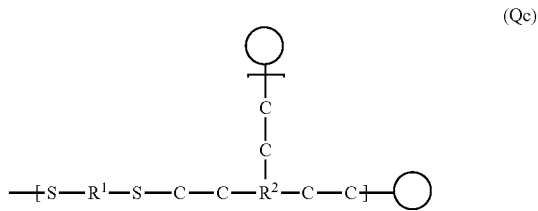

wherein, $R^1$ and $R^2$ are independently selected from the group consisting of poly(lactic acid) (PLA); polyglycolide (PGA); a copolymer of PLA and PGA (PLGA); poly(vinyl alcohol) (PVA); poly(ethylene glycol) (PEG); poly(ethylene oxide); a poly(ethylene oxide)-co-poly(propylene oxide) block copolymer; a poloxamine; a polyanhydride; a polyorthoester; a poly(hydroxy acids); a polydioxanone; a polycarbonate; a polyaminocarbonate; a poly(vinyl pyrrolidone); a poly(ethyl oxazoline); a polyurethane; a carboxymethyl cellulose; a hydroxyalkylated cellulose; a polypeptide; a nucleic acid; a modified nucleic acid; a locked nucleic acid; a polysaccharide; a carbohydrate; heparan sulfate; chondroitin sulfate; heparin, alginate; and a combination thereof; and wherein —O represents a point of attachment to either one of the sulfur atom of one of the P—C$_t$—S— moieties of formula (D) or a thioether moiety of another subunit of the polymeric moiety of formula (Qc). In some embodiments, $R^1$ is a polypeptide of formula —C$_t$—R$^{1a}$—C$_t$—, wherein $R^{1a}$ is a polypeptide, t≥2 and C$_t$ is a linker comprising at least two carbon atoms. In some embodiments, C$_t$ is selected from the group consisting of $(C_2-C_6)$alkanediyl-, —C(=O)—$(C_1-C_6)$-alkanediyl- and —C(=O)—$(C_1-C_6)$-alkanediyl-(O—CH$_2$CH$_2$)$_z$— where z is an integer from 1-10,000. In some embodiments, C$_t$ may be further substituted with one or more substituents selected from halo, alkyl, and alkoxy. As is understood by a person of skill in the art, each C—C moiety between the sulfur atom and $R^2$ is a moiety resulting from the thiol-ene reaction of a reactive thiol group with a reactive ene group, such as a reactive ene group independently selected from the group consisting of vinylacetyl, vinyl ester, vinylsulfonyl, vinyl ether, allyl, acrylate ester, methacrylate ester, acrylamido, maleimido, propenyl ether, allyl ether, alkenyl, unsaturated ester, dienyl, N-vinylcarbamoyl and norborn-2-en-5-yl. In some embodiments, the C—C moiety between the sulfur atom and $R^2$ is a moiety resulting from the thiol-ene reaction of a reactive thiol group with a reactive ene group, wherein the reactive ene group is norborn-2-en-5-yl. As will be understood by one skilled in the art, there are a number of ways to add a C—C moiety to the $R^2$ group. These methods may result in a linker group between the ene/yne-bearing moiety and the ene/yne functional group, such as, for non-limiting example, an amide functionality, ester functionality or a combination thereof. In one embodiment, a PEG is modified with 5-norbornene-2-carboxylic acid such that one or more terminal norbornene moiety (norborn-2-en-5-yl) is added to the PEG via an ester linkage. In another embodiment, PEG amine is modified with NHS-Norbornene such that one or more terminal norbornene moiety (norborn-2-en-5-yl) is added to the PEG via an amide linkage. In some embodiments, each C—C moiety between the sulfur atom and $R^2$ is a moiety independently selected from the group consisting of —CH$_2$—CH$_2$—CH$_2$—C(=O)—, —CH$_2$—CH$_2$—OC(=O)—, —CH$_2$—CH$_2$—S(=O)$_2$—, —CH$_2$—CH$_2$—O—, —(C$_2$-C$_6$)-alkanediyl-, —CH$_2$—CH$_2$—C(=O)O—, —CH$_2$—CH(CH$_3$)—C(=O)O—, —CH$_2$—CH$_2$—C(=O)NH—, —CH(CH$_3$)—CH$_2$—O—, —CH$_2$—CH$_2$—CH$_2$—O—, —CH$_2$—CH$_2$—NHC(=O)—,

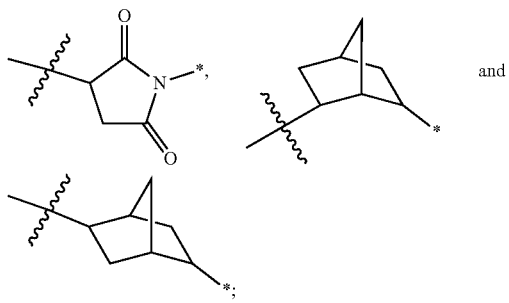

wherein the first dash (—C—C) or wavy line represents bonding to the sulfur atom and the second dash (C—C—) or bonding to the $R^2$ group which may be a direct bond or via a linker moiety, such as, for non-limiting example, an amide functionality, ester functionality or a combination thereof. It will be appreciated that such C—C moieties are derived from an ene group comprising a moiety selected from the group consisting of vinylacetyl, vinyl ester, vinylsulfonyl, vinyl ether, allyl, acrylate ester, methacrylate ester, acrylamido, maleimido, propenyl ether, allyl ether, alkenyl, unsaturated ester, dienyl, N-vinylcarbamoyl and norborn-2-en-5-yl. In some embodiments, $R^1$ is a polypeptide of formula —C$_t$—R$^{1b}$—C$_t$—, wherein R$^{1b}$ is a polypeptide, t≥1 and C$_t$ is a linker comprising at least one carbon atom, wherein each residue of R$^{1b}$ comprising a C$_t$ linker may be selected from the group consisting of a natural amino acid residue, a rare amino acid residue, an unnatural amino acid residue, an amino acid analog residue or an amino acid mimetic residue, provided that the natural amino acid residue comprising the C$_t$ linker is not a cysteine residue. In some embodiments, the unnatural amino acid residue is a thiol substituted beta amino acid residue, a thiol substituted gamma amino acid residue, a thiol substituted delta amino acid residue or a thiol substituted epsilon amino acid residue. In some embodiments, the amino acid analog residue or amino acid mimetic residue is derived from a natural amino acid residue or unnatural amino acid residue in which the carbonyl functionality is replaced by a methylene moiety. In some embodiments, the amino acid analog residue or the amino acid mimetic residue is derived from a natural amino acid residue or unnatural amino acid residue in which the amino functionality is replaced by a methylene moiety. In some embodiments, C$_t$ is selected from the group consisting of (C$_2$-C$_6$)alkanediyl-, —C(=O)—(C$_1$-C$_6$)-alkanediyl- and —C(=O)—(C$_1$-C$_6$)-alkanediyl-(O—CH$_2$CH$_2$)$_z$— where z is an integer from 1-10,000. In some embodiments, C$_t$ may be further substituted with one or more substituents selected from halo, alkyl, and alkoxy.

$R^1$ and $R^2$ can vary in size depending upon desired properties for the resulting polymeric material. More particularly, the molecular weight for $R^1$ and $R^2$ can range from about 30 Da to about 50000 Da. Prior to formation of the polymeric material of the present invention, $R^1$ can be derivatized to include two or more reactive thiol groups and $R^2$ can be derivatized to include three or more reactive ene group such that they can participate in photo-initiated thiol-ene polymerization that they can participate in photo-initiated thiol-ene polymerization. Thiolated macromers such as poly(ethylene glycol) dithiol are available commercially. The reactive ene groups can be selected from any suitable compound having a carbon-carbon double bond. For example, the reactive ene group can be selected from any suitable ethylenically unsaturated group such as, but not limited to, vinylacetyl, vinyl ester, vinylsulfonyl, vinyl ether, allyl, acrylate ester, methacrylate ester, acrylamido, maleimido, propenyl ether, allyl ether, alkenyl, unsaturated ester, dienyl, N-vinylcarbamoyl and norborn-2-en-5-yl. Thus, it will be appreciated that in the repeating unit shown above, the carbons can be CH$_2$ or can be substituted at one or more than one of the carbons within the repeating group, even including ring structures incorporating a double bond. If $R^1$ is derivatized with two reactive thiol and $R^2$ is derivatized with two reactive ene groups, the resulting thiol-ene polymer would be a linear copolymer composed of alternating $R^1$ and $R^2$ segments. However, the thiol-ene polymeric material is preferably formed to contain cross-linking and branching. Thus, the derivatized $R^1$ and $R^2$ segments preferably have more than two reactive thiol groups or reactive ene groups per molecule that can participate in crosslinking and polymerization. The extent of the branching and cross-linking can be controlled by the use of differently derivatized $R^1$ and $R^2$ segments and control over the concentration of the starting materials.

In some embodiments of formula (D), Q is a polymeric moiety of formula (Qd):

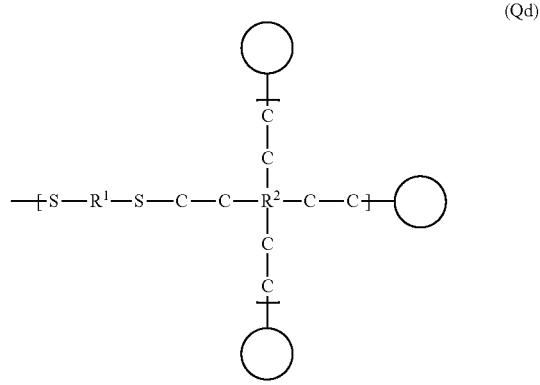

(Qd)

wherein, $R^1$ and $R^2$ are independently selected from the group consisting of poly(lactic acid) (PLA); polyglycolide (PGA); a copolymer of PLA and PGA (PLGA); poly(vinyl alcohol) (PVA); poly(ethylene glycol) (PEG); poly(ethylene oxide); a poly(ethylene oxide)-co-poly(propylene oxide) block copolymer; a poloxamine; a polyanhydride; a poly-orthoester; a poly(hydroxy acids); a polydioxanone; a polycarbonate; a polyaminocarbonate; a poly(vinyl pyrrolidone); a poly(ethyl oxazoline); a polyurethane; a carboxymethyl cellulose; a hydroxyalkylated cellulose; a polypeptide; a nucleic acid; a modified nucleic acid; a locked nucleic acid; a polysaccharide; a carbohydrate; heparan sulfate; chondroitin sulfate; heparin, alginate; and a combination thereof; and wherein —O represents a point of attachment to either one of the sulfur atom of one of the P—$C_t$—S— moieties of formula (D) or a thioether moiety of another subunit of the polymeric moiety of formula (Qd). In some embodiments, $R^1$ is a polypeptide of formula —$C_t$—$R^{1a}$—$C_t$, wherein $R^{1a}$ is a polypeptide, t≥2 and $C_t$ is a linker comprising at least two carbon atoms. In some embodiments, $C_t$ is selected from the group consisting of ($C_2$-$C_6$)alkanediyl-, —C(=O)—($C_1$-$C_6$)-alkanediyl- and —C(=O)—($C_1$-$C_6$)-alkanediyl-(O—$CH_2CH_2$)$_z$— where z is an integer from 1-10,000. In some embodiments, $C_t$ may be further substituted with one or more substituents selected from halo, alkyl, and alkoxy. As is understood by a person of skill in the art, each C—C moiety between the sulfur atom and $R^2$ is a moiety resulting from the thiol-ene reaction of a reactive thiol group with a reactive ene group, such as a reactive ene group independently selected from the group consisting of vinylacetyl, vinyl ester, vinylsulfonyl, vinyl ether, allyl, acrylate ester, methacrylate ester, acrylamido, maleimido, propenyl ether, allyl ether, alkenyl, unsaturated ester, dienyl, N-vinylcarbamoyl and norborn-2-en-5-yl. In some embodiments, the C—C moiety between the sulfur atom and $R^2$ is a moiety resulting from the thiol-ene reaction of a reactive thiol group with a reactive ene group, wherein the reactive ene group is norborn-2-en-5-yl. As will be understood by one skilled in the art, there are a number of ways to add a C—C moiety to the $R^2$ group. These methods may result in a linker group between the ene/yne-bearing moiety and the ene/yne functional group, such as, for non-limiting example, an amide functionality, ester functionality or a combination thereof. In one embodiment, a PEG is modified with 5-norbornene-2-carboxylic acid such that one or more terminal norbornene moiety (norborn-2-en-5-yl) is added to the PEG via an ester linkage. In another embodiment, PEG amine is modified with NHS-Norbornene such that one or more terminal norbornene moiety (norborn-2-en-5-yl) is added to the PEG via an amide linkage. In some embodiments, each C—C moiety between the sulfur atom and $R^2$ is a moiety independently selected from the group consisting of —$CH_2$—$CH_2$—$CH_2$—C(=O)—, —$CH_2$—$CH_2$—OC(=O)—, —$CH_2$—$CH_2$—S(=O)$_2$—, —$CH_2$—$CH_2$—O—, —($C_2$-$C_6$)-alkanediyl-, —$CH_2$—$CH_2$—C(=O)O—, —$CH_2$—CH(CH$_3$)—C(=O)O—, —$CH_2$—$CH_2$—C(=O)NH—, —CH(CH$_3$)—$CH_2$—O—, —$CH_2$—$CH_2$—$CH_2$—O—, —$CH_2$—$CH_2$—NHC(=O)—,

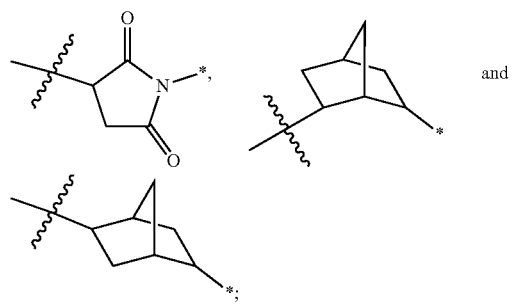

wherein the first dash (—C—C) or wavy line represents bonding to the sulfur atom and the second dash (C—C—) or bonding to the $R^2$ group which may be a direct bond or via a linker moiety, such as, for non-limiting example, an amide functionality, ester functionality or a combination thereof. It will be appreciated that such C—C moieties are derived from an ene group comprising a moiety selected from the group consisting of vinylacetyl, vinyl ester, vinylsulfonyl, vinyl ether, allyl, acrylate ester, methacrylate ester, acrylamido, maleimido, propenyl ether, allyl ether, alkenyl, unsaturated ester, dienyl, N-vinylcarbamoyl and norborn-2-en-5-yl. In some embodiments, $R^1$ is a polypeptide of formula —$C_t$—$R^{1b}$—$C_t$—, wherein $R^{1b}$ is a polypeptide, t≥1 and $C_t$ is a linker comprising at least one carbon atom, wherein each residue of $R^{1b}$ comprising a $C_t$ linker may be selected from the group consisting of a natural amino acid residue, a rare amino acid residue, an unnatural amino acid residue, an amino acid analog residue or an amino acid mimetic residue, provided that the natural amino acid residue comprising the $C_t$ linker is not a cysteine residue. In some embodiments, the unnatural amino acid residue is a thiol substituted beta amino acid residue, a thiol substituted gamma amino acid residue, a thiol substituted delta amino acid residue or a thiol substituted epsilon amino acid residue. In some embodiments, the amino acid analog residue or amino acid mimetic residue is derived from a natural amino acid residue or unnatural amino acid residue in which the carbonyl functionality is replaced by a methylene moiety. In some embodiments, the amino acid analog residue or the amino acid mimetic residue is derived from a natural amino acid residue or unnatural amino acid residue in which the amino functionality is replaced by a methylene moiety. In some embodiments, $C_t$ is selected from the group consisting of ($C_2$-$C_6$)alkanediyl-, —C(=O)—($C_1$-$C_6$)-alkanediyl- and —C(=O)—($C_1$-$C_6$)-alkanediyl-(O—$CH_2CH_2$)$_z$— where z is an integer from 1-10,000. In some embodiments, $C_t$ may be further substituted with one or more substituents selected from halo, alkyl, and alkoxy.

$R^1$ and $R^2$ can vary in size depending upon desired properties for the resulting polymeric material. More particularly, the molecular weight for $R^1$ and $R^2$ can range from about 30 Da to about 50000 Da. Prior to formation of the polymeric material of the present invention, $R^1$ can be derivatized to include two or more reactive thiol groups and $R^2$ can be derivatized to include three or more reactive ene group such that they can participate in photo-initiated thiol-ene polymerization that they can participate in photo-initiated thiol-ene polymerization. Thiolated macromers such as poly(ethylene glycol) dithiol are available commercially. The reactive ene groups can be selected from any suitable compound having a carbon-carbon double bond. For example, the reactive ene group can be selected from any suitable ethylenically unsaturated group such as, but not limited to, vinylacetyl, vinyl ester, vinylsulfonyl, vinyl ether, allyl, acrylate ester, methacrylate ester, acrylamido, maleimido, propenyl ether, allyl ether, alkenyl, unsaturated ester, dienyl, N-vinylcarbamoyl and norborn-2-en-5-yl. Thus, it will be appreciated that in the repeating unit shown above, the carbons can be $CH_2$ or can be substituted at one or more than one of the carbons within the repeating group, even including ring structures incorporating a double bond. If $R^1$ is derivatized with two reactive thiol and $R^2$ is derivatized with two reactive ene groups, the resulting thiol-ene polymer would be a linear copolymer composed of alternating $R^1$ and $R^2$ segments. However, the thiol-ene polymeric material is preferably formed to contain cross-linking and branching. Thus, the derivatized $R^1$ and $R^2$ segments preferably have more than two reactive thiol groups or reactive ene groups per molecule that can participate in crosslinking and polymerization. The extent of the branching and crosslinking can be controlled by the use of differently derivatized $R^1$ and $R^2$ segments and control over the concentration of the starting materials.

Also provided is a polymeric material (e.g. a thiol-ene hydrogel) comprising repeating units of the formula (IV):

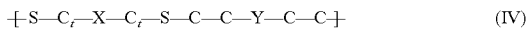 (IV)

wherein X is a polypeptide, t≥1 and $C_t$ is a linker comprising at least one carbon atom, wherein each residue of X comprising a $C_t$ linker may be selected from the group consisting of a natural amino acid residue, a rare amino acid residue, an unnatural amino acid residue, an amino acid analog residue or an amino acid mimetic residue, provided that the natural amino acid residue comprising the $C_t$ linker is not a cysteine residue, and Y is selected from the group consisting of poly(lactic acid) (PLA); polyglycolide (PGA); a copolymer of PLA and PGA (PLGA); poly(vinyl alcohol) (PVA); poly(ethylene glycol) (PEG); poly(ethylene oxide); a poly(ethylene oxide)-co-poly(propylene oxide) block copolymer; a poloxamine; a polyanhydride; a polyorthoester; a poly(hydroxy acids); a polydioxanone; a polycarbonate; a polyaminocarbonate; a poly(vinyl pyrrolidone); a poly(ethyl oxazoline); a polyurethane; a carboxymethyl cellulose; a hydroxyalkylated cellulose; a polypeptide; a nucleic acid; a modified nucleic acid; a locked nucleic acid; a polysaccharide; a carbohydrate; heparan sulfate; chondroitin sulfate; heparin, alginate; and a combination thereof. In some embodiments, the unnatural amino acid residue is a thiol substituted beta amino acid residue, a thiol substituted gamma amino acid residue, a thiol substituted delta amino acid residue or a thiol substituted epsilon amino acid residue. In some embodiments, the amino acid analog residue or amino acid mimetic residue is derived from a natural amino acid residue or unnatural amino acid residue in which the carbonyl functionality is replaced by a methylene moiety. In some embodiments, the amino acid analog residue or the amino acid mimetic residue is derived from a natural amino acid residue or unnatural amino acid residue in which the amino functionality is replaced by a methylene moiety. In some embodiments, $C_t$ is selected from the group consisting of $(C_2-C_6)$alkanediyl-, —C(=O)—$(C_1-C_6)$-alkanediyl- and —C(=O)—$(C_1-C_6)$-alkanediyl-(O—$CH_2CH_2$)$_z$— where z is an integer from 1-10,000. In some embodiments, $C_t$ may be further substituted with one or more substituents selected from halo, alkyl, and alkoxy. As is understood by a person of skill in the art, each C—C moiety between the sulfur atom and Y is a moiety resulting from the thiol-ene reaction of a reactive thiol group with a reactive ene group, such as a reactive ene group independently selected from the group consisting of vinylacetyl, vinyl ester, vinylsulfonyl, vinyl ether, allyl, acrylate ester, methacrylate ester, acrylamido, maleimido, propenyl ether, allyl ether, alkenyl, unsaturated ester, dienyl, N-vinylcarbamoyl and norborn-2-en-5-yl. In some embodiments, the C—C moiety between the sulfur atom and Y is a moiety resulting from the thiol-ene reaction of a reactive thiol group with a reactive ene group, wherein the reactive ene group is norborn-2-en-5-yl. As will be understood by one skilled in the art, there are a number of ways to add a C—C moiety to the Y group. These methods may result in a linker group between the ene/yne-bearing moiety and the ene/yne functional group, such as, for non-limiting example, an amide functionality, ester functionality or a combination thereof. In one embodiment, a PEG is modified with 5-norbornene-2-carboxylic acid such that one or more terminal norbornene moiety (norborn-2-en-5-yl) is added to the PEG via an ester linkage. In another embodiment, PEG amine is modified with NHS-Norbornene such that one or more terminal norbornene moiety (norborn-2-en-5-yl) is added to the PEG via an amide linkage. In some embodiments, each C—C moiety between the sulfur atom and Y is a moiety independently selected from the group consisting of —$CH_2$—$CH_2$—$CH_2$—C(=O)—, —$CH_2$—$CH_2$—OC(=O)—, —$CH_2$—$CH_2$—S(=O)$_2$—, —$CH_2$—$CH_2$—O—, —$(C_2-C_6)$-alkanediyl-, —$CH_2$—$CH_2$—C(=O)O—, —$CH_2$—CH($CH_3$)—C(=O)O—, —$CH_2$—$CH_2$—C(=O)NH—, —CH($CH_3$)—$CH_2$—O—, —$CH_2$—$CH_2$—$CH_2$—O—, —$CH_2$—$CH_2$—NHC(=O)—,

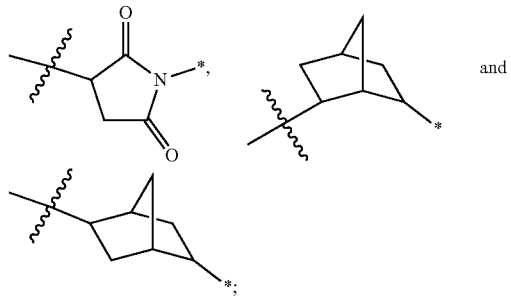

wherein the first dash (—C—C) or wavy line represents bonding to the sulfur atom and the second dash (C—C—) or bonding to the Y group which may be a direct bond or via a linker moiety, such as, for non-limiting example, an amide functionality, ester functionality or a combination thereof. It will be appreciated that such C—C moieties are derived from an ene group comprising a moiety selected from the group consisting of vinylacetyl, vinyl ester, vinylsulfonyl, vinyl ether, allyl, acrylate ester, methacrylate ester, acrylamido, maleimido, propenyl ether, allyl ether, alkenyl, unsaturated ester, dienyl, N-vinylcarbamoyl and norborn-2-en-5-yl.

Also provided is a polymeric material [e.g. to a thiol-ene hydrogel] comprising repeating units of the formula (V):

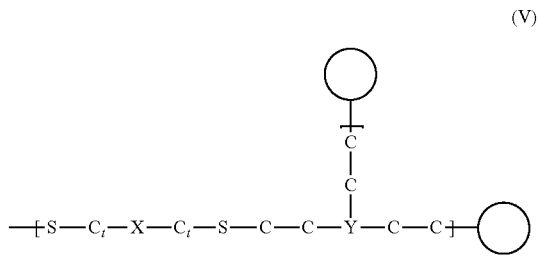 (V)

wherein X is a polypeptide, t≥1 and $C_t$ is a linker comprising at least one carbon atom, wherein each residue of X comprising a $C_t$ linker may be selected from the group consisting of a natural amino acid residue, a rare amino acid residue, an unnatural amino acid residue, an amino acid analog residue or an amino acid mimetic residue, provided that the natural amino acid residue comprising the $C_t$ linker is not a cysteine residue, and Y is selected from the group consisting of poly(lactic acid) (PLA); polyglycolide (PGA); a copolymer of PLA and PGA (PLGA); poly(vinyl alcohol) (PVA); poly(ethylene glycol) (PEG); poly(ethylene oxide); a poly(ethylene oxide)-co-poly(propylene oxide) block copolymer; a poloxamine; a polyanhydride; a polyorthoester; a poly(hydroxy acids); a polydioxanone; a polycarbonate; a polyaminocarbonate; a poly(vinyl pyrrolidone); a poly(ethyl oxazoline); a polyurethane; a carboxymethyl cellulose; a hydroxyalkylated cellulose; a polypeptide; a nucleic acid; a modified nucleic acid; a locked nucleic acid; a polysaccharide; a carbohydrate; heparan sulfate; chondroitin sulfate; heparin, alginate; and a combination thereof; wherein —○ represents a point of attachment to a thioether moiety of another subunit of the polymeric moiety of formula (V). In some embodiments, the unnatural amino acid residue is a thiol substituted beta amino acid residue, a thiol substituted gamma amino acid residue, a thiol substituted delta amino acid residue or a thiol substituted epsilon amino acid residue. In some embodiments, the amino acid analog residue or amino acid mimetic residue is derived from a natural amino acid residue or unnatural amino acid residue in which the carbonyl functionality is replaced by a methylene moiety. In some embodiments, the amino acid analog residue or the amino acid mimetic residue is derived from a natural amino acid residue or unnatural amino acid residue in which the amino functionality is replaced by a methylene moiety. In some embodiments, $C_t$ is selected from the group consisting of $(C_2-C_6)$alkanediyl-, —C(=O)—$(C_1-C_6)$-alkanediyl- and —C(=O)—$(C_1-C_6)$-alkanediyl-(O—CH$_2$CH$_2$)$_z$— where z is an integer from 1-10,000. In some embodiments, $C_t$ may be further substituted with one or more substituents selected from halo, alkyl, and alkoxy. As is understood by a person of skill in the art, each C—C moiety between the sulfur atom and Y is a moiety resulting from the thiol-ene reaction of a reactive thiol group with a reactive ene group, such as a reactive ene group independently selected from the group consisting of vinylacetyl, vinyl ester, vinylsulfonyl, vinyl ether, allyl, acrylate ester, methacrylate ester, acrylamido, maleimido, propenyl ether, allyl ether, alkenyl, unsaturated ester, dienyl, N-vinylcarbamoyl and norborn-2-en-5-yl. In some embodiments, the C—C moiety between the sulfur atom and Y is a moiety resulting from the thiol-ene reaction of a reactive thiol group with a reactive ene group, wherein the reactive ene group is norborn-2-en-5-yl. As will be understood by one skilled in the art, there are a number of ways to add a C—C moiety to the Y group. These methods may result in a linker group between the ene/yne-bearing moiety and the ene/yne functional group, such as, for non-limiting example, an amide functionality, ester functionality or a combination thereof. In one embodiment, a PEG is modified with 5-norbornene-2-carboxylic acid such that one or more terminal norbornene moiety (norborn-2-en-5-yl) is added to the PEG via an ester linkage. In another embodiment, PEG amine is modified with NHS-Norbornene such that one or more terminal norbornene moiety (norborn-2-en-5-yl) is added to the PEG via an amide linkage. In some embodiments, each C—C moiety between the sulfur atom and Y is a moiety independently selected from the group consisting of —CH$_2$—CH$_2$—CH$_2$—C(=O)—, —CH$_2$—CH$_2$—OC(=O)—, —CH$_2$—CH$_2$—S(=O)$_2$—, —CH$_2$—CH$_2$—O—, —(C$_2$-C$_6$)-alkanediyl-, —CH$_2$—CH$_2$—C(=O)O—, —CH$_2$—CH(CH$_3$)—C(=O)O—, —CH$_2$—CH$_2$—C(=O)NH—, —CH(CH$_3$)—CH$_2$—O—, —CH$_2$—CH$_2$—CH$_2$—O—, —CH$_2$—CH$_2$—NHC(=O)—,

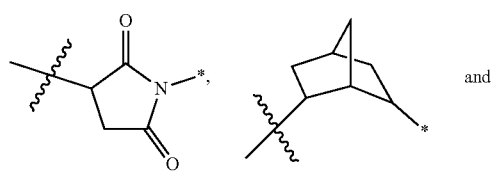

and

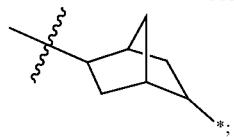

wherein the first dash (—C—C) or wavy line represents bonding to the sulfur atom and the second dash (C—C—) or bonding to the Y group which may be a direct bond or via a linker moiety, such as, for non-limiting example, an amide functionality, ester functionality or a combination thereof. It will be appreciated that such C—C moieties are derived from an ene group comprising a moiety selected from the group consisting of vinylacetyl, vinyl ester, vinylsulfonyl, vinyl ether, allyl, acrylate ester, methacrylate ester, acrylamido, maleimido, propenyl ether, allyl ether, alkenyl, unsaturated ester, dienyl, N-vinylcarbamoyl and norborn-2-en-5-yl.

Also provided is a polymeric material [e.g. to a thiol-ene hydrogel] comprising repeating units of the formula (VI):

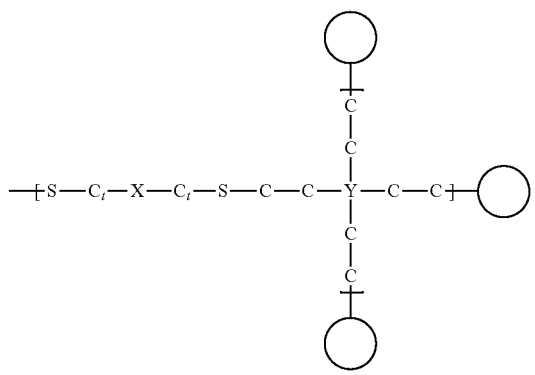

wherein X is a polypeptide, t≥1 and $C_t$ is a linker comprising at least one carbon atom, wherein each residue of X comprising a $C_t$ linker may be selected from the group consisting of a natural amino acid residue, a rare amino acid residue, an unnatural amino acid residue, an amino acid analog residue or an amino acid mimetic residue, provided that the natural amino acid residue comprising the $C_t$ linker is not a cysteine residue, and Y is selected from the group consisting of poly(lactic acid) (PLA); polyglycolide (PGA); a copolymer of PLA and PGA (PLGA); poly(vinyl alcohol) (PVA); poly(ethylene glycol) (PEG); poly(ethylene oxide); a poly (ethylene oxide)-co-poly(propylene oxide) block copolymer; a poloxamine; a polyanhydride; a polyorthoester; a poly(hydroxy acids); a polydioxanone; a polycarbonate; a polyaminocarbonate; a poly(vinyl pyrrolidone); a poly(ethyl oxazoline); a polyurethane; a carboxymethyl cellulose; a hydroxyalkylated cellulose; a polypeptide; a nucleic acid; a modified nucleic acid; a locked nucleic acid; a polysaccharide; a carbohydrate; heparan sulfate; chondroitin sulfate; heparin, alginate; and a combination thereof; wherein —○ represents a point of attachment to a thioether moiety of another subunit of the polymeric moiety of formula (VI). In some embodiments, the unnatural amino acid residue is a thiol substituted beta amino acid residue, a thiol substituted gamma amino acid residue, a thiol substituted delta amino acid residue or a thiol substituted epsilon amino acid residue.

In some embodiments, the amino acid analog residue or amino acid mimetic residue is derived from a natural amino acid residue or unnatural amino acid residue in which the carbonyl functionality is replaced by a methylene moiety. In some embodiments, the amino acid analog residue or the amino acid mimetic residue is derived from a natural amino acid residue or unnatural amino acid residue in which the amino functionality is replaced by a methylene moiety. In some embodiments, $C_t$ is selected from the group consisting of $(C_2-C_6)$alkanediyl-, —C(=O)—$(C_1-C_6)$-alkanediyl- and —C(=O)—$(C_1-C_6)$-alkanediyl-(O—$CH_2CH_2$)$_z$— where z is an integer from 1-10,000. In some embodiments, $C_t$ may be further substituted with one or more substituents selected from halo, alkyl, and alkoxy. As is understood by a person of skill in the art, each C—C moiety between the sulfur atom and Y is a moiety resulting from the thiol-ene reaction of a reactive thiol group with a reactive ene group, such as a reactive ene group independently selected from the group consisting of vinylacetyl, vinyl ester, vinylsulfonyl, vinyl ether, allyl, acrylate ester, methacrylate ester, acrylamido, maleimido, propenyl ether, allyl ether, alkenyl, unsaturated ester, dienyl, N-vinylcarbamoyl and norborn-2-en-5-yl. In some embodiments, the C—C moiety between the sulfur atom and Y is a moiety resulting from the thiol-ene reaction of a reactive thiol group with a reactive ene group, wherein the reactive ene group is norborn-2-en-5-yl. As will be understood by one skilled in the art, there are a number of ways to add a C—C moiety to the Y group. These methods may result in a linker group between the ene/yne-bearing moiety and the ene/yne functional group, such as, for non-limiting example, an amide functionality, ester functionality or a combination thereof. In one embodiment, a PEG is modified with 5-norbornene-2-carboxylic acid such that one or more terminal norbornene moiety (norborn-2-en-5-yl) is added to the PEG via an ester linkage. In another embodiment, PEG amine is modified with NHS-Norbornene such that one or more terminal norbornene moiety (norborn-2-en-5-yl) is added to the PEG via an amide linkage. In some embodiments, each C—C moiety between the sulfur atom and Y is a moiety independently selected from the group consisting of —$CH_2$—$CH_2$—$CH_2$—C(=O)—, —$CH_2$—$CH_2$—OC(=O)—, —$CH_2$—$CH_2$—S(=O)$_2$—, —$CH_2$—$CH_2$—O—, —$(C_2-C_6)$-alkanediyl-, —$CH_2$—$CH_2$—C(=O)O—, —$CH_2$—CH($CH_3$)—C(=O)O—, —$CH_2$—$CH_2$—C(=O)NH—, —CH($CH_3$)—$CH_2$—O—, —$CH_2$—$CH_2$—$CH_2$—O—, —$CH_2$—$CH_2$—NHC(=O)—,

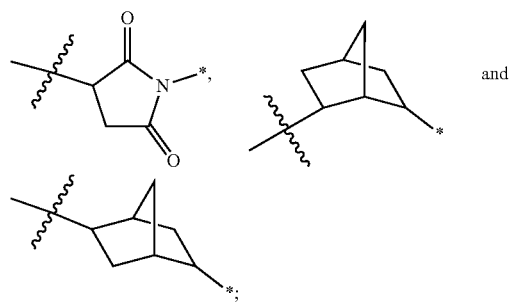

wherein the first dash (—C—C) or wavy line represents bonding to the sulfur atom and the second dash (C—C—) or bonding to the Y group which may be a direct bond or via a linker moiety, such as, for non-limiting example, an amide functionality, ester functionality or a combination thereof. It will be appreciated that such C—C moieties are derived from an ene group comprising a moiety selected from the group consisting of vinylacetyl, vinyl ester, vinylsulfonyl, vinyl ether, allyl, acrylate ester, methacrylate ester, acrylamido, maleimido, propenyl ether, allyl ether, alkenyl, unsaturated ester, dienyl, N-vinylcarbamoyl and norborn-2-en-5-yl.

In some embodiments, the polymeric material of formula (IV), (V) or (VI) may further comprise a biologically active component associated with the polymer matrix of the polymeric material. In some of these embodiments, the biologically active component is encapsulated in the polymer matrix. In some of these embodiments, the biologically active component is covalently bound to (e.g., incorporated into or attached onto) the polymer matrix. This biologically active component may be any of applicable biologically active component described herein, such as a tissue, a cell, a protein, a peptide, a small molecule drug, a nucleic acid, an encapsulated nucleic acid (for example encapsulated in a lipid nanoparticle), a lipid, a carbohydrate, or an agricultural compound described herein.

It will be appreciated that in the repeating unit shown in formulae (C), (D), (IV), (V) and (VI), the carbon atoms can be $CH_2$ or can be substituted at one or more than one of the carbons within the repeating group, even including ring structures incorporating a double bond. Further, it will be appreciated that in order to derivatize the biological active compound with the ene/yne, there may be one or more linking groups between the biologically active compound and the carbon.

Uses

The peptide:polymer compositions described herein or produced by a method described herein can have a number of uses in treating humans and animals. In one embodiment (drug delivery), a biologically active compound is encapsulated, attached or incorporated into a hydrogel and that hydrogel is placed into contact with tissue, such that the biologically active components is released into that tissue. It can be released into the tissue by any of the mechanisms described above, including diffusion from the hydrogel, degradation of the hydrogel, or release via a degradable linker. In another embodiment (tissue regeneration), the hydrogel acts as a scaffold for tissue regeneration. In one such embodiment, cells or tissue are encapsulated in the scaffold, and the scaffold is placed into a tissue defect. The hydrogel can be manufactured in advance, prepolymerized at the time of application, or can be in situ polymerized at the site of the defect. In another embodiment, the hydrogel acts as a scaffold for cells that migrate into the scaffold from surrounding tissues.

In some embodiments, provided is a method for treating a condition or disorder in a subject (e.g. a human or an animal) in need thereof comprising administering a modified polypeptide (such as a polypeptide conjugated with a second moiety) described herein; a biologically active component associated with [e.g., encapsulated in or covalently bond to (incorporated into or attached onto)] a biocompatible cross-linked degradable hydrogel polymer described herein; a compound described herein; or a biologically active component associated with [e.g., encapsulated in or covalently bond to (incorporated into or attached onto)] a polymeric material described herein.

In some embodiments, provided is a method for regenerating tissue comprising releasing a cell or a tissue encapsulated in a biocompatible cross-linked degradable hydrogel polymer described herein at a site of damaged or defective tissue. In some embodiments, the method further comprises producing a composition comprising the biocompatible cross-linked degradable hydrogel polymer at the site of damaged or defective tissue.

Kits

Kits comprising a compound or composition provided herein (e.g., a compound of formula (A)-(D) or (I)-(VI) or a precursor or precursors to such compounds, and optional additional agents, such as an additional biologically active component) are also provided. In one aspect, the kit comprises instructions for use in the treatment of an injury, such as a wound.

Any composition detailed herein above and throughout may be used in the kits, the same as if each and every compound and composition were specifically and individually listed for use in a kit. The kit may optionally include instructions, such as for the use in treating an injury, such as a wound. The kit may include additional components relating to the treatment, such as an applicator, such as a needle and/or syringe, for delivering the compound or composition to the desired site on the individual (such as a wound). The kit may also include a photoinitiator chosen to initiate polymerization. The kit may further contain a light source that emits light at a wavelength chosen to match the absorption spectrum of a photoinitiator used to initiate polymerization.

Articles of Manufacture

Articles of manufacture comprising a container in which a compound or composition provided herein (e.g., a compound of formula (A)-(D) or (I)-(VI) or a precursor or precursors to such compounds, and optional additional agents, such as an additional biologically active component) is contained are provided. The article of manufacture may be a bottle, vial (including a sealed or sealable tube), ampoule, single-use disposable applicator, syringe, or the like. The container may be formed from a variety of materials, such as glass or plastic and in one aspect also contains a label on, or associated with, the container which indicates directions for use in the treatment of an indication provided herein, such as healing a wound.

In one aspect, the container is a medical device containing a unit dosage form of a composition provided herein. The device may contain an applicator for applying the composition to a damaged site on an individual (e.g., a wound). Alternatively, a container (e.g., a bottle, vial or ampoule) may be packaged together with, or provided with instructions for use in conjunction with, a needle and/or syringe which is used to dispense the composition from the container to the desired site (e.g., to the wound). In one aspect, an article of manufacture comprising a compound or composition provided herein or a precursor or precursors to a compound or composition provided herein (e.g., a compound of formula (A)-(D) or (I)-(VI) or a precursor or precursors to such compounds) are packaged together with a second container suitable for obtaining or storing optional additional agents, such as an additional biologically active component.

Any composition described herein may be used in an article of manufacture, the same as if each and every composition were specifically and individually listed for use an article of manufacture.

Enumerated Embodiments

The invention is further described by the following embodiments. The features of each of the embodiments are combinable with any of the other embodiments where appropriate and practical.

Embodiment 1. A method for linking a polypeptide, wherein the polypeptide comprises a peptide backbone and one or more reactive thiol groups, comprising reacting an reactive thiol group of the polypeptide with an ene compound comprising one or more reactive ene groups under conditions that promote a radical-mediated thiol-ene reaction, wherein the reactive thiol group of the polypeptide has a reactivity for the radical-mediated thiol-ene reaction that is at least 2 times that of a cysteine thiol group.

Embodiment 2. The method according to embodiment 1, wherein the method comprising reacting the reactive thiol group of the polypeptide with a radical initiator and the ene compound.

Embodiment 3. The method according to embodiment 1 or 2, wherein the reactive thiol group of the polypeptide is separated from the peptide backbone of the polypeptide by two or more carbon atoms.

Embodiment 4. The method according to embodiment 3, wherein the reactive thiol group of the polypeptide is a thiol group of a homocysteine residue of the polypeptide or a thiol group of a 2-amino-5-mercaptopentanoic acid residue of the polypeptide.

Embodiment 5. The method according to embodiment 3, wherein the reactive thiol group of the polypeptide is a thiol group attached to the side chain amino group of a lysine residue via a linker.

Embodiment 6. The method according to any one of embodiments 2 to 5, wherein the radical initiator is a photoinitiator selected from the group consisting of lithium phenyl-2,4,6-trimethylbenzoylphosphinate (LAP), sodium phenyl-2,4,6-trimethylbenzoylphosphinate (NAP), 2-hydroxy-1-[4-(2-hydroxyethoxy)phenyl]-2-methyl-1-propanone, 1-hydroxy-cyclohexyl-phenyl-ketone and 2,2-dimethoxy-1,2-diphenylethan-1-one.

Embodiment 7. The method according to embodiment 6, wherein a thiol-ene reaction is initiated by exposing the photoinitiator to a light having a wavelength matching the excitation wavelength of the photoinitiator.

Embodiment 8. The method according to embodiments 6 or 7, wherein the method further comprises controlling the amount of the photoinitiator, the intensity of the light and/or the time the photoinitiator is exposed to the light.

Embodiment 9. The method according to embodiment 8, wherein the thiol-ene reaction reaches between about 70% completion and about 95% completion.

Embodiment 10. The method of any one of embodiments 1 to 9, wherein the polypeptide comprises two or more reactive thiol groups each separated from the peptide backbone of the polypeptide by two or more carbon atoms.

Embodiment 11. The method according to embodiment 10, wherein the ene compound comprises two or more reactive ene groups.

Embodiment 12. The method according to embodiment 11, wherein the polypeptide comprises n reactive thiol groups, the ene compound comprises m reactive ene groups, wherein n and m are independently an integer $\geq 2$ and $n+m \geq 5$.

Embodiment 13. The method according to embodiment 12, wherein the ene compound is an ene-modified biocompatible monomer.

Embodiment 14. The method according to embodiment 13, wherein the ene compound is a norbornene-modified polyethylene glycol (PEG).

Embodiment 15. The method according to embodiment 13 or 14, wherein the polypeptide further comprises a peptide sequence known to be sensitive to a protease.

Embodiment 16. The method according to embodiment 15, wherein the thiol-ene reaction provides a biocompatible cross-linked degradable hydrogel polymer.

Embodiment 17. The method of any one of embodiments 1 to 9, wherein the ene compound comprises one reactive ene group.

Embodiment 18. The method according to embodiment 17, wherein the ene compound comprises a polymer, a capture moiety, a label, a carbohydrate, a nucleic acid, or a second polypeptide.

Embodiment 19. The method according to embodiment 17, wherein the ene compound comprises a biological active component.

Embodiment 20. The method according to any one of embodiments 17 to 19, wherein the polypeptide comprises one reactive thiol group separated from the peptide backbone of the polypeptide by two or more carbon atoms.

Embodiment 21. The method according to any one of embodiments 17 to 20, wherein the polypeptide is selected from peptide or protein hormones, growth factors, cytokines, interleukins, receptors, solubilized receptors, therapeutic proteins, enzymes and structural proteins.

Embodiment 22. The method according to any one of embodiments 1 to 9, wherein the polypeptide comprises one reactive thiol group separated from the peptide backbone of the polypeptide by two or more carbon atoms, and the ene compound comprises two or more reactive ene groups.

Embodiment 23. The method according to embodiment 22, wherein the ene compound comprises two or more reactive ene groups.

Embodiment 24. The method according to embodiment 22, wherein the method further comprising reacting a second thiol compound with the ene compound comprising two or more reactive ene groups, wherein the second thiol compound comprises two or more reactive thiol groups.

Embodiment 25. The method according to embodiment 24, wherein the second thiol compound comprises j reactive thiol groups, the ene compound comprises k reactive ene groups, wherein j and k are independently an integer ≥2 and j+k≥5.

Embodiment 26. The method according to embodiment 24 or 25, wherein the second thiol compound comprises a polymeric moiety selected from the group consisting of poly(lactic acid) (PLA); polyglycolide (PGA); a copolymer of PLA and PGA (PLGA); poly(vinyl alcohol) (PVA); poly(ethylene glycol) (PEG); poly(ethylene oxide); a poly(ethylene oxide)-co-poly(propylene oxide) block copolymer; a poloxamine; a polyanhydride; a polyorthoester; a poly(hydroxy acids); a polydioxanone; a polycarbonate; a polyaminocarbonate; a poly(vinyl pyrrolidone); a poly(ethyl oxazoline); a polyurethane; a carboxymethyl cellulose; a hydroxyalkylated cellulose; a polypeptide; a nucleic acid; a modified nucleic acid; a locked nucleic acid; a polysaccharide; a carbohydrate; heparan sulfate; chondroitin sulfate; heparin, alginate; and a combination thereof.

Embodiment 27. The method according to embodiment 24 or 25, wherein the second thiol compound comprises a peptide backbone, a degradable peptide and two or more reactive thiol groups each separated from the peptide backbone by two or more carbon atoms.

Embodiment 28. The method according to embodiment 27, wherein the second thiol compound comprises a peptide sequence known to be sensitive to a protease and two homocysteine residues flanking the peptide sequence.

Embodiment 29. The method according to embodiment 24 or 25, wherein the second thiol compound comprises a polyethylene glycol and two terminal thiol groups attached to the polyethylene glycol.

Embodiment 30. The method of any one of embodiments 22 to 29, wherein the ene compound comprises a polymeric moiety selected from the group consisting of poly(lactic acid) (PLA); polyglycolide (PGA); a copolymer of PLA and PGA (PLGA); poly(vinyl alcohol) (PVA); poly(ethylene glycol) (PEG); poly(ethylene oxide); a poly(ethylene oxide)-co-poly(propylene oxide) block copolymer; a poloxamine; a polyanhydride; a polyorthoester; a poly(hydroxy acids); a polydioxanone; a polycarbonate; a polyaminocarbonate; a poly(vinyl pyrrolidone); a poly(ethyl oxazoline); a polyurethane; a carboxymethyl cellulose; a hydroxyalkylated cellulose; a polypeptide; a nucleic acid; a modified nucleic acid; a locked nucleic acid; a polysaccharide; a carbohydrate; heparan sulfate; chondroitin sulfate; heparin, alginate; and a combination thereof.

Embodiment 31. The method of any one of embodiments 1 to 30, further comprising producing the polypeptide comprising one or more reactive thiol groups.

Embodiment 32. The method of embodiment 31, wherein producing the polypeptide comprising one or more reactive thiol groups comprises polypeptide synthesis using a protected thiol-containing amino acid or amino acid analog wherein the thiol group is separated from the carbon atom adjacent to the carboxy group by two or more carbon atoms, such as a protected homocysteine or 2-amino-5-mercaptopentanoic acid.

Embodiment 33. The method of embodiment 31, wherein producing the polypeptide comprising one or more reactive thiol groups comprises modifying a polypeptide using a thiolating agent.

Embodiment 34. The method of embodiment 31, wherein producing the polypeptide comprising one or more reactive thiol groups comprises chemical or enzymatic conversion of a methionine residue in a polypeptide to a homocysteine residue.

Embodiment 35. A linked polypeptide produced by a method according to any one of embodiments 1 to 34.

Embodiment 36. A method for producing a biocompatible cross-linked degradable hydrogel polymer comprising reacting a reactive thiol compound with a radical initiator and a reactive ene compound, wherein the reactive thiol compound comprising a peptide backbone, a degradable peptide and two or more reactive thiol groups each separated from the peptide backbone by two or more carbon atoms; and the reactive ene compound is an ene-modified biocompatible monomer comprising two or more reactive ene groups.

Embodiment 37. The method according to embodiment 36, wherein the polypeptide comprises n reactive thiol groups, the ene compound comprises m reactive ene groups, wherein n and m are independently an integer ≥2 and n+m≥5.

Embodiment 38. The method according to embodiment 36, further comprising adding a biologically active component to the reaction mixture, wherein the biologically active component is associated with the polymer matrix of the biocompatible cross-linked degradable hydrogel polymer.

Embodiment 39. The method according to embodiment 36 or 38, wherein the reactive thiol groups of the reactive thiol compound are independently selected from a thiol group of a homocysteine residue of the polypeptide, a thiol group of a 2-amino-5-mercaptopentanoic acid residue of the polypeptide and a thiol group attached to the side chain amino group of a lysine residue via a linker.

Embodiment 40. The method according to any one of embodiments 36 to 39, wherein the radical initiator is a photoinitiator selected from the group consisting of lithium phenyl-2,4,6-trimethylbenzoylphosphinate (LAP), sodium phenyl-2,4,6-trimethylbenzoylphosphinate (NAP), 2-hydroxy-1-[4-(2-hydroxyethoxy)phenyl]-2-methyl-1-propanone, 1-hydroxy-cyclohexyl-phenyl-ketone, and 2,2-dimethoxy-1,2-diphenylethan-1-one.

Embodiment 41. The method according to any one of embodiments 36 to 40, wherein the reactive ene compound comprises a polymeric moiety selected from the group consisting of poly(lactic acid) (PLA); polyglycolide (PGA); a copolymer of PLA and PGA (PLGA); poly(vinyl alcohol) (PVA); poly(ethylene glycol) (PEG); poly(ethylene oxide); a poly(ethylene oxide)-co-poly(propylene oxide) block copolymer; a poloxamine; a polyanhydride; a polyorthoester; a poly(hydroxy acids); a polydioxanone; a polycarbonate; a polyaminocarbonate; a poly(vinyl pyrrolidone); a poly(ethyl oxazoline); a polyurethane; a carboxymethyl cellulose; a hydroxyalkylated cellulose; a polypeptide; a nucleic acid; a modified nucleic acid; a locked nucleic acid; a polysaccharide; a carbohydrate; heparan sulfate; chondroitin sulfate; heparin, alginate; and a combination thereof.

Embodiment 42. The method according to any one of embodiments 38 to 41, wherein the biologically active component is a tissue, a cell, a protein, a peptide, a small molecule drug, a nucleic acid, an encapsulated nucleic acid (for example encapsulated in a lipid nanoparticle), a lipid, a carbohydrate, or an agricultural compound.

Embodiment 43. The method according to embodiment 42, wherein the biologically active component is encapsulated in the polymer matrix of the biocompatible cross-linked degradable hydrogel polymer.

Embodiment 44. The method according to embodiment 42, wherein the biologically active component is covalently bond to the polymer matrix of the biocompatible cross-linked degradable hydrogel polymer.

Embodiment 45. The method according to embodiment 44, wherein the biologically active component is a biologically active polypeptide covalently bond to the polymer matrix via a thioether linkage formed by reacting a reactive thiol group of the biologically active polypeptide with an ene group, wherein the thio group of the thioether linkage is separated from the backbone of the biologically active polypeptide by two or more carbon atoms.

Embodiment 46. A biocompatible cross-linked degradable hydrogel polymer produced by a method according to any one of embodiments 35 to 45.

Embodiment 47. The a biocompatible cross-linked degradable hydrogel polymer of embodiment 46, further comprising a biologically active component associated with the polymer matrix of the biocompatible cross-linked degradable hydrogel polymer.

Embodiment 48. A compound of formula (A):

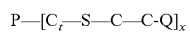

wherein P is a polypeptide, t≥2, $C_t$ is a linker comprising at least two carbon atoms, x is 1 or an integer greater than 1 and Q is a biological active component, a polymer, a capture moiety, a label, a carbohydrate, a nucleic acid, or a second polypeptide.

Embodiment 49. The compound of embodiment 48, wherein the compound is produced by reacting a compound of formula P—[$C_t$—SH]$_x$ and a compound of formula $CH_2$=CH-Q and a radical initiator.

Embodiment 50. A compound of formula (B):

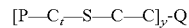

wherein P is a polypeptide, t≥2, $C_t$ is a linker comprising at least two carbon atoms, y is 1 or an integer greater than 1 and Q is selected from the group consisting of poly(lactic acid) (PLA); polyglycolide (PGA); a copolymer of PLA and PGA (PLGA); poly(vinyl alcohol) (PVA); poly(ethylene glycol) (PEG); poly(ethylene oxide); a poly(ethylene oxide)-co-poly(propylene oxide) block copolymer; a poloxamine; a polyanhydride; a polyorthoester; a poly(hydroxy acids); a polydioxanone; a polycarbonate; a polyaminocarbonate; a poly(vinyl pyrrolidone); a a poly(ethyl oxazoline); a polyurethane; a carboxymethyl cellulose; a hydroxyalkylated cellulose; a polypeptide; a nucleic acid; a modified nucleic acid; a locked nucleic acid; a polysaccharide; a carbohydrate; heparan sulfate; chondroitin sulfate; heparin, alginate; and a combination thereof.

Embodiment 51. The compound of embodiment 50, wherein the compound is produced by reacting a compound of formula P—$C_t$—SH and a compound of formula [CH2=CH]$_y$Q and a radical initiator.

Embodiment 52. The compound of embodiment 50, wherein Q is a polymeric moiety of formula (Qa):

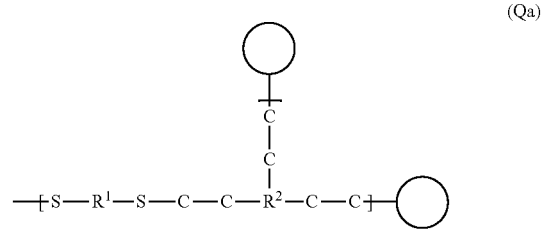

wherein, $R^1$ and $R^2$ are independently selected from the group consisting of poly(lactic acid) (PLA); polyglycolide (PGA); a copolymer of PLA and PGA (PLGA); poly(vinyl alcohol) (PVA); poly(ethylene glycol) (PEG); poly(ethylene oxide); a poly(ethylene oxide)-co-poly(propylene oxide) block copolymer; a poloxamine; a polyanhydride; a polyorthoester; a poly(hydroxy acids); a polydioxanone; a polycarbonate; a polyaminocarbonate; a poly(vinyl pyrrolidone); a poly(ethyl oxazoline); a polyurethane; a carboxymethyl cellulose; a hydroxyalkylated cellulose; a polypeptide; a nucleic acid; a modified nucleic acid; a locked nucleic acid; a polysaccharide; a carbohydrate; heparan sulfate; chondroitin sulfate; heparin, alginate; and a combination thereof; and wherein —○ represents a point of attachment to either one of the sulfur atom of one of the P—$C_t$—S— moieties of formula (B) or a thioether moiety of another subunit of the polymeric moiety of formula (Qa).

Embodiment 53. The compound of embodiment 50, wherein Q is a polymeric moiety of formula (Qb):

(Qb)

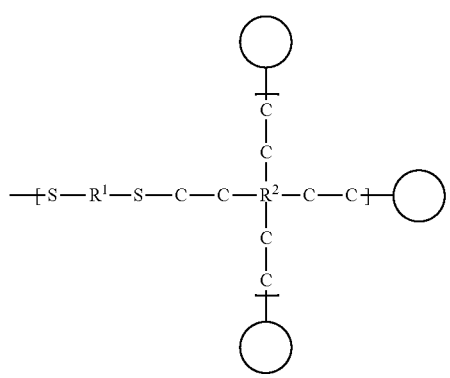

wherein, $R^1$ and $R^2$ are independently selected from the group consisting of poly(lactic acid) (PLA); polyglycolide (PGA); a copolymer of PLA and PGA (PLGA); poly(vinyl alcohol) (PVA); poly(ethylene glycol) (PEG); poly(ethylene oxide); a poly(ethylene oxide)-co-poly(propylene oxide) block copolymer; a poloxamine; a polyanhydride; a polyorthoester; a poly(hydroxy acids); a polydioxanone; a polycarbonate; a polyaminocarbonate; a poly(vinyl pyrrolidone); a poly(ethyl oxazoline); a polyurethane; a carboxymethyl cellulose; a hydroxyalkylated cellulose; a polypeptide; a nucleic acid; a modified nucleic acid; a locked nucleic acid; a polysaccharide; a carbohydrate; heparan sulfate; chondroitin sulfate; heparin, alginate; and a combination thereof; and wherein —O represents a point of attachment to either one of the sulfur atom of one of the P—$C_t$—S— moieties of formula (B) or a thioether moiety of another subunit of the polymeric moiety of formula (Qb).

Embodiment 54. A polymeric material [e.g. to a thiol-ene hydrogel] comprising repeating units of the formula (I):

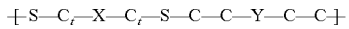 (I)

wherein X is a polypeptide, t≥2, $C_t$ is a linker comprising at least two carbon atoms, and Y is selected from the group consisting of poly(lactic acid) (PLA); polyglycolide (PGA); a copolymer of PLA and PGA (PLGA); poly(vinyl alcohol) (PVA); poly(ethylene glycol) (PEG); poly(ethylene oxide); a poly(ethylene oxide)-co-poly(propylene oxide) block copolymer; a poloxamine; a polyanhydride; a polyorthoester; a poly(hydroxy acids); a polydioxanone; a polycarbonate; a polyaminocarbonate; a poly(vinyl pyrrolidone); a poly(ethyl oxazoline); a polyurethane; a carboxymethyl cellulose; a hydroxyalkylated cellulose; a polypeptide; a nucleic acid; a modified nucleic acid; a locked nucleic acid; a polysaccharide; a carbohydrate; heparan sulfate; chondroitin sulfate; heparin, alginate; and a combination thereof.

Embodiment 55. The polymeric material of embodiment 54, further comprising a biologically active component associated with the polymer matrix of the polymeric material.

Embodiment 56. A polymeric material [e.g. to a thiol-ene hydrogel] comprising repeating units of the formula (II):

(II)

wherein X is a polypeptide, t≥2, $C_t$ is a linker comprising at least two carbon atoms (i.e., X is linked to at least two thioether moieties via a linker of two carbon atoms in length or longer), and Y is selected from the group consisting of poly(lactic acid) (PLA); polyglycolide (PGA); a copolymer of PLA and PGA (PLGA); poly(vinyl alcohol) (PVA); poly(ethylene glycol) (PEG); poly(ethylene oxide); a poly(ethylene oxide)-co-poly(propylene oxide) block copolymer; a poloxamine; a polyanhydride; a polyorthoester; a poly(hydroxy acids); a polydioxanone; a polycarbonate; a polyaminocarbonate; a poly(vinyl pyrrolidone); a poly(ethyl oxazoline); a polyurethane; a carboxymethyl cellulose; a hydroxyalkylated cellulose; a polypeptide; a nucleic acid; a modified nucleic acid; a locked nucleic acid; a polysaccharide; a carbohydrate; heparan sulfate; chondroitin sulfate; heparin, alginate; and a combination thereof; wherein —O represents a point of attachment to a thioether moiety of another subunit of the polymeric moiety of formula (II).

Embodiment 57. A polymeric material [e.g. to a thiol-ene hydrogel] comprising repeating units of the formula (III):

(III)

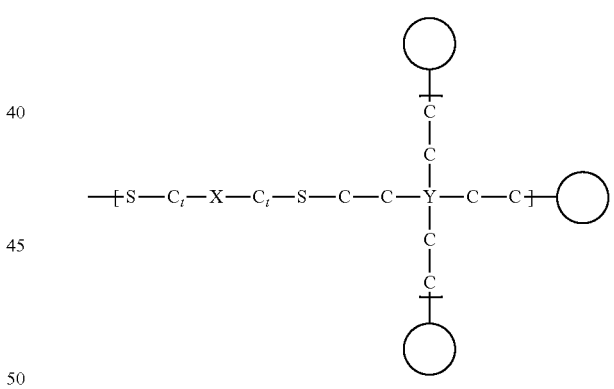

wherein X is a polypeptide, t≥2, $C_t$ is a linker comprising at least two carbon atoms (i.e., X is linked to at least two thioether moieties via a linker of two carbon atoms in length or longer), and Y is selected from the group consisting of poly(lactic acid) (PLA); polyglycolide (PGA); a copolymer of PLA and PGA (PLGA); poly(vinyl alcohol) (PVA); poly(ethylene glycol) (PEG); poly(ethylene oxide); a poly(ethylene oxide)-co-poly(propylene oxide) block copolymer; a poloxamine; a polyanhydride; a polyorthoester; a poly(hydroxy acids); a polydioxanone; a polycarbonate; a polyaminocarbonate; a poly(vinyl pyrrolidone); a poly(ethyl oxazoline); a polyurethane; a carboxymethyl cellulose; a hydroxyalkylated cellulose; a polypeptide; a nucleic acid; a modified nucleic acid; a locked nucleic acid; a polysaccharide; a carbohydrate; heparan sulfate; chondroitin sulfate; heparin, alginate; and a combination thereof; wherein —◯ represents a point of attachment to a thioether moiety of another subunit of the polymeric moiety of formula (III).

Embodiment 58. A compound of formula (C):

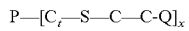
P—[C$_t$—S—C—C-Q]$_x$ wherein P is a polypeptide, C$_t$ is a linker comprising at least one carbon atom, t≥1, x is 1 or an integer greater than 1 and Q is a biological active component (e.g., a drug, a toxin or a pesticide), a polymer moiety (e.g., PEG), a capture moiety (e.g., biotin), a label (e.g., a fluorescent label, a chromophore, or a fluorophore), a sugar or carbohydrate, a nucleic acid, or a second polypeptide and wherein each residue of P comprising a C$_t$ linker may be selected from the group consisting of a natural amino acid residue, a rare amino acid residue, an unnatural amino acid residue, an amino acid analog residue or an amino acid mimetic residue, provided that the natural amino acid residue comprising the C$_t$ linker is not a cysteine residue.

Embodiment 59. The compound of embodiment 58, wherein the compound is produced by reacting a compound of formula P—[C$_t$—SH]$_x$ and a compound of formula CH$_2$=CH-Q and a radical initiator.

Embodiment 60. A compound of formula (D):

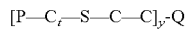
[P—C$_t$—S—C—C]$_y$-Q wherein P is a polypeptide, C$_t$ is a linker comprising at least one carbon atom, t≥1, wherein each residue of P comprising a C$_t$ linker may be selected from the group consisting of a natural amino acid residue, a rare amino acid residue, an unnatural amino acid residue, an amino acid analog residue or an amino acid mimetic residue, provided that the natural amino acid residue comprising the C$_t$ linker is not a cysteine residue; y is 1 or an integer greater than 1 (e.g. 2, 3, 4 or more) and Q is selected from the group consisting of poly(lactic acid) (PLA); polyglycolide (PGA); a copolymer of PLA and PGA (PLGA); poly(vinyl alcohol) (PVA); poly(ethylene glycol) (PEG); poly(ethylene oxide); a poly(ethylene oxide)-co-poly(propylene oxide) block copolymer; a poloxamine; a polyanhydride; a polyorthoester; a poly(hydroxy acids); a polydioxanone; a polycarbonate; a polyaminocarbonate; a poly(vinyl pyrrolidone); a poly(ethyl oxazoline); a polyurethane; a carboxymethyl cellulose; a hydroxyalkylated cellulose; a polypeptide; a nucleic acid; a modified nucleic acid; a locked nucleic acid; a polysaccharide; a carbohydrate; heparan sulfate; chondroitin sulfate; heparin, alginate; and a combination thereof.

Embodiment 61. The compound of embodiment 60, wherein the compound is produced by reacting a compound of formula P—C$_t$—SH and a compound of formula [CH2=CH]$_y$Q and a radical initiator.

Embodiment 62. The compound of embodiment 60, wherein Q is a polymeric moiety of formula (Qc):

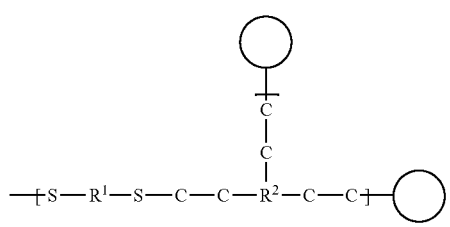
(Qc)

wherein, R$^1$ and R$^2$ are independently selected from the group consisting of poly(lactic acid) (PLA); polyglycolide (PGA); a copolymer of PLA and PGA (PLGA); poly(vinyl alcohol) (PVA); poly(ethylene glycol) (PEG); poly(ethylene oxide); a poly(ethylene oxide)-co-poly(propylene oxide) block copolymer; a poloxamine; a polyanhydride; a polyorthoester; a poly(hydroxy acids); a polydioxanone; a polycarbonate; a polyaminocarbonate; a poly(vinyl pyrrolidone); a poly(ethyl oxazoline); a polyurethane; a carboxymethyl cellulose; a hydroxyalkylated cellulose; a polypeptide; a nucleic acid; a modified nucleic acid; a locked nucleic acid; a polysaccharide; a carbohydrate; heparan sulfate; chondroitin sulfate; heparin, alginate; and a combination thereof; and wherein —◯ represents a point of attachment to either one of the sulfur atom of one of the P—C$_t$—S— moieties of formula (D) or a thioether moiety of another subunit of the polymeric moiety of formula (Qc).

Embodiment 63. The compound of embodiment 60, wherein Q is a polymeric moiety of formula (Qd):

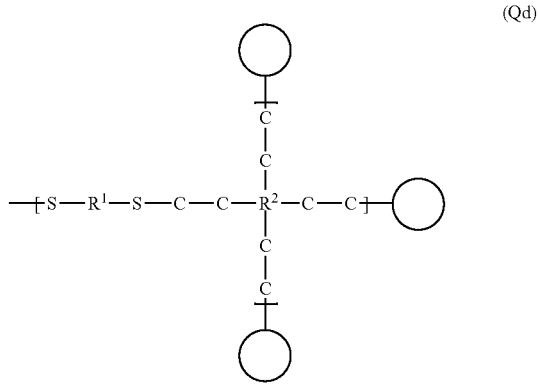
(Qd)

wherein, R$^1$ and R$^2$ are independently selected from the group consisting of poly(lactic acid) (PLA); polyglycolide (PGA); a copolymer of PLA and PGA (PLGA); poly(vinyl alcohol) (PVA); poly(ethylene glycol) (PEG); poly(ethylene oxide); a poly(ethylene oxide)-co-poly(propylene oxide) block copolymer; a poloxamine; a polyanhydride; a polyorthoester; a poly(hydroxy acids); a polydioxanone; a polycarbonate; a polyaminocarbonate; a poly(vinyl pyrrolidone); a poly(ethyl oxazoline); a polyurethane; a carboxymethyl cellulose; a hydroxyalkylated cellulose; a polypeptide; a nucleic acid; a modified nucleic acid; a locked nucleic acid; a polysaccharide; a carbohydrate; heparan sulfate; chondroitin sulfate; heparin, alginate; and a combination thereof; and wherein —◯ represents a point of attachment to either one of the sulfur atom of one of the P—C$_t$—S— moieties of formula (D) or a thioether moiety of another subunit of the polymeric moiety of formula (Qd).

Embodiment 64. A polymeric material (e.g. a thiol-ene hydrogel) comprising repeating units of the formula (IV):

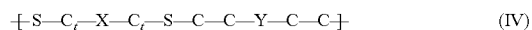
$+$S—C$_t$—X—C$_t$—S—C—C—Y—C—C$+$ (IV)

wherein X is a polypeptide, t≥1 and C$_t$ is a linker comprising at least one carbon atom, wherein each residue of X comprising a C$_t$ linker may be selected from the group consisting of a natural amino acid residue, a rare amino acid residue, an unnatural amino acid residue, an amino acid analog residue or an amino acid mimetic residue, provided that the natural amino acid residue comprising the C$_t$ linker is not a cysteine residue, and Y is selected from the group consisting of poly(lactic acid) (PLA); polyglycolide (PGA); a copolymer of PLA and PGA (PLGA); poly(vinyl alcohol) (PVA); poly(ethylene glycol) (PEG); poly(ethylene oxide); a poly (ethylene oxide)-co-poly(propylene oxide) block copolymer; a poloxamine; a polyanhydride; a polyorthoester; a poly(hydroxy acids); a polydioxanone; a polycarbonate; a polyaminocarbonate; a poly(vinyl pyrrolidone); a poly(ethyl oxazoline); a polyurethane; a carboxymethyl cellulose; a hydroxyalkylated cellulose; a polypeptide; a nucleic acid; a modified nucleic acid; a locked nucleic acid; a polysaccharide; a carbohydrate; heparan sulfate; chondroitin sulfate; heparin, alginate; and a combination thereof.

Embodiment 65. The polymeric material of embodiment 64, further comprising a biologically active component associated with the polymer matrix of the polymeric material.

Embodiment 66. A polymeric material [e.g. to a thiol-ene hydrogel] comprising repeating units of the formula (V):

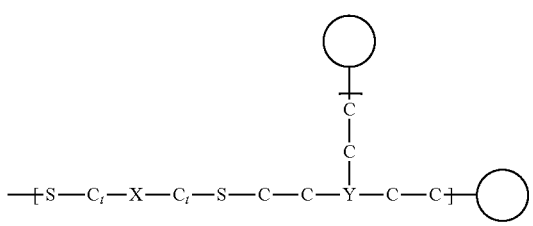

(V)

wherein X is a polypeptide, $t \geq 1$ and $C_t$ is a linker comprising at least one carbon atom, wherein each residue of X comprising a $C_t$ linker may be selected from the group consisting of a natural amino acid residue, a rare amino acid residue, an unnatural amino acid residue, an amino acid analog residue or an amino acid mimetic residue, provided that the natural amino acid residue comprising the $C_t$ linker is not a cysteine residue, and Y is selected from the group consisting of poly(lactic acid) (PLA); polyglycolide (PGA); a copolymer of PLA and PGA (PLGA); poly(vinyl alcohol) (PVA); poly(ethylene glycol) (PEG); poly(ethylene oxide); a poly (ethylene oxide)-co-poly(propylene oxide) block copolymer; a poloxamine; a polyanhydride; a polyorthoester; a poly(hydroxy acids); a polydioxanone; a polycarbonate; a polyaminocarbonate; a poly(vinyl pyrrolidone); a poly(ethyl oxazoline); a polyurethane; a carboxymethyl cellulose; a hydroxyalkylated cellulose; a polypeptide; a nucleic acid; a modified nucleic acid; a locked nucleic acid; a polysaccharide; a carbohydrate; heparan sulfate; chondroitin sulfate; heparin, alginate; and a combination thereof; wherein —◯ represents a point of attachment to a thioether moiety of another subunit of the polymeric moiety of formula (V).

Embodiment 67. A polymeric material [e.g. to a thiol-ene hydrogel] comprising repeating units of the formula (VI):

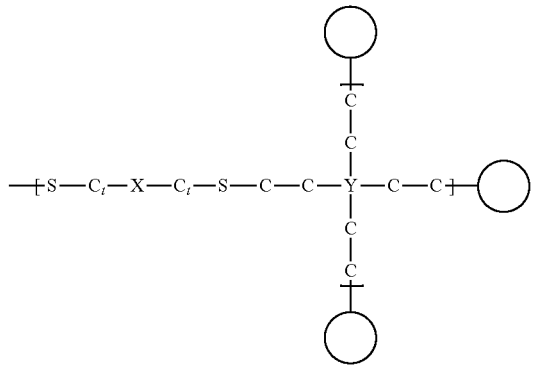

(VI)

wherein X is a polypeptide, $t \geq 1$ and $C_t$ is a linker comprising at least one carbon atom, wherein each residue of X comprising a $C_t$ linker may be selected from the group consisting of a natural amino acid residue, a rare amino acid residue, an unnatural amino acid residue, an amino acid analog residue or an amino acid mimetic residue, provided that the natural amino acid residue comprising the $C_t$ linker is not a cysteine residue, and Y is selected from the group consisting of poly(lactic acid) (PLA); polyglycolide (PGA); a copolymer of PLA and PGA (PLGA); poly(vinyl alcohol) (PVA); poly(ethylene glycol) (PEG); poly(ethylene oxide); a poly (ethylene oxide)-co-poly(propylene oxide) block copolymer; a poloxamine; a polyanhydride; a polyorthoester; a poly(hydroxy acids); a polydioxanone; a polycarbonate; a polyaminocarbonate; a poly(vinyl pyrrolidone); a poly(ethyl oxazoline); a polyurethane; a carboxymethyl cellulose; a hydroxyalkylated cellulose; a polypeptide; a nucleic acid; a modified nucleic acid; a locked nucleic acid; a polysaccharide; a carbohydrate; heparan sulfate; chondroitin sulfate; heparin, alginate; and a combination thereof; wherein —◯ represents a point of attachment to a thioether moiety of another subunit of the polymeric moiety of formula (VI).

Embodiment 68. A method for treating a condition or disorder in a subject in need thereof comprising administering a modified polypeptide of embodiment 35; a biologically active component associated with a biocompatible cross-linked degradable hydrogel polymer of embodiment 46; a compound of embodiment 48; a compound of embodiment 50; a biologically active component associated with a polymeric material of embodiment 54; a biologically active component associated with a polymeric material of embodiment 56; a biologically active component associated with a polymeric material of embodiment 57; a compound of embodiment 58; a compound of embodiment 60; a biologically active component associated with a polymeric material of embodiment 64; a biologically active component associated with a polymeric material of embodiment 66; or a biologically active component associated with a polymeric material of embodiment 67.

Embodiment 69. A method for regenerating tissue comprising releasing a cell or a tissue encapsulated in a biocompatible cross-linked degradable hydrogel polymer of embodiment 46 at a site of damaged or defective tissue.

Embodiment 70. The method according to embodiment 69, further comprising producing a composition comprising the biocompatible cross-linked degradable hydrogel polymer at the site of damaged or defective tissue.

Embodiment 71. A kit comprising a modified polypeptide of embodiment 35; a biologically active component associated with a biocompatible cross-linked degradable hydrogel polymer of embodiment 46; a compound of embodiment 48; a compound of embodiment 50; a biologically active component associated with a polymeric material of embodiment 54; a biologically active component associated with a polymeric material of embodiment 56; a biologically active component associated with a polymeric material of embodiment 57; a compound of embodiment 58; a compound of embodiment 60; a biologically active component associated with a polymeric material of embodiment 64; a biologically active component associated with a polymeric material of embodiment 66; or a biologically active component associated with a polymeric material of embodiment 67.

Embodiment 72. An article of manufacture comprising a modified polypeptide of embodiment 35; a biologically active component associated with a biocompatible cross-linked degradable hydrogel polymer of embodiment 46; a compound of embodiment 48; a compound of embodiment 50; a biologically active component associated with a polymeric material of embodiment 54; a biologically active component associated with a polymeric material of embodiment 56; a biologically active component associated with a polymeric material of embodiment 57; a compound of embodiment 58; a compound of embodiment 60; a biologically active component associated with a polymeric material of embodiment 64; a biologically active component associated with a polymeric material of embodiment 66; or a biologically active component associated with a polymeric material of embodiment 67.

EXAMPLES

The following Examples are provided to illustrate but not to limit the invention.

Example 1: Incorporation of Homocysteine and 2-amino-5-sulfanyl Pentanoic Acid into Synthetic Oligopeptides Upon Solid-Phase Synthesis Cysteine-containing oligopeptides of the sequences KCGPQGIAGQCK ("MMPA") (SEQ ID NO: 1) and CALKVLKGC ("C2xPC") (SEQ ID NO: 2) were synthesized by solid-phase Fmoc synthesis procedure on rinkamide resin according to the methods well established in the art (see Chan W. C. and White P. D. 2000).

To site-specifically incorporate homocysteine or 2-amino-5-sulfanyl pentanoic acid residues in place of the cysteine in these sequences, the Fmoc-protected building blocks (S)-2-(Fmoc-amino)-4-tritylsulfanyl-butyric acid (Bachem) or (S)-Fmoc-2-amino-5-(tritylthio)-pentanoic acid (PolyPeptide) were used in the synthetic procedure instead of the common building blocks for cysteine (e.g. Fmoc-L-Cys(Trt)-OH). The synthesized oligopeptides are cleaved from the resin, deprotected and purified using standard methods known in the art.

Example 2: Incorporation of Non-Natural Thiols into Synthetic Oligopeptide

Procedure 1: On-Resin Selective Thiolation of Peptides with NHS-PEG-Thiol

To create a dithiol peptide crosslinker without the incorporation of two cysteine amino acids, the following peptide was synthesized at a 0.5 mmol scale with standard Fmoc chemistries on an automated Solid-Phase Peptide Synthesizer (Tribute, Protein Technologies): GPQ$^{(trt)}$GIWGQ$^{(trt)}$ GK$^{(Dde)}$G-resin (SEQ ID NO: 3). A final deprotection step was included to remove the N-terminal Fmoc from the peptide, leaving a free terminal amine: NH2-GPQ$^{(trt)}$ GIWGQ$^{(trt)}$GK$^{(Dde)}$G-resin (SEQ ID NO: 3). The Dde protective group on K$^{(Dde)}$ was then removed by incubating the peptide-resin in 20 ml DMF+2% hydrazine for 10 minutes at room temperature (this deprotection step was repeated 3 times) to create NH2-GPQ$^{(trt)}$GIWGQ$^{(trt)}$GK$^{(NH2)}$G-resin (SEQ ID NO: 4). The peptide-resin was then washed with DMF to remove hydrazine and weighed (5.5 g of the peptide-resin was recovered).

51.4 mg of the peptide-resin was then transferred to a separate glass reaction vessel (Based on a 0.5 mmol synthesis yielding 5.5 g of peptide-resin, 51.4 mg would be approximately 0.005 mmol peptide). 1 ml of anhydrous DMF (Sigma), 100 mg of 3.5 KDa NHS-PEG-SH (Nanocs), and 9 μl Diisopropylethylamine (Sigma) were then added to the reaction vessel and stirred at room temperature for >24 hours. The presence of free amines was then tested in a Ninhydrin Test (2 μl beads is removed from the reaction and incubated at 100° C. for 2 minutes with 40 μl 5% ninhydrin in ethanol, 40 μl phenol in ethanol (at 4:1 ratio), and 40 μl pyridine. In this test, the presence of free amines is detected by the appearance of a purple color). Though unreacted peptide-resin produced substantial purple color in this test, the beads taken from the NHS-PEG-SH reaction showed no purple color in side-by-side tests, indicating that the free amines had been successfully reacted with NHS-PEG-SH. The peptide was then cleaved from the resin by reacting with 1 ml of a cleavage cocktail (0.5 ml H$_2$O, 0.25 g phenol, 0.25 g Dithiothreitol (DTT), 0.125 ml Triisopropylsilane (TIPS), 5 ml Trifluoroacetic acid (TFA). This step also removed the Trt protective groups on Q$^{(trt)}$. The peptide was recovered by precipitation in ether.

Procedure 2: On-Resin Selective Thiolation of Peptides with Mercapto-Acid

To create a dithiol peptide crosslinker without the incorporation of two cysteine amino acids, the following peptide is synthesized at a 0.5 mmol scale with standard Fmoc chemistries on an automated Solid-Phase Peptide Synthesizer (Tribute, Protein Technologies): GK$^{(Boc)}$K$^{(Dde)}$Q$^{(trt)}$ GIWGQ$^{(trt)}$GK$^{(Dde)}$K$^{(Boc)}$G-resin (SEQ ID NO: 5). A final deprotection and capping step is included to remove the N-terminal Fmoc from the peptide and cap the free terminal amine. The Dde protective groups on K$^{(Dde)}$ is then removed by incubating the peptide-resin in 20 ml DMF+2% hydrazine for 10 minutes at room temperature (this deprotection step is repeated 3 times) to create GK$^{(Boc)}$K$^{(NH2)}$Q$^{(trt)}$ GIWGQ$^{(trt)}$GK$^{(NH2)}$K$^{(Boc)}$G-resin (SEQ ID NO: 6). The peptide resin is washed multiple times with DCM to remove residual hydrazine and then place in a reaction glass vessel with 10 ml of anhydrous DCM.

A second reaction is performed by mixing 600 mg NHS, 800 μl Diisopropylcarbodiimide (DIC), and 440 μl 3-mercapto-propionic acid in anhydrous DCM with a small amount of Dimethylaminopyridine (DMAP). During this reaction, as visible precipitate is formed, indicating the successful activation of NHS. This reaction is filtered to remove the precipitate and then added to the peptide-resin in DCM. The combined peptide-resin and activated NHS is mixed at room temperature for 30 minutes for complete conversion of K$^{(NH2)}$ to K$^{(N-CCC-SH)}$ as monitored by the Ninhydrin Test (described in the previous procedure).

The peptide is then cleaved from the resin by reacting with a cleavage cocktail (1.0 ml H$_2$O, 0.5 g phenol, 0.5 g Dithiothreitol (DTT), 0.25 ml Triisopropylsilane (TIPS), 10 ml Trifluoroacetic acid (TFA). This step also removes the Boc and Trt protective groups from $K^{(Boc)}$ and $Q^{(trt)}$. The peptide is recovered by precipitation in ether.

Alternatively to the previously described procedures, a number of thiolating agents known in the art can be used to convert selectively deprotected amino groups into non-cysteine thiols, for instance commercially available N-succinimidyl-S-acetylthiopropionate (SATP) or N-acetyl Homocysteine Thiolactone.

Example 3: Incorporation of Non-Cysteine Thiol Groups into Collagen

Rat tail collagen dissolved at ~3 mg/mL concentration in 20 mM acetic acid (Corning) is dialyzed against solution of 6 M urea in phosphate buffer at pH 8.0 overnight at +4° C. The dialyzed denatured collagen is subsequently treated with 1:100 (vol:vol) of 55 mM solution of N-succinimidyl-S-acetylthiopropionate (SATP) in dimethylsulfoxide for 2 hours at ambient temperature. Unreacted SATP and dimethylsulfoxide are removed by overnight dialysis at +4° C. against 6 M urea in phosphate buffer, pH 7.4. The thiol groups attached to the denatured collagen are deacetylated by treating the protein solution with 1:10 (vol:vol) of 0.5 M hydroxylamine, 25 mM EDTA in phosphate buffer pH 7.4 for 2 hours at ambient temperature and the urea, buffer and low-molecular weight products of deacylation step are removed by extensive dialysis against 20 mM acetic acid at +4° C.

Example 4: Kinetics of Photopolymerization of Thiol-Ene Hydrogels Using a Di-Cysteine Crosslinker and a PEG-Dithiol Crosslinker 100 microliter samples containing 6% (wt/vol) of 4-arm 20 kDa PEG tetranorbornene (Fairbanks), 0.01% (wt/vol) of sodium phenyl-2,4,6-trimethylbenzoylphosphinate (or NAP) (Fairbanks 2), 50 mM sodium acetate buffer pH 5.0 and 6 mM of dithiol crosslinker (stoichiometric ratio of norbornene to thiol) were prepared. Dithiol crosslinkers included either linear PEG-dithiol, 3.5 kDa (JenKem USA) or a synthetic di-cysteine containing oligopeptide peptide "MMPA" (amino acid sequence KCGPQGIAGQCK (SEQ ID NO: 1)). All samples were prepared and analyzed in duplicates.

Figure 5:
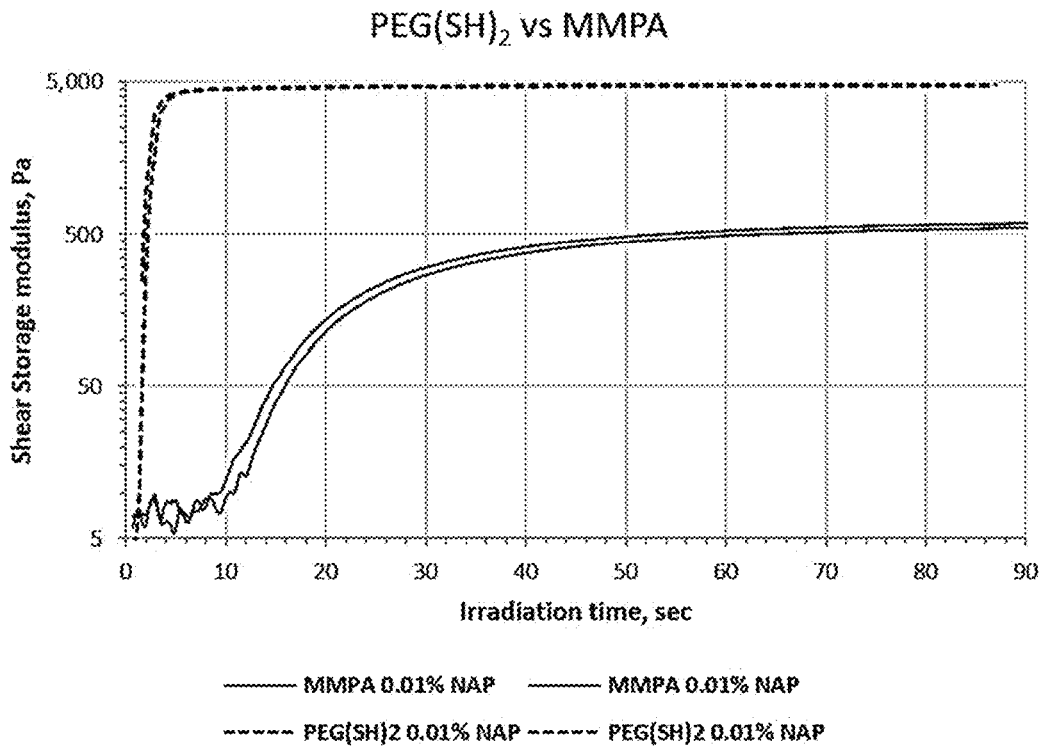
FIG. 5 shows the rheological trace of hydrogel photopolymerization demonstrating slow reaction rate of a di-cysteine crosslinker vs. a PEG-dithiol crosslinker.

Real-time kinetics of hydrogel photopolymerization was followed by in situ dynamic rheology with parallel plate geometry on a Discovery HR-3 rheometer (TA Instruments). 385 nm light at 19 mW/cm$^2$ was directed through a flat quartz plate through the sample, while dynamic stress measurements were made at a 0.250 mm gap, 1% strain, and 10 rad/s at ambient temperature. Strain sweeps were performed post polymerization to verify the linear response regime. Polymerization was followed until the shear storage modulus (G') reached a plateau (FIG. 5), indicating completion of photopolymerization reaction.

Inspection of the data reveals that G' reaches plateau values within less than 10 s of irradiation if PEG dithiol is used as the crosslinker, while a substantially longer time (over 80 s) is required if the di-cysteine peptide MMPA is used.

Example 5: Rates of Consumption of Free Thiol Groups for Multiple Thiol Containing Compounds in the Course of Photo-Induced Thiol-Ene Reaction To compare relative reactivities of various thiol-bearing compounds in photoinitiated thiol-ene reaction, 200 microliter solutions containing 6 mM linear PEG dinorbornene (MW 3.8 kDa), 0.01% (wt/vol) NAP, 50 mM sodium acetate pH 5.0 and the thiol-bearing compound at 12 mM concentration of thiols (stoichiometric with concentration of norbornenes) were prepared and irradiated with 385 nm light at 19 mW/cm$^2$ in a flat-bottom 96-well tissue culture plate. The thiol-bearing compounds tested included β-mercaptoethanol, methoxy PEG thiol (MW 5 kDa, "MME-PEG5K-SH"), cysteine hydrochloride and a synthetic dicysteine-containing oligopeptide "C2xPC" (aminoacid sequence CALKVLKGC (SEQ ID NO: 2)).

At specified time points, 10 microliter aliquots were withdrawn from the reaction mixture, diluted 12-fold with deionized water and the concentration of the remaining free thiol was measured by Ellman's assay as follows. In a transparent, flat-bottom 96-well plate, 20 microliters of the diluted sample was mixed with 200 microliters of 200 micromolar solution of 5,5'-dithiobis-(2-nitrobenzoic acid) in 50 mM sodium phosphate, pH 7.4 and incubated at ambient temperature for 15 minutes. Optical density at 405 nm resulting from 2-nitro-5-thiobenzoate released by free thiol in the sample was determined with a BioTek ELx800 plate reader. Freshly prepared dilution series of cysteine hydrochloride from 0.063 mM to 1.46 mM was processed in the same way and, upon fitting by linear regression in Microsoft Excel provided a first-order equation relating concentration of the free thiol in the sample and optical density at 405 nm that was used to calculate concentration of free thiols in irradiated samples.

Figure 6:
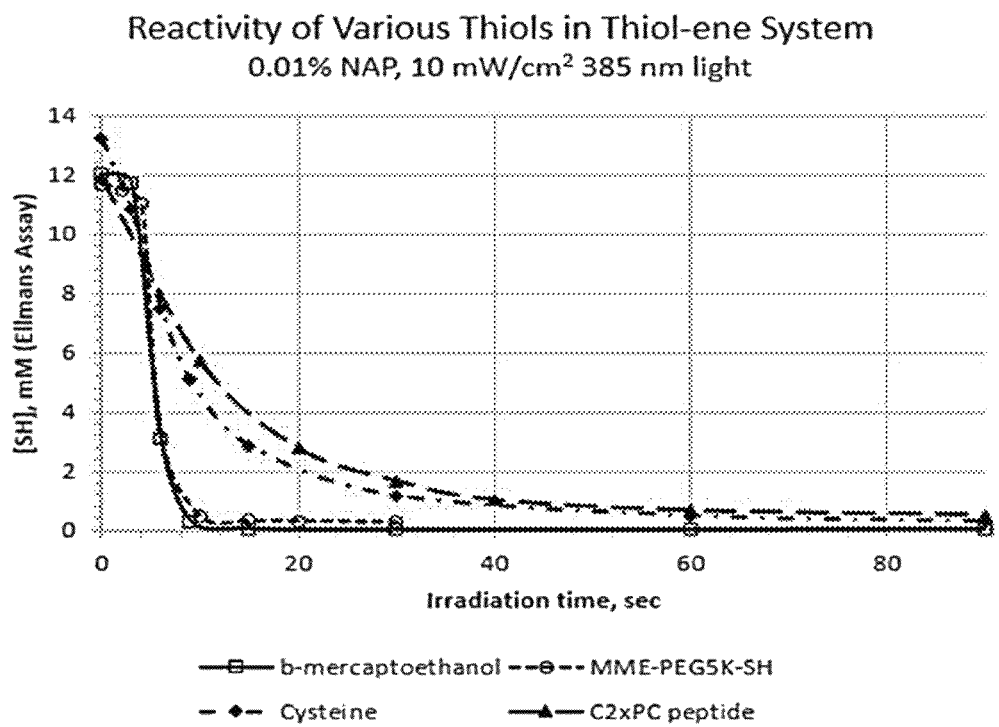
FIG. 6 shows results from the Ellman's assay demonstrating the consumption of free thiol groups for multiple thiol containing compounds in the course of photoinitiated thiol-ene reaction.

The kinetics of consumption of free thiols in the course of photo-induced thiol-ene reaction is shown in FIG. 6 for all four compounds tested. It should be pointed out that kinetic curves are clearly separated into two different classes, with β-mercaptoethanol and MME-PEG5K-SH reacting to completion within just 10 seconds of irradiation and both cysteine-containing compounds (cysteine and C2xPC oligopeptide) reacting much slower and achieving near-completion by 90 seconds of irradiation.

It should also be pointed out that the thiol-ene reaction conditions employed in this experiment are essentially the same as in the Example 4 above, except the products of the reactions here are linear, water-soluble molecules instead of covalently crosslinked networks as formed in Example 4. Direct comparison of the kinetic curves in FIGS. 5 and 6 reveals that differences in the rates of network formation between cysteine-containing crosslinkers and thiol-bearing PEGs are primarily due to the differences in the reactivity of the thiol functional groups presented by these classes of compounds, with cysteine-based thiols exhibiting unusually slow reactivity in the photo-induced thiol-ene reaction.

Example 6: Damage of Chicken Egg Lysozyme by Cysteine-Mediated Thiol-Ene Reaction 50 microliter solutions containing 1.4 mg/mL chicken egg lysozyme, 6 mM linear PEG dinorbornene (MW 3.8 kDa), 0.01% (wt/vol) NAP, 50 mM sodium acetate pH 5.0 and the thiol-bearing compound at 12 mM concentration of thiols (stoichiometric with concentration of norbornenes) were prepared and irradiated from above with 385 nm light at 19 mW/cm$^2$ in open 1.5 mL Eppendorf tubes. The thiol-bearing compounds included cysteine (slow reaction) or methoxy PEG thiol (fast reaction). Irradiation times were 90 seconds for slow reaction and 10 seconds for fast reaction. These irradiation times under the chosen conditions result in complete consumption of the thiols in the slow and fast reactions (FIG. 6; Example 5) and are sufficient to drive the formation of covalently crosslinked network to completion, if corresponding multi-arm norbornene- and thiol-bearing monomers are used as in Example 4.

Irradiated samples and non-irradiated controls were diluted ~800-fold into LDS gel loading buffer (Invitrogen) and reaction products were analyzed by SDS-PAGE on 12% Novex NuPage gel (Invitrogen) followed by silver staining (SilverQuest staining kit, Invitrogen).

Figure 7:
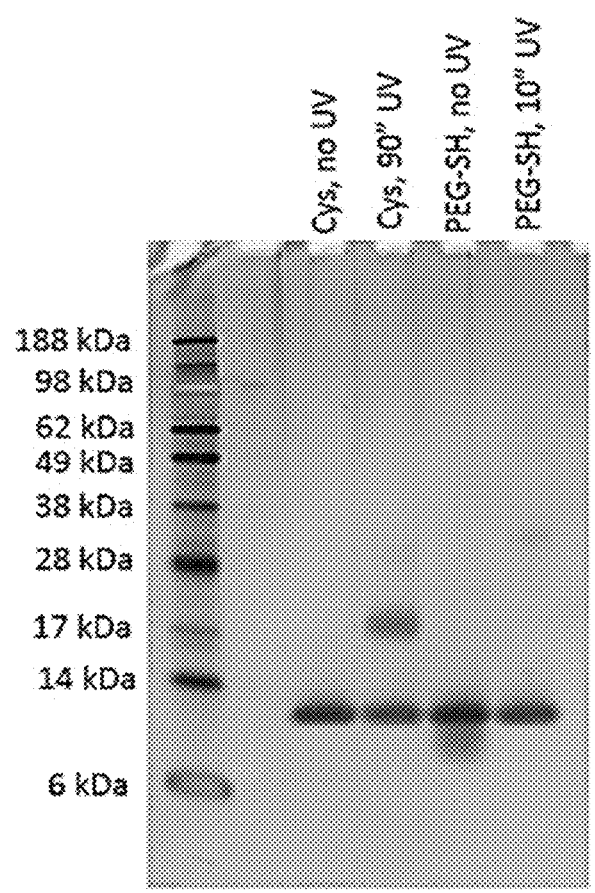
FIG. 7 shows the SDS-PAGE experiment demonstrating protein damage under the conditions required to incorporate a di-cysteine containing peptide into a thiol-ene polymer.

The result is shown in FIG. 7. Exposure of lysozyme to the fast thiol-ene process for the time required to completely photopolymerize PEG-thiol crosslinked hydrogel results in no detectable change in the protein mobility, compared to untreated control (lanes "PEG-SH, no UV" versus "PEG-SH, 10" UV"), indicating that the cargo protein (lysozyme) remains intact. In turn, if the thiol-ene process is slow, exposure of the cargo protein to the reaction for the time necessary to achieve complete network formation results in appearance of a significant amount of slower-migrating protein form (lanes "Cys, no UV" versus "Cys, 90" UV"), consistent with involvement of the cargo protein in some secondary process, presumably resulting in addition of 3.8 kDa PEG dinorbornene, even though no free thiols are available in chicken egg lysozyme in its native state.

This example illustrates an important difference in bio-orthogonality between fast and slow thiol-ene reactions, with thiol-ene process mediated by more reactive thiol moieties (e.g. methoxy-PEG-thiol) being truly bio-orthogonal (non-reactive to biomacromolecules lacking free thiols), and the process mediated by slower, cysteine-based thiols lacking bio-orthogonality, at least for some selected biomacromolecules (lysozyme).

Example 7: Rates of Consumption of Free Thiol Groups of Cysteine and Homocysteine-Containing Compounds in the Course of Photo-Induced Thiol-Ene Reaction To compare relative reactivities of cysteine and homocysteine-based thiols in photoinitiated thiol-ene reaction, 200 microliter solutions containing 6 mM linear PEG dinorbornene (MW 3.8 kDa), 0.01% (wt/vol) NAP, 50 mM sodium acetate pH 5.0 and the thiol-bearing compound at 12 mM concentration of thiols (stoichiometric with concentration of norbornenes) were prepared and irradiated with 385 nm light at 19 mW/cm$^2$ in a flat-bottom 96-well tissue culture plate. Thiol-bearing compounds tested included free amino acids cysteine and homocysteine as well as synthetic dicysteine-containing peptides "MMPA" and "C2xPC" (amino acid sequences KCGPQGIAGQCK (SEQ ID NO: 1) and CALKVLKGC (SEQ ID NO: 2)) and their analogs "hC MMPA" and "hC2xPhC" containing homocysteines instead of cysteines. At specified time points, 10 microliter aliquots were withdrawn from the reaction, diluted 12-fold with deionized water and the concentration of the remaining free thiol was measured by Ellman's assay as described in the Example 5 above.

The kinetics of consumption of free thiols for cysteine and homocysteine are compared in the FIG. 8, panel A and for the di-cysteine and di-homocysteine containing oligopeptides in FIG. 8, panel B. The rate of thiol consumption for free cysteine and dicysteine-containing peptides MMPA and C2xPC is essentially the same as in the Example 5 above, achieving near complete thiol consumption at around 90 seconds of irradiation. Free homocysteine reacts significantly faster and is completely consumed within just 20 seconds of irradiation (FIG. 8 panel A). Dihomocysteine-containing peptides hC MMPA and hC2xPhC react even faster, achieving complete thiol consumption within just 15 seconds of irradiation.

Example 8: Kinetics of Photopolymerization of Thiol-Ene Hydrogels Using a Dicysteine Crosslinker and a Dihomocysteine Crosslinker 100 microliter samples containing 6% (wt/vol) of 4-arm 20 kDa PEG tetranorbornene (Fairbanks), 0.01% (wt/vol) of sodium phenyl-2,4,6-trimethylbenzoylphosphinate (or NAP) (Fairbanks 2), 50 mM sodium acetate buffer pH 5.0 and 6 mM of dithiol crosslinker (stoichiometric ratio of norbornene to thiol) were prepared. Dithiol crosslinkers included either synthetic dicysteine-containing oligopeptide peptide "MMPA" (amino acid sequence KCGPQGIAGQCK (SEQ ID NO: 1)) or its dihomocysteine analog "hC MMPA" of identical sequence, but replacing each cysteine residue with homocysteine. All samples were prepared and analyzed in duplicates.

Real-time kinetics of hydrogel photopolymerization was followed by in situ dynamic rheology with parallel plate geometry on a Discovery HR-3 rheometer (TA Instruments). 385 nm light at 19 mW/cm$^2$ was directed through a flat quartz plate through the sample, while dynamic stress measurements were made at a 0.250 mm gap, 1% strain, and 10 rad/s at ambient temperature. Strain sweeps were performed post polymerization to verify the linear response regime. Polymerization was followed until the shear storage modulus (GD reached a plateau (FIG. 9), indicating completion of photopolymerization reaction.

Figure 9:
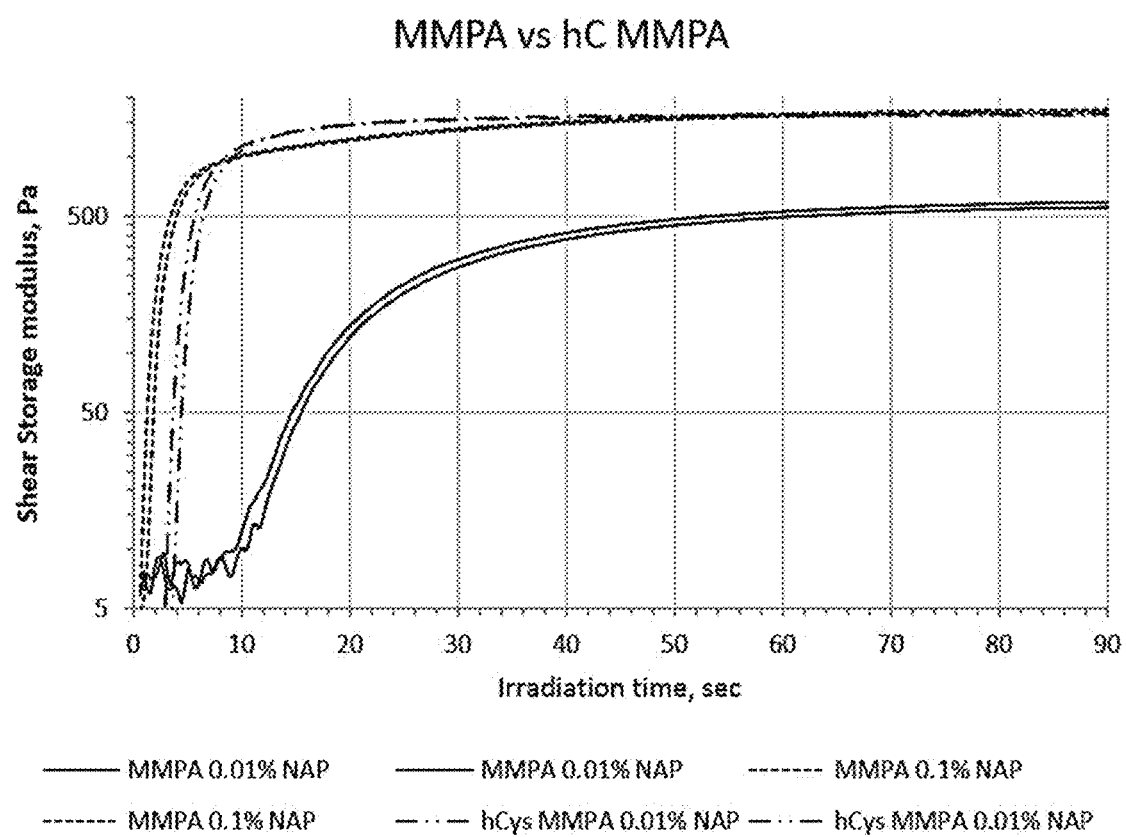
FIG. 9 shows the rheological trace of hydrogel photopolymerization demonstrating slow reaction rate of a di-cysteine crosslinker vs. a di-homocysteine crosslinker.

Inspection of the data reveals that G' reaches plateau values within 20 s of irradiation if a di-homocysteine peptide hC MMPA is used as the crosslinker, while a substantially longer time (over 80 s) is required if the di-cysteine peptide MMPA is used. In addition, the plateau value of G' for the MMPA-crosslinked network is substantially lower than that of the hC MMPA-crosslinked network, which is unexpected given nearly identical chemical composition of the monomers employed. This difference suggests that in the case of dicysteine-containing crosslinker the reaction is so slow that in the course of photopolymerization all initiator is consumed before the hydrogel network is fully formed, while with more reactive di-homocysteine crosslinkers the hydrogel is fully developed. To test this assumption, a photopolymerization experiment with MMPA crosslinker was repeated with tenfold higher concentration of initiator (0.1% NAP). As FIG. 9 shows, at this high concentration of initiator the overall rate of MMPA-mediated photopolymerization approaches that of the hC MMPA-mediated process at 0.01% NAP and the elastic properties of resulting networks are nearly identical. This increase in rate, however, comes at the cost of exposing the monomer solution and any biologically active cargo (e.g. encapsulated proteins) to a tenfold higher concentration of initiator and, therefore, higher concentration of free radicals, which may have detrimental effects on stability of the cargo.

Example 9: SDS-PAGE Analysis of Lysozyme Exposed to Homocysteine-Mediated Thiol-Ene Reaction 50 microliter solutions containing 1.4 mg/mL chicken egg lysozyme, 6 mM linear PEG dinorbornene (MW 3.8 kDa), 0.01% (wt/vol) NAP, 50 mM sodium acetate pH 5.0 and the thiol-bearing compound at 12 mM concentration of thiols (stoichiometric with concentration of norbornenes) were prepared and irradiated from above with 385 nm light at 19 mW/cm² in open 1.5 mL Eppendorf tubes. The thiol-bearing compounds included cysteine (slow reaction) or homocysteine (fast reaction). Irradiation times were 90 seconds for cysteine and 20 seconds for homocysteine. These irradiation times under the reaction chosen conditions result in complete consumption of the thiols in the slow and fast reactions (FIG. 8; Example 7) and are sufficient to drive the photopolymerization to completion, if multi-arm norbornene- and thiol-bearing monomers are used as in Example 8. In addition, a cysteine-mediated reaction was repeated at 10-fold higher concentration of initiator (0.1% NAP) with irradiation for 10 seconds in order to assess potential for cargo protein damage caused by exposure to conditions resulting in complete network formation in the course of cysteine-mediated photopolymerization, as discussed in the Example 8 above.

Irradiated samples and non-irradiated controls were diluted ~800-fold into LDS gel loading buffer (Invitrogen) and reaction products were analyzed by SDS-PAGE on 12% Novex NuPage gel (Invitrogen) followed by silver staining (SilverQuest staining kit, Invitrogen).

Figure 10:
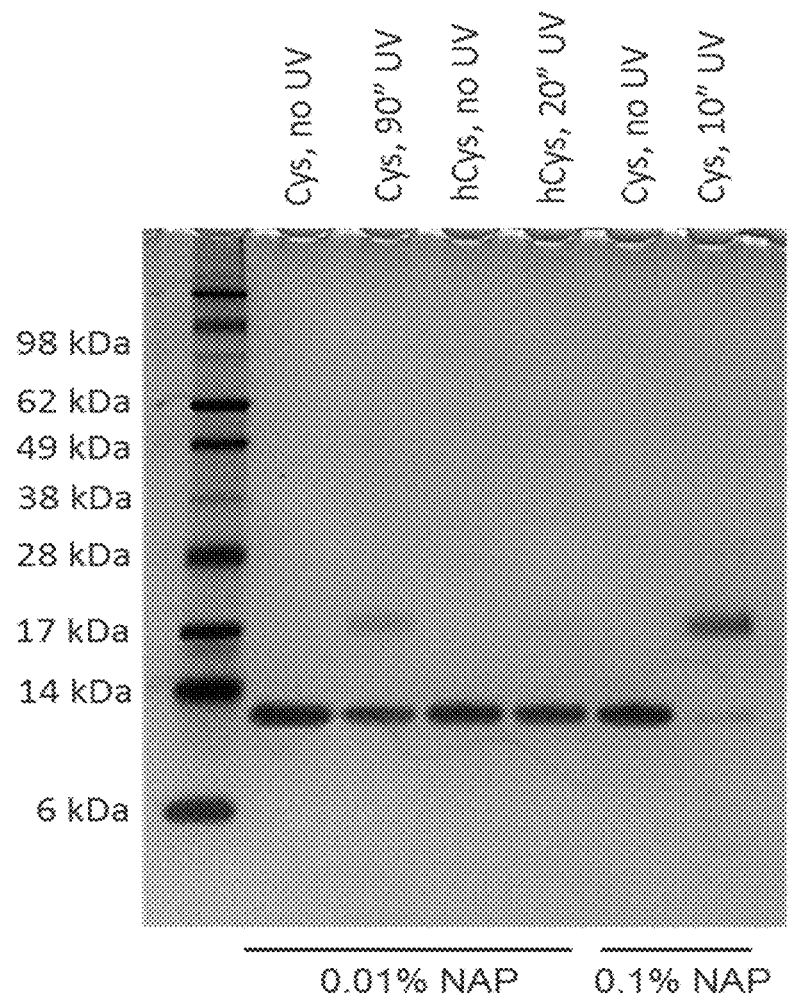
FIG. 10 shows the SDS-PAGE experiment demonstrating protein damage under the conditions required to incorporate a di-cysteine containing peptide into a thiol-ene polymer and the lack of protein damage under the conditions required to incorporate a di-homocysteine containing peptide into a thiol-ene polymer.

The result is shown in FIG. 10. Exposure of lysozyme to the homocysteine-mediated reaction driven to completion results in complete rescue from the damaging effects caused by exposure to the cysteine-mediated reaction (FIG. 10, compare lanes "Cys, 90" UV" and "hCys, 20" UV"). At the same time, complete network formation is expected to occur in the case of homocysteine-based crosslinker (Example 8), but not in the case of cysteine-based one. In the latter case, to drive the network formation to completion a tenfold increase in initiator concentration is required (FIG. 9, Example 8), which results in almost complete consumption of the cargo protein in the secondary processes, despite a very short reaction time (lane "Cys, 10" UV").

Example 10: Influence of Oxygen on the Rate of Consumption of Free Thiol Groups in the Course of Photo-Induced Thiol-Ene Reaction To assess influence of dissolved oxygen on the reactivity of thiols in photoinitiated thiol-ene reactions, a 4 mL solution containing linear PEG-dinorbornene (MW 3.5 kDa) at a concentration of 6 mM, 0.01% (wt/vol) NAP, and a PEG-dithiol (MW 3.5 kDa) at a concentration of 6 mM (i.e. thiol groups and norbornene groups are present in a stoichiometric ratio) was prepared. The solution was then separated into two 2 mL aliquots, and one of the aliquots was subjected to oxygen removal by bubbling a low-pressure stream of argon through the solution for 20 minutes (degassing); the second 2 mL aliquot was used without degassing. 40 µL aliquots of each of the solutions were then irradiated with 385 nm light at 19 mW/cm2 in a cone-shaped-bottom 96-well polypropylene plate for the time indicated. Subsequently, 10 µL aliquots were withdrawn from the irradiated samples, diluted 11-fold with deionized water and the concentration of the remaining free thiol groups was measured by Ellman's assay as described in the Example 5 above. All data points were collected in duplicate, and average values and standard deviations were calculated according to standard statistical techniques.

Figure 11:
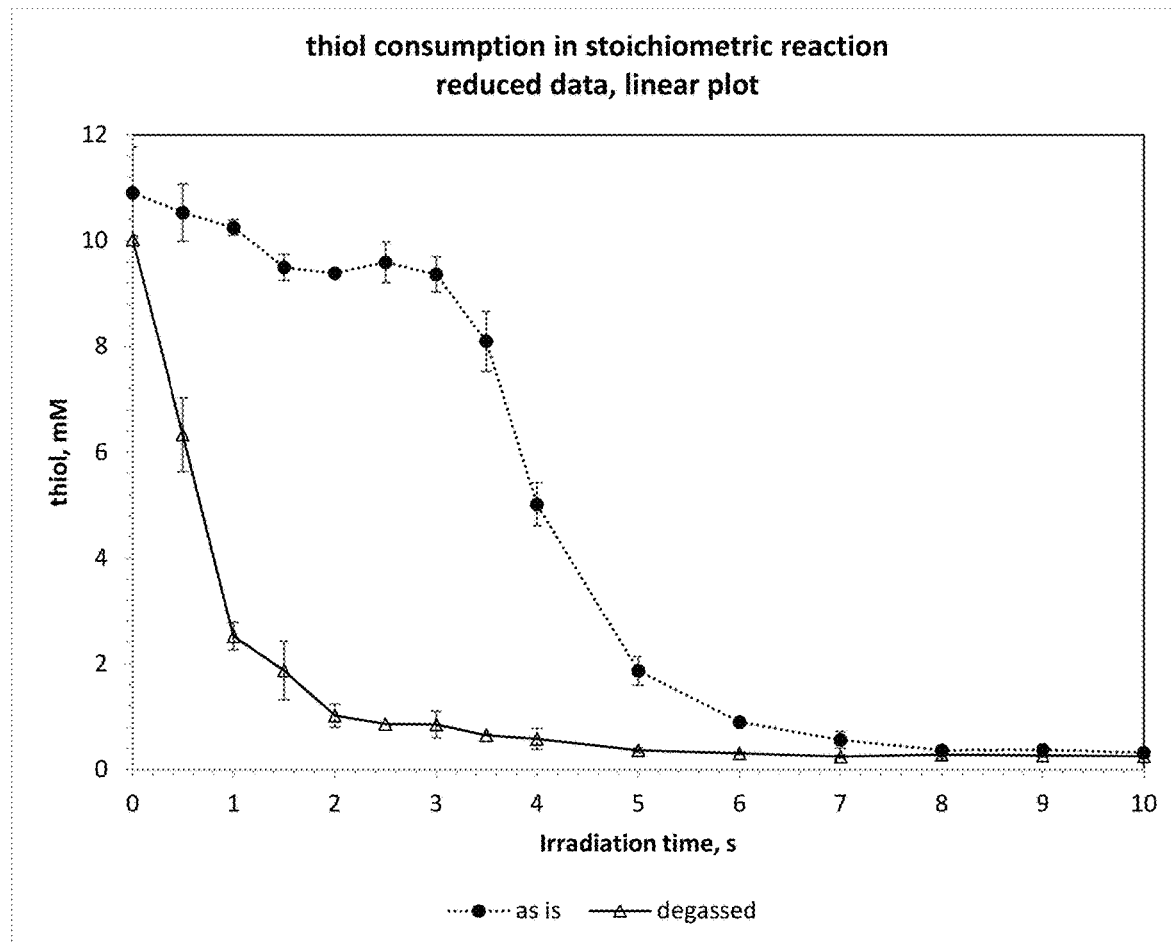
FIG. 11 demonstrates the influence of the presence of oxygen in solution on the rate of the photoinitiated thiol-ene reaction as monitored by the rate of consumption of free thiol groups by Ellman's assay.

The kinetics of consumption of free thiols for the untreated ("as is") and degassed reactions are compared in FIG. 11. The untreated ("as is") reaction exhibits a notable activation delay period of ~3-4 s, after which time it rapidly proceeds to completion within an additional 4 s. Degassing the reactant solution eliminates the activation delay period completely, and reaction proceeds significantly faster, nearing completion within the first 4 seconds of irradiation.

Example 11: Influence of Modification of Backbone

Figure 8A:
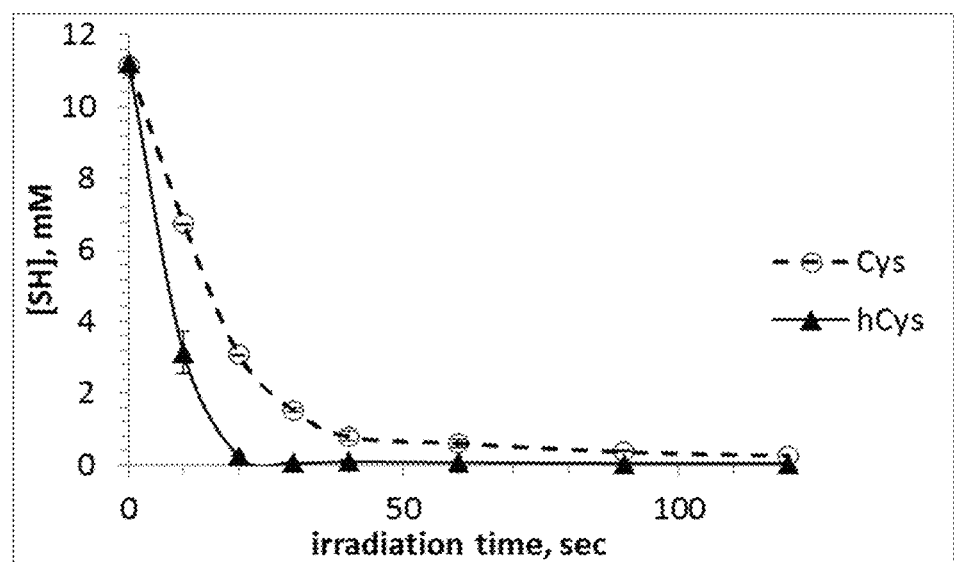
FIGS. 8A and 8B show results from the Ellman's assay demonstrating the consumption of free thiol groups in the course of photoinitiated thiol-ene reaction for multiple thiol containing compounds including homocysteine.
Figure 8B:
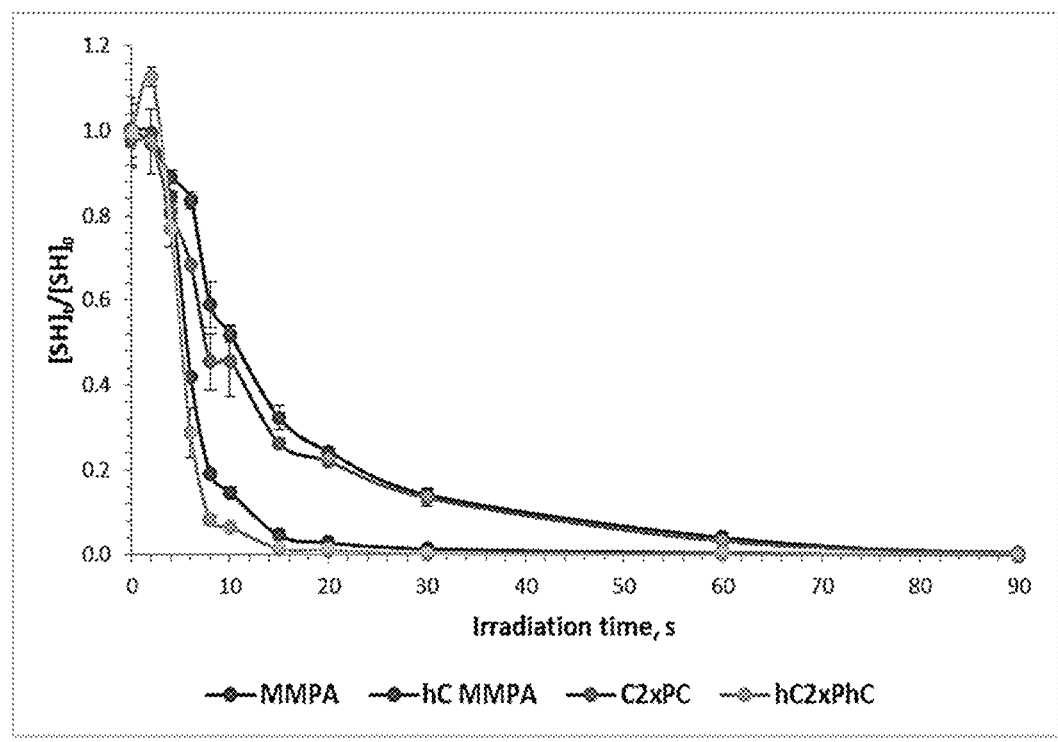
Figure 12A:
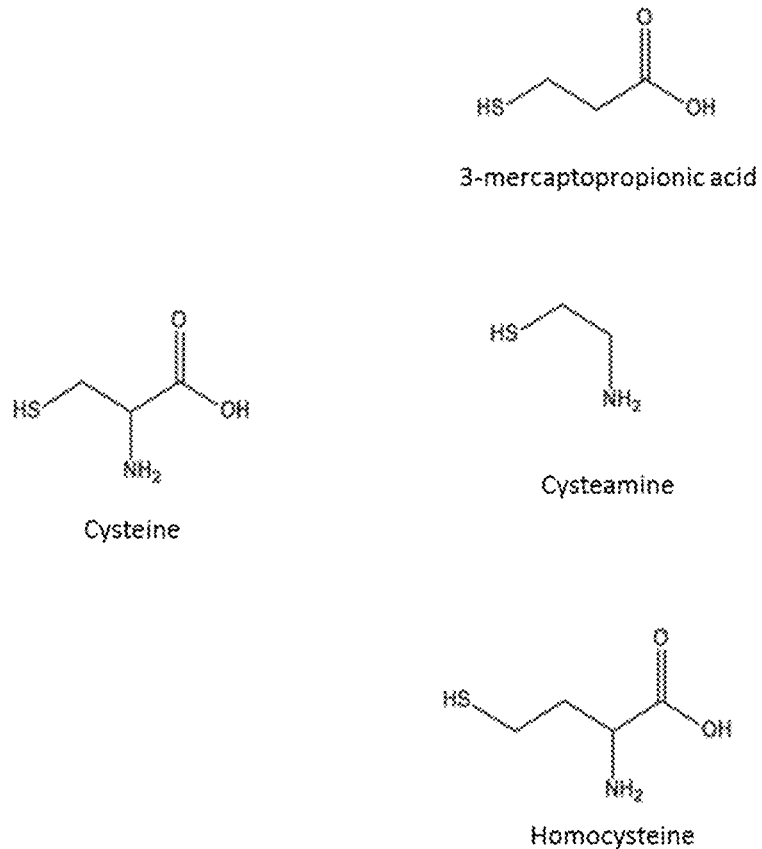
FIG. 12A shows representative structures of thiol compounds with various backbones.

In previous examples, it was demonstrated that increasing the side chain length (for example adding a carbon to cysteine to form homocysteine) increased the activity of the thiol group for radical thiol-ene chemistry (see FIGS. 8A and 8B). To assess the influence of the modification of the backbone of cysteine (i.e. the alpha-amino acid moiety rather than the side chain) on the reactivity of thiols in photoinitiated thiol-ene reaction, a 4 mL solution containing linear PEG-dinorbornene (MW 3.5 kDa) at a concentration of 6 mM, 0.01% (wt/vol) NAP, and one of 4 different thiols at a concentration of 12 mM (i.e. thiol groups and norbornene groups are present in a stoichiometric ratio), was prepared. These thiols included cysteine, homocysteine, 3-mercaptopropionic acid, and cysteamine (see FIG. 12A). 40 µL aliquots of each of the solutions were then irradiated with 385 nm light at 19 mW/cm² in a cone-shaped-bottom 96-well polypropylene plate for the time indicated. Subsequently, 10 microliter aliquots were withdrawn from irradiated samples, diluted 11-fold with deionized water and the concentration of the remaining free thiol was measured by Ellman's assay as described in the Example 5 above. All data points were collected in duplicate, and average values and standard deviations were calculated according to standard statistical techniques.

Figure 12B:
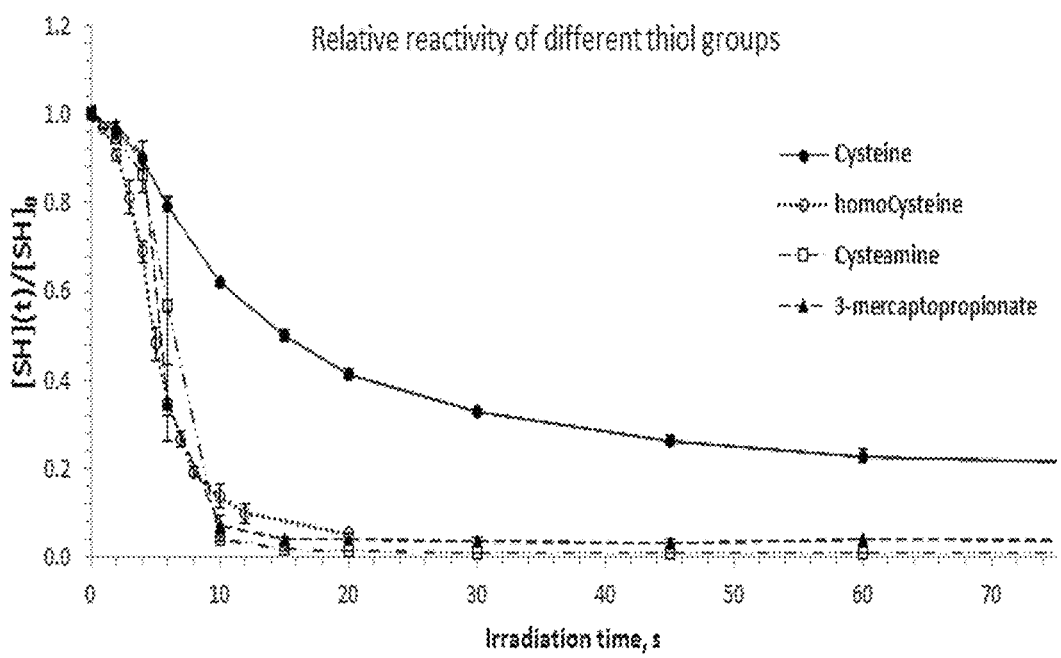
FIG. 12B shows results from the Ellman's assay demonstrating the influence of the modification of the cysteine backbone on the consumption of free thiol groups in the course of a photoinitiated thiol-ene reaction.

The kinetics of consumption of free thiols for the each of the compounds are compared in FIG. 12B. From this comparison, it is clear that backbone modifications (in this case removing either the carboxyl group or the amine) can lead to a similar rate enhancement as was seen with homocysteine.

REFERENCES (1) Chan W. C. and White P. D. (Eds.) 2000. Fmoc Solid Phase Peptide Synthesis. A Practical Approach. New York, N.Y.: Oxford University Press.

(2) Yan J-J, Sun J-T, You Y-Z, Wu D-C, Hong C-Y. Growing Hyperbranched Polymers Using Natural Sunlight. *Scientific Reports* 2013; 3:2841.

(3) Espeel P., Goethals F. & Du Prez F. E. One-pot multistep reactions based on thiolactones: extending the realm of thiol-ene chemistry in polymer synthesis. J. Am. Chem. Soc. 133, 1678-1681 (2011).

(4) McCall J D, Anseth K S. Thiol-Ene Photopolymerizations Provide a Facile Method To Encapsulate Proteins and Maintain Their Bioactivity. *Biomacromolecules* 2012; 13(8):2410-2417.

(5) Mariner P D, Wudel J M, Miller D E, Genova E E, Streubel S-O, Anseth K S. Synthetic hydrogel scaffold is an effective vehicle for delivery of INFUSE (rhBMP2) to critical-sized calvaria bone defects in rats. *Journal of orthopaedic research: official publication of the Orthopaedic Research Society* 2013; 31(3):401-406.

(6) Anderson S, Lin C, Kuntzler D, Anseth K. "The performance of human mesenchymal stem cells encapsulated in cell-degradable polymer-peptide hydrogels: Biomaterials 2011; 32(14):3564-3574.

(7) Hoyle, C. E., Lee, T. Y. and Roper, T. (2004), Thiol-enes: Chemistry of the past with promise for the future. J. Polym. Sci. A Polym. Chem., 42: 5301-5338.

All references throughout, such as publications, patents, patent applications and published patent applications, are incorporated herein by reference in their entireties.

Although the foregoing invention has been described in some detail by way of illustration and example for purposes of clarity of understanding, it is apparent to those skilled in the art that certain minor changes and modifications will be practiced. Therefore, the description and examples should not be construed as limiting the scope of the invention.

The invention claimed is:

1. A method for selectively linking a polypeptide in the presence of one or more cysteine residues,
wherein the polypeptide comprises a peptide backbone comprising a homocysteine residue having a reactive thiol group or a 2-amino-5-mercaptopentanoic acid residue having a reactive thiol group,
wherein the method comprises reacting the reactive thiol group of the homocysteine residue or the 2-amino-5-mercaptopentanoic acid residue of the polypeptide with an ene compound comprising one or more reactive ene groups under conditions that promote a radical-mediated thiol-ene reaction.

2. The method according to claim 1, wherein the radical-mediated thiol-ene reaction is initiated with a radical initiator.

3. The method according to claim 1, wherein comprises a homocysteine residue.

4. The method according to claim 2, wherein the radical initiator is a photoinitiator selected from the group consisting of lithium phenyl-2,4,6-trimethylbenzoylphosphinate (LAP), sodium phenyl-2,4,6-trimethylbenzoylphosphinate (NAP), 2-hydroxy-1-[4-(2-hydroxyethoxy)phenyl]-2-methyl-1-propanone, 1-hydroxy-cyclohexyl-phenyl-ketone and 2,2-dimethoxy-1,2-diphenylethan-1-one.

5. The method according to claim 4, wherein a thiol-ene reaction is initiated by exposing the photoinitiator to a light having a wavelength and an intensity during an exposure time, wherein:
when the photoinitiator is lithium phenyl-2,4,6-trimethylbenzoylphosphinate (LAP) or sodium phenyl-2,4,6-trimethylbenzoylphosphinate (NAP), the wavelength is approximately 360 nm, 372 nm, 380 nm, or 385 nm;
when the photoinitiator is 2-hydroxy-1-[4-(2-hydroxyethoxy)phenyl]-2-methyl-1-propanone, the wavelength is approximately 276 nm or 331 nm;
when the photoinitiator is 1-hydroxy-cyclohexyl-phenyl-ketone, the wavelength is approximately 246 nm, 280 nm, or 333 nm; and
when the photoinitiator is 2,2-dimethoxy-1,2-diphenylethan-1-one, the wavelength is approximately 254 nm or 337 nm.

6. The method according to claim 4, wherein the method further comprises controlling the amount of the photoinitiator, the intensity of the light and the time the photoinitiator is exposed to the light.

7. The method according to claim 6, wherein the thiol-ene reaction reaches between about 70% completion and about 95% completion.

8. The method according to claim 1, wherein the ene compound is an ene-modified biocompatible monomer.

9. The method according to claim 8, wherein the ene compound is a norbornene-modified polyethylene glycol (PEG).

10. The method according to claim 8, wherein the polypeptide further comprises a peptide sequence known to be sensitive to a protease.

11. The method according to claim 10, wherein the thiol-ene reaction provides a biocompatible cross-linked degradable hydrogel polymer.

12. The method of claim 1, wherein the ene compound comprises one or more norbornene groups.

13. The method according to claim 1, wherein the polypeptide is selected from peptide or protein hormones, growth factors, cytokines, interleukins, receptors, solubilized receptors, therapeutic proteins, enzymes and structural proteins.

\* \* \* \* \*

```
                           SEQUENCE LISTING

<160> NUMBER OF SEQ ID NOS: 6

<210> SEQ ID NO 1
<211> LENGTH: 12
<212> TYPE: PRT
<213> ORGANISM: Artificial Sequence
<220> FEATURE:
<223> OTHER INFORMATION: Synthetic Construct

<400> SEQUENCE: 1

Lys Cys Gly Pro Gln Gly Ile Ala Gly Gln Cys Lys
1               5                   10

<210> SEQ ID NO 2
<211> LENGTH: 9
<212> TYPE: PRT
<213> ORGANISM: Artificial Sequence
<220> FEATURE:
<223> OTHER INFORMATION: Synthetic Construct

<400> SEQUENCE: 2

Cys Ala Leu Lys Val Leu Lys Gly Cys
1               5

<210> SEQ ID NO 3
<211> LENGTH: 11
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 3, 8
<223> OTHER INFORMATION: Protected by a Trt group
<220> FEATURE:
<221> NAME/KEY: VARIANT
<222> LOCATION: 10
<223> OTHER INFORMATION: Protected by a Dde group

<400> SEQUENCE: 3

Gly Pro Gln Gly Ile Trp Gly Gln Gly Lys Gly
1               5                   10

<210> SEQ ID NO 4
<211> LENGTH: 11
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 3, 8
<223> OTHER INFORMATION: Protected by a Trt group

<400> SEQUENCE: 4

Gly Pro Gln Gly Ile Trp Gly Gln Gly Lys Gly
1               5                   10

<210> SEQ ID NO 5
<211> LENGTH: 13
<212> TYPE: PRT
<213> ORGANISM: Artificial Sequence
```

```
<220> FEATURE:
<223> OTHER INFORMATION: Synthetic Construct
<220> FEATURE:
<221> NAME/KEY: VARIANT
<222> LOCATION: 2, 12
<223> OTHER INFORMATION: Protected by a Boc group
<220> FEATURE:
<221> NAME/KEY: VARIANT
<222> LOCATION: 3, 11
<223> OTHER INFORMATION: Protected by a Dde group
<220> FEATURE:
<221> NAME/KEY: VARIANT
<222> LOCATION: 4, 9
<223> OTHER INFORMATION: Protected by a Trt group

<400> SEQUENCE: 5

Gly Lys Lys Gln Gly Ile Trp Gly Gln Gly Lys Lys Gly
1               5                   10

<210> SEQ ID NO 6
<211> LENGTH: 13
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 2, 12
<223> OTHER INFORMATION: Protected by a Boc group
<220> FEATURE:
<221> NAME/KEY: VARIANT
<222> LOCATION: 4, 9
<223> OTHER INFORMATION: Protected by a Trt group

<400> SEQUENCE: 6

Gly Lys Lys Gln Gly Ile Trp Gly Gln Gly Lys Lys Gly
1               5                   10
```